United States Patent [19]

Jacobson

[11] Patent Number: 4,663,341

[45] Date of Patent: May 5, 1987

[54] INSECTICIDAL N-ARYL-3-ARYL-4,5-DIHYDRO-1H-PYRAZOLE-1-CARBOXAMIDES

[75] Inventor: Richard M. Jacobson, Chalfont, Pa.

[73] Assignee: Rohm and Haas Company, Philadelphia, Pa.

[21] Appl. No.: 689,671

[22] Filed: Jan. 11, 1985

Related U.S. Application Data

[63] Continuation-in-part of Ser. No. 580,963, Feb. 15, 1984, abandoned.

[51] Int. Cl.⁴ ..................... A01N 43/56; A01N 43/54; C07D 231/06; C07D 417/14
[52] U.S. Cl. ................................... 514/403; 514/256; 514/269; 514/272; 514/274; 514/275; 514/333; 514/341; 514/365; 514/369; 514/370; 514/371; 514/372; 514/374; 514/376; 514/377; 514/378; 514/380; 514/397; 514/406; 514/407; 544/296; 544/297; 544/298; 544/300; 544/310; 544/315; 544/316; 544/317; 544/318; 544/319; 544/320; 544/321; 544/322; 544/324; 544/327; 544/328; 544/331; 544/333; 546/256; 546/277; 546/278; 546/279; 548/182; 548/183; 548/184; 548/185; 548/186; 548/187; 548/188; 548/189; 548/190; 548/191; 548/192; 548/193; 548/194; 548/195; 548/196; 548/197; 548/198; 548/199; 548/200; 548/201; 548/202; 548/203; 548/205; 548/206; 548/213; 548/214; 548/225; 548/226; 548/227; 548/228; 548/229; 548/230; 548/231; 548/232; 548/233; 548/234; 548/235; 548/236; 548/243; 548/244; 548/245; 548/246; 548/247; 548/248; 548/249; 548/336; 548/374; 548/379
[58] Field of Search ............... 548/379, 182, 183, 184, 548/185, 186, 187, 188, 189, 190, 191, 192, 193, 194, 195, 196, 197, 198, 199, 200–203, 205, 206, 213, 214, 225–236, 243–249, 336, 374, 379; 514/403, 256, 269, 272, 274, 275, 333, 341, 365, 369–372, 374, 376–378, 380, 397, 403, 406, 407; 544/296, 297, 298, 300, 310, 315, 316, 317, 318, 319, 320, 321, 322, 324, 327, 328, 331, 333; 546/256, 277, 278, 279

[56] References Cited

U.S. PATENT DOCUMENTS

| | | |
|---|---|---|
| 3,991,073 | 11/1976 | Mulder et al. ................... 548/379 |
| 4,010,271 | 3/1977 | Mulder et al. ................... 548/379 |
| 4,070,365 | 1/1978 | Van Daalen et al. ............ 548/379 |
| 4,095,026 | 6/1978 | Mulder et al. ................... 548/379 |
| 4,140,787 | 2/1979 | Sirrenberg et al. .............. 548/379 |
| 4,140,792 | 2/1979 | Sirrenberg et al. .............. 548/379 |
| 4,156,007 | 5/1979 | Van Daalen et al. ............ 548/379 |
| 4,174,393 | 11/1979 | Van Daalen et al. ............ 548/379 |
| 4,407,813 | 10/1983 | Ozawa et al. ................... 548/379 |
| 4,439,440 | 3/1984 | Van Hes et al. ................. 548/379 |
| 4,464,386 | 8/1984 | Ozawa et al. ................... 548/379 |

FOREIGN PATENT DOCUMENTS

| | | |
|---|---|---|
| 0004733 | 10/1979 | European Pat. Off. ............ 548/379 |
| 0021506 | 1/1981 | European Pat. Off. ............ 548/379 |
| 0058424 | 8/1982 | European Pat. Off. ............ 548/379 |
| 0065334 | 11/1982 | European Pat. Off. ............ 548/379 |

OTHER PUBLICATIONS

Chem Abst., Index Guide, 1982, pp. 210I–216I.
Crawford et al., "The Synthesis and Physical Properties of Some 1- and 2-Pyrazolines", *J. Am. Chem. Soc.* 88: 3954–3963 (1966).
Mulder et al., "A New Class of Insecticides", *Naturwissenschaften* 62: 531–532 (1975).
Tamaki, "TH 6041: Knockdown and Feeding Inhibition of the Zebra Caterpillar and the Colorado Potato Beetle", *J. Econ. Entomol.* 69: 644–646 (1976).
Dilli, "Gas Chromatography of the Pyrazoline Derivative of Trimethyl Aconitate", *J. Chrom.* 132: 148–151 (1977).
Kramer et al., "Activity of TH-6041 and TH-6042 Against Stored-Product Insects", *J. Econ. Entomol.* 71: 825–826 (1978).
Van Hes et al., "A-Phenylcarbamoyl-2-pyrazolines: A New Class of Insecticides, 2, Synthesis and Insecticidal Properties of 3,5-Diphenyl-1-Phenylcarbamoyl-2-Pyrazolines," *J. Agric. Food Chem.* 26: 915–918 (1978).
Grosscurt et al., "1-Phenylcarbamoyl-2-pyrazolines, a New Class of Insecticides, 3, Synthesis and Insecticidal Properties of 3,4-Diphenyl-1-Phenylcarbamoyl-2-Pyrazolines", *J. Agric. Food Chem.* 27: 406–409 (1979).
Fuhr et al., *Chemosphere* 9: 469–482 (1980).
Ascher et al., "Certain Aspects of the Toxicity of PH60-42, a 1-Phenylcarbamoylpyrazoline, for *Spodoptera liHoralis* Larvae", *International Pest Control*, May/Jun.: 76–78 (1981).

*Primary Examiner*—Richard A. Schwartz
*Assistant Examiner*—Kurt G. Briscoe
*Attorney, Agent, or Firm*—John C. Demeter; Douglas E. Winters

[57] ABSTRACT

This invention relates to N-aryl-3-aryl-4,5-dihydro-1H-pyrazole-1-carboxamide compounds which are useful as pesticides, compositions containing those compounds, methods of controlling pests and processes for preparing these compounds.

49 Claims, No Drawings

INSECTICIDAL N-ARYL-3-ARYL-4,5-DIHYDRO-1H-PYRAZOLE-1-CARBOXAMIDES

BACKGROUND OF THE INVENTION

This application is a continuation-in-part of U.S. patent application Ser. No. 580,963, filed Feb. 15, 1984, now abandoned.

This invention relates to novel N-aryl-3-aryl-4,5-dihydro-1H-pyrazole-1-carboxamides which are useful as pesticides, compositions containing those compounds, methods of controlling pests and processes for preparing the compounds of the present invention.

The search for pesticides which have a combination of excellent pesticidal activity and essentially no toxicity is a continuing one due to recognition of the possible toxicity to animals and humans of many known pesticides.

Certain pyrazoline derivatives have been disclosed as having insecticidal activity.

German Offenlegungsschrift No. 2,304,584 discloses pyrazoline compounds which are substituted in the 1,3 or 1,3,5 positions of the pyrazoline ring that exert biocidal activity. German Offenlegungsschrift No. 2,304,584 corresponds to U.S. Pat. Nos. 3,991,073; 4,095,026; and 4,010,271.

U.S. Pat. Nos. 4,156,007; 4,070,365; and 4,174,393 disclose pyrazoline compounds which are substituted in the 1,3 and 4 positions of the pyrazoline ring that have insecticidal activity.

U.S. Pat. Nos. 4,140,787 and 4,140,792 disclose pyrazoline compounds which are substituted in the 1,3,5 positions of the pyrazoline ring that possess anthropodicidal properties.

Presently known compounds are believed to be subject to problems with photostability and biodegradability. These compounds tend to degrade faster than is desirable when applied to the external parts of plants due to the action of sunlight on these compounds. Moreover, when known compounds are applied to the soil, they exhibit poor biodegradability causing an undesirable residue to remain in the soil.

The present invention discloses N-aryl-3-aryl-4,5-dihydro-1H-pyrazole-1-carboxamides (hereinafter at times referred to as 1-substituted-4-substituted-4,5-dihydro-1H-pyrazoles), including N-aryl-3-aryl-4,5-dihydro-1H-pyrazole-1-thiocarboxamides and include N-aryl-3-aryl-4,5-dihydro-1H-pyrazole-1-iminocarboxamides which are disubstituted at the 4 position or monosubstituted at the 4 position. When these compounds are monosubstituted at the 4 position, the substituent has, at the 4-position, 1-oxo, 1-thiono or 1-imino functionality.

It is believed this 4,4-disubstitution greatly lessens photodegradation and metabolic pathway transformations in plants and insects by blocking hydrogen loss and subsequent aromatization of the dihydropyrazole moiety to a pyrazole moiety resulting in an inactivation of the compound as an insecticide.

Certain of the 4-carboalkoxy substituted compounds (4-monosubstituted and 4-disubstituted) of this invention exhibit enhanced rates of soil metabolism thus minimizing undesirable residues.

It is therefore an object of the invention to provide novel compounds, and compositions containing said compounds, which possess pesticidal activity. It is another object of the present invention to provide compounds which demonstrate improved photostability and biodegradability. It is a further object of the invention to provide methods for the synthesis of 1-substituted-4-substituted-4,5-dihydro-1H-pyrazoles. It is still another object of the present invention to provide methods for controlling pests and insects using the novel compounds.

These and other objects of the invention will become apparent to those skilled in the art from the following description.

SUMMARY OF THE INVENTION

In accordance with the present invention, there are provided compounds having the formula:

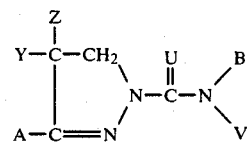

wherein
A is unsubstituted or substituted aryl;
B is unsubstituted or substituted aryl;
U is O, S or N—Q;
V is hydrogen, $(C_3-C_6)$cycloalkyl, unsubstituted or substituted aryl or $R^4$—Q;
Y is
lower $(C_1-C_6)$ straight or branched chain unsubstituted or substituted alkyl, unsubstituted or substituted aryl where the substituent(s) is selected from Q (hereinafter at times referred to as Group A); or
a group having the formula

where X is O or S and G is as defined below (hereinafter at times referred to as Group B);
when Y is Group A,
Z is cycloalkyl$(C_3-C_6)$, unsubstituted or substituted aryl or $R^4$—Q provided that Z is not hydrogen and Z is not methyl when Y is methyl;
when Y is Group B,
Z is hydrogen, cycloalkyl$(C_3-C_6)$, unsubstituted or substituted aryl or $R^4$—Q;
Q is hydrogen, halogen, cyano, nitro, $OR^1$, $R^4OR^1$, $CO_2R^1$, $OR^4OR^1$, $CR^1R^2R^3$, $CONR^1R^2$, $NR^1R^2$, $NR^1COR^2$, $N(COR^1)COR^2$, $CSR^1$, $SR^1$, $SOR^1$, $SO_2R^1$, $NR^1SOR^2$, $R^4SR^1$, $OR^4SR^1$, $SR^4SR^1$, $SNHSR^1$, $SNHSO_2R^1$, $CONHSR^1$, $OCOR^1$, $R^1$, $C(=NR^1)R^2$, $COR^1$, $N_3$, $OSO_2R^1$, $NR^1SO_2R^2$, $NR^1CSR^2$, alkenyl $(CR^1=CR^2R^3)$, alkynyl $(C\equiv CR^1)$, or aryl;
$R^1$, $R^2$ and $R^3$ are, independently, hydrogen, halogen, cyano, nitro, hydroxy, an alkoxy group (OR) having up to four carbon atoms, an amino group $(NH_2)$, an alkylamino group (NHR) having up to six carbon atoms, a dialkylamino group $(NR_2)$ having, independently, up to six carbon atoms in each alkyl moiety, a carboxy group $(CO_2H)$, a carbalkoxy group $(CO_2R)$ having up to six carbon atoms, an alkylcarbonyl group (COR) having up to six carbon atoms, an alkanoyloxy group (OCOR) having up to six carbon atoms, a carboxamido group $(CONH_2)$, an N-alkylcarboxamido group (CONHR) having up to six carbon atoms in the alkyl moiety, an N,N-dialkylcarboxamido group (CONR$_2$) having independently, up to six carbon atoms in each alkyl moiety, a carbamoyloxy group (OCONH$_2$), N-alkylcarbamoxyloxy group (OCONHR) having up to six carbon atoms in the alkyl moiety, an N,N-dialkylcarbamoyloxy group (OCONR$_2$) having, independently, up to six carbon atoms in each alkyl moeity, a sulfhydril, an alkylsulfinyl group (—SOR) having up to six carbon atoms, an alkylsulfonyl group (—SO$_2$R) having up to six carbon atoms, an alkylsulfonato group (—OSO$_2$R) having up to six carbon atoms, an alkylthio group (SR) having up to six carbon atoms, a sulfonamido (SO$_2$NH$_2$), an N-alkylsulfonamido (SO$_2$NHR) having up to six carbon atoms in the alkyl moiety, an N,N-dialkylsulfonamido (SO$_2$NR$_2$) having, independently, up to six carbon atoms in each alkyl moiety, an N-alkyl-N-acylamino group (NRCOR) having independently, up to six carbon atoms in each alkyl moiety, an N-alkyl-N-alkylsulfonylamino (NRSO$_2$R) having, independently, up to six carbon atoms in each alkyl moiety, an alkylthiocarbonyl group (CSR) having up to six carbon atoms, an N-alkyl-N-thioacylamino group (NRCSR) having, independently, up to six carbon atoms in each alkyl moiety, an N-alkyl-N-alkylsulfinylamino (NRSOR) having, independently, up to six carbon atoms in each alkyl moiety, a N,N-diacylamino group (N(COR)COR) having, independently, up to six carbon atoms in each alkyl moiety, an unsubstituted or substituted straight or branched chain lower (C$_1$–C$_6$)alkyl, (C$_3$–C$_6$)cycloalkyl or aryl where the substituent on the alkyl moiety can be one or more of the same or different hydroxy, halogen, cyano, nitro, or an alkoxy group (OR) having up to four carbon atoms, an amino group (NH$_2$), an alkylamino group (NHR) having up to six carbon atoms, a dialkylamino group (NR$_2$) having, independently, up to six carbon atoms in each alkyl moiety, a carboxy group (CO$_2$H), a carbalkoxy group (CO$_2$R) having up to six carbon atoms, an alkylcarbonyl group (COR) having up to six carbon atoms, an alkanoyloxy group (OCOR) having up to six carbon atoms, a carboxamido group (CONH$_2$), an N-alkylcarboxamido group (CONHR) having up to six carbon atoms in the alkyl moiety, an N,N-dialkylcarboxamido group (CONR$_2$) having independently, up to six carbon atoms in each alkyl moiety, a carbamoyloxy group (OCONH$_2$), an N-alkylcarbamoyloxy group (OCONHR) having up to six carbon atoms in the alkyl moiety, an N,N-dialkylcarbamoyloxy group (OCONR$_2$) having, independently, up to six carbon atoms in each alkyl moiety, a sulfhydril, an alkylsulfinyl group (—SOR) having up to six carbon atoms, an alkylsulfonyl group (—SO$_2$R) having up to six carbon atoms, an alkylsulfonato group (—OSO$_2$R) having up to six carbon atoms, an alkylthio group (SR) having up to six carbon atoms, a sulfonamido (SO$_2$NH$_2$), an N-alkylsulfonamido (SO$_2$NHR) having up to six carbon atoms in the alkyl moiety, an N,N-dialkylsulfonamido (SO$_2$NR$_2$) having independently, up to six carbon atoms in each alkyl moiety, an N-alkyl-N-acylamino group (NRCOR) having, independently, up to six carbon atoms in each alkyl moiety, an N-alkyl-N-alkylsulfonylamino (NRSO$_2$R) having independently, up to six carbon atoms in each alkyl moiety, an alkylthiocarbonyl group (CSR) having up to six carbon atoms, an N-alkyl-N-thioacylamino group (NRCSR) having, independently, up to six carbon atoms in each alkyl moiety, an N-alkyl-N-alkylsulfinylamino (NRSOR) having, independently, up to six carbon atoms in each alkyl moiety, a N,N-diacylamino group (N(COR)COR) having, independently, up to six carbon atoms in each alkyl moiety, or an aryl group, where R is an alkyl group having the stated number of carbon atoms;

R$^4$ is

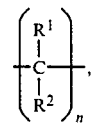

where R$^1$ and R$^2$ are independent for each carbon atom of a chain;

G is (C$_3$–C$_6$)cycloalkyl, unsubstituted or substituted aryl or R$^4$—Q;

n is from 0 to 10;

and agronomically acceptable salts thereof.

Halogen can be chosen from fluorine, chlorine, bromine, or iodine;

Cycloalkyl can be chosen from cyclopropyl, cyclobutyl, cyclopentyl, cyclohexyl, cycloheptyl, cyclooctyl, cyclononyl, cyclodecyl, cycloundecyl, and cyclododecyl.

Aryl can be chosen from phenyl, optionally substituted with 1–5 substituents independently chosen from W; naphthyl, optionally substituted with 1–7 substituents independently chosen from W; a 5 membered heterocycle containing up to 2 nitrogen atoms, up to 2 oxygen atoms, up to 2 sulfur atoms and up to 4 nuclear carbon atoms, optionally substituted with 1–4 substituents independently chosen from W; or a 6 membered heterocycle containing up to 3 nitrogen atoms, up to 2 oxygen atoms, up to 2 sulfur atoms and 1–5 nuclear carbon atoms optionally substituted with 1–4 substituents independently chosen from W. Representative examples of 5 and 6 membered heterocycles include pyrryl, furyl, thienyl, imidazolyl, oxazolyl, thiazolyl, pyrazolyl, pyridyl, pyrimidyl and the like.

W is halogen, cyano, nitro, R$^1$, CO$_2$R$^1$, CONR$^1$R$^2$, CR$^1$=CR$^2$R$^3$, C≡CR$^1$, SR$^1$, OR$^1$, NR$^1$R$^2$, SOR$^1$, SO$_2$R$^1$, OSO$_2$R$^1$, NR$^1$COR$^2$, SF$_5$, CF$_3$, OCF$_3$, OCF$_2$H, SCF$_3$, OCF$_2$Br, SCF$_2$Br, SCF$_2$Cl, SCF$_2$H, NR$^1$SO$_2$R$^2$ or N(COR$^1$)COR$^2$.

Further, in accordance with the present invention, there are provided compositions containing compounds of the present invention and processes for preparing 1-substituted-4-substituted-4,5-dihydro-1H-pyrazoles of the present invention. One process comprises dissolving a 1-substituted-4,5-dihydro-1H-pyrazole in an aprotic solvent, mixing a strong base with the resulting solution, allowing deprotonation to take place at the 4 position of the pyrazole ring, and then adding an alkylating or acylating agent, wherein the 1-substituted-4,5-dihydro-1H-pyrazole dissolved in the aprotic solvent must be a 1-substituted-4-monosubstituted-4,5-dihydro-1H-pyrazole when the desired end product is a 1-substituted-4,4-disubstituted-4,5-dihydro-1H-pyrazole.

A second process for preparing compounds of the present invention where Y is a group having the formula

(Group B) comprises treating a beta-dicarbonyl compound of the formula:

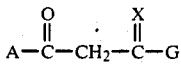   II where A, X and G are as defined above with a mixture of hydrazine and formaldehyde to produce a 3-aryl-4-monosubstituted-4,5-dihydropyrazole having the formula:

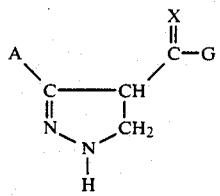   III where A, X and G are as defined above.

Treatment of the dihydropyrazole of Formula III with an aryl isocyanate affords the N-aryl-3-aryl-4-mono-substituted-4,5-dihydropyrazole-1-carboxamides of this invention.

Further treatment of this 1-substituted-4-mono-substituted-4,5-dihydropyrazole-1-carboxamide with a base, followed by an alkylating agent or acylating agent will yield the N-aryl-3-aryl-4,4-disubstituted-4,5-dihydropyrazole-1-carboxamides of this invention.

DETAILED DESCRIPTION OF THE INVENTION

The compounds of the instant invention are N-aryl-3-aryl-4,5-dihydro-1H-pyrazole-1-carboxamides which are disubstituted at the 4 position of the pyrazole ring and 4,5-dihydro-1H-pyrazole-1-carboxamides which are monosubstituted at the 4 position of the pyrazole ring, said monosubstituted compounds having 1-oxo or 1-thiono functionality at the 4 position of the pyrazole ring. The substituents that may be covalently bonded at the 4 position of the pyrazole ring, whether monosubstituted or disubstituted, are defined by Y and Z in Formula I. It should be appreciated that certain compounds of the present invention can exist as geometric isomers; that is enantiomers or diastereomers. The present invention includes compounds and compositions as disclosed herein comprising substantially pure dextrorotatory, levorotatory or racemic mixtures of said compounds.

The 4,5-dihydro-1H-pyrazole-1-carboxamides of the instant invention are deemed to include 4,5-dihydro-1H-pyrazole-1-thiocarboxamides and 4,5-dihydro-1H-pyrazole-1-iminocarboxamides. When U in Formula I is oxygen, the compound is an oxocarboxamide and when U is sulfur in Formula I, the compound is a thiocarboxamide and when U is N—Q, the compound is an iminocarboxamide. The preferred U substituent is oxygen.

The relationship between Y and Z is such that when Y is lower (C₁-C₆) straight or branched chain unsubstituted or substituted alkyl, unsubstituted or substituted aryl, (Group A), Z can be cycloalkyl(C₃-C₆), unsubstituted or substituted aryl or R⁴—Q provided that Z is not hydrogen and Z is not methyl when Y is methyl. When Y is

(Group B) where X and G are as defined above for Formula I, Z can be hydrogen, cycloalkyl(C₃-C₆), unsubstituted or substituted aryl or R⁴—Q.

The only compounds of the invention which can be monosubstituted at the four position of the pyrazole ring (i.e., where Z is hydrogen) are those where Y is

and these monosubstituted compounds have, necessarily,

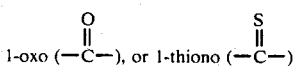

functionality at the 4 position of the pyrazole ring. Otherwise, the compounds of the present invention are disubstituted at the 4 position of the pyrazole ring.

Possible Z substituents, when Y is Group A include, but are not limited to: alkyl, aryl, aralkyl, haloalkyl, alkoxyalkyl, alkylthioalkyl, alkylsulfinylalkyl, cyanoalkyl, carboalkoxy, carboalkoxyalkyl, carboxamido, carboxyamidoalkyl, N-alkylcarboxamido, N-alkylcarboxamidoalkyl, N,N-dialkylcarboxamido, N,N-dialkylcarboxamidoalkyl, hydroxyalkyl, ketoalkyl, ketoaryl, thionoalkyl, thionoaryl, iminoalkyl, iminoaryl, halo, hydroxy, carboxy, dithiocarboxy, dithiocarboxyalkyl or dithiocarboalkoxy.

Preferred Z substituents when Y is Group A are phenyl, 4-chlorophenyl, carbomethoxy, carboethoxy, dimethylcarbamoyl, acetyl, propionyl, benzoyl, butyl, 2-methylthioethyl, 3-cyanopropyl, 2-methylsulfonylethyl or carbomethoxymethyl.

Possible Z substituents when Y has 1-oxo or 1-thiono functionality (Group B), as defined in Formula I include, but are not limited to: hydrogen, alkyl, aryl, aralkyl, haloalkyl, alkoxyalkyl, alkylthioalkyl, alkylsulfinylalkyl, cyanoalkyl, carboalkoxy, carboalkoxyalkyl, carboxamido, carboxamidoalkyl, N-alkylcarboxamido, N-alkylcarboxamidoalkyl, N,N-dialkylcarboxamido, N,N-dialkylcarboxamidoalkyl, hydroxyalkyl, ketoalkyl, ketoaryl, thionoalkyl, thionoaryl, iminoalkyl, iminoaryl, halo, hydroxy, carboxy, dithiocarboxy, dithiocarboxyalkyl or dithiocarboalkoxy.

Preferred Z substituents when Y has 1-oxo or 1-thiono functionality (Group B) are hydrogen, methyl, phenyl, 4-chlorophenyl, 4-trifluoromethylphenyl, 4-trifluoromethoxyphenyl, 4-trifluorothiomethoxyphenyl, 4-difluoromethoxyphenyl or 4-difluorobromothiomethoxyphenyl. The most preferred substituent is methyl.

When the compounds of the present invention are monosubstituted at the 4 position (Group B), those compounds having 1-oxo functionality at the Y substituent are preferred.

Examples of substituents for G include hydrogen, alkoxy, thioalkoxy, alkyl, hydroxy, alkoxyalkyl, thioalkoxyalkyl, alkoxyalkoxy, thioalkoxyalkoxy, amino, alkylamino, dialkylamino, carbalkoxy, cyano, ketoalkyl and alkyl substituted with alkoxy, thioalkoxy, carbalkoxy, cyano or alkylheteroalkyl. Preferred G substituents include methyl, ethyl, methoxy, ethoxy, hydroxy, dimethylamino and phenyl. Most preferred are methoxy, ethoxy or dimethylamino.

Substituent A may be aryl or substituted aryl. The preferred A substituent is unsubstituted or substituted phenyl and most preferred is substituted phenyl. While the phenyl group may be substituted with up to five substituents, it is preferred that it be unsubstituted, or monosubstituted or disubstituted with the same or different substituents and most preferred that the phenyl group be monosubstituted with the substituent located in the para position. Preferred phenyl substituents include fluoro, chloro, bromo, trifluoromethyl, trifluoromethoxy, difluoromethoxy or methyl. Most preferred substituents are chloro, bromo, trifluoromethyl, trifluoromethoxy or difluoromethoxy at the 4 position on the phenyl ring.

Substituent B may be aryl or substituted aryl. The preferred B substituent is unsubstituted or substituted phenyl and most preferred is substituted phenyl having up to two of the same or different substituents located in the 3 and/or 4 positions. When substituent B is monosubstituted, it is preferred the phenyl group be substituted in the para position. Preferred substituents include fluoro, chloro, bromo, trifluoromethyl, trifluoromethoxy, difluoromethoxy, carbomethoxy, carboethoxy, carboisopropoxy, methylthio or methylsulfonyl. Most preferred substituents include chloro, bromo, carbomethoxy, carboethoxy, carboisopropoxy, difluoromethoxy, trifluoromethoxy, trifluoromethyl, methylthio or methylsulfonyl.

Representative examples of substituent V include alkyl, branched alkyl, cycloalkyl, aryl or $R^4$—Q where Q and $R^4$ are as defined above for Formula I. Preferably, V is hydrogen, lower ($C_1$-$C_6$) straight or branched chain unsubstituted or substituted alkyl, lower ($C_1$-$C_6$)alkoxy, lower ($C_1$-$C_6$)alkylsulfenyl, unsubstituted or substituted arylsulfenyl, lower ($C_1$-$C_6$)carboalkoxy, cyano, lower ($C_1$-$C_6$)alkylheteroalkyl, wherein the substituent on the alkyl moiety is lower ($C_1$-$C_4$)alkoxy, lower ($C_1$-$C_4$)alkylsulfenyl, lower ($C_1$-$C_4$)carboalkoxy, cyano or lower ($C_1$-$C_4$)heteroalkyl. Most preferred are hydrogen, methyl, methylsulfenyl, 2-nitrophenylsulfenyl, carbomethoxy, acetyl, trifluoroacetyl, formyl or methoxalyl.

Aryl can be chosen from phenyl, optionally substituted with 1-5 substituents independently chosen from W; naphthyl, optionally substituted with 1-7 substituents independently chosen from W; a 5 membered heterocycle containing up to 2 nitrogen atoms, up to 2 oxygen atoms, up to 2 sulfur atoms and up to 4 nuclear carbon atoms, optionally substituted with 1-4 substituents independently chosen from W; or a 6 membered heterocycle containing up to 3 nitrogen atoms, up to 2 oxygen atoms, up to 2 sulfur atoms and 1-5 nuclear carbon atoms optionally substituted with 1-4 substituents independently chosen from W. Representative examples of 5 and 6 membered heterocycles include pyrryl, furyl, thiophenyl, imidazolyl, oxazolyl, thiazolyl, pyrazolyl, pyridyl, pyrimidyl and the like.

W is halogen, cyano, nitro, $R^1$, $CO_2R^1$, $CONR^1R^2$, $CR^1=CR^2R^3$, $C\equiv CR^1$, $SR^1$, $OR^1$, $NR^1R^2$, $SOR^1$, $SO_2R^1$, $OSO_2R^1$, $NR^1COR^2$, $SF_5$, $CF_3$, $OCF_3$, $OCF_2H$, $SCF_3$, $OCF_2Br$, $SCF_2Br$, $SCF_2Cl$, $SCF_2H$, $NR^1SO_2R^2$ or $N(COR^1)COR^2$.

Since the 1-substituted-4-substituted-4,5-dihydro-1H-pyrazoles of Formula I may possess acidic or basic functional groups, they may form novel salts with appropriate bases or acids which also exhibit pesticidal activity. Typical salts are the agronomically acceptable metal salts, ammonium salts and acid addition salts. Among the metal salts are those in which the metal cation is an alkali metal cation such as sodium, potassium, lithium or the like; alkaline earth metal cation such as calcium, magnesium, barium, strontium or the like; or heavy metal cation such as zinc, manganese, cupric, cuprous, ferric, ferrous, titanium, aluminum or the like. Among the ammonium salts are those in which the ammonium cation has the formula $NR^5R^6R^7R^8$ wherein each of $R^5$, $R^6$, $R^7$ and $R^8$ are independently a hydrogen atom, a hydroxy group, a ($C_1$-$C_4$)alkoxy group, a ($C_1$-$C_{20}$)alkyl group, a ($C_3$-$C_8$)alkenyl group, a ($C_3$-$C_8$)alkynyl group, a ($C_2$-$C_8$)hydroxyalkyl group, a ($C_2$-$C_8$)alkoxyalkyl group, a ($C_2$-$C_6$)aminoalkyl group, a ($C_2$-$C_6$)haloalkyl group, an amino group, a ($C_1$-$C_4$)alkyl or ($C_1$-$C_4$)dialkylamino group, a substituted or unsubstituted phenyl group, a substituted or unsubstituted phenylalkyl group, having up to four carbon atoms in the alkyl moiety, or any two of $R^5$, $R^6$, $R^7$ or $R^8$ can be taken together to form with the nitrogen atom a 5- or 6-membered heterocyclic ring, optionally having up to one additional hetero atom (e.g., oxygen, nitrogen, or sulfur) in the ring, and preferably saturated, such as piperidino, morpholino, pyrrolidino, piperazino or the like, or any three of $R^5$, $R^6$, $R^7$ or $R^8$ can be taken together to form with the nitrogen atom a 5- or 6-membered aromatic heterocyclic ring, such as piperazole or pyridine. When the ammonium group contains a substituted phenyl or substituted phenylalkyl group, the substituents will generally be selected from halogen atoms, ($C_1$-$C_8$)alkyl groups, ($C_1$-$C_4$)alkoxy groups, hydroxy group, nitro groups, trifluoromethyl groups, cyano groups, amino groups, ($C_1$-$C_4$)alkylthio groups, and the like. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methylbenzylammonium, n-hexylammonium, triethylammonium, trimethylammonium, tri(n-butyl)-ammonium, methoxyethylammonium, diisopropylammonium, pyridinium, dialkylammonium, pyrazolium, propargylammonium, dimethylhydrazinium, octadecylammonium, 4-dichlorophenylammonium, 4-nitrobenzylammonium, benzyltrimethylammonium, 2-hydroxyethyldimethyloctadecylammonium, 2-hydroxyethyldiethyloctylammonium, decyltrimethylammonium, hexyltriethylammonium, 4-methylbenzyltrimethylammonium, and the like. Among the acid addition salts are those in which the anion is an agronomically acceptable anion such as hydrochloride, hydrobromide, sulfate, nitrate, perchlorate, acetate, oxalate or the like.

Representative examples of the compounds of the invention embraced by Formula I are listed below.

Those examples listed under Group A include compounds where Y is a Group A substituent as defined above for Formula I. Those examples listed under Group B include compounds where Y is a Group B substituent as defined above for Formula I.

GROUP A

N,3,4-tris-(4-chlorophenyl)-4-methyl-4,5-dihydro-1H-pyrazole-1-carboxamide
N,3,4-tris-(4-chlorophenyl)-N,4-dimethyl-4,5-dihydro-1H-pyrazole-1-carboxamide
N,3-bis-(4-bromophenyl)-4-carbomethoxy-4-methyl-4,5-dihydro-1H-pyrazole-1-carboxamide
N,3-bis-(4-chlorophenyl)-4-(1-ethylpropyl)-4-methyl-4,5-dihydro-1H-pyrazole-1-carboxamide
N,3-bis-(4-chlorophenyl)-4-(1-hydroxy-1-(4-fluorophenyl)-methyl)-4-methyl-4,5-dihydro-1H-pyrazole-1-carboxamide
N,3-bis-(4-chlorophenyl)-4-(1-hydroxyethyl)-4-methyl-4,5-dihydro-1H-pyrazole-1-carboxamide
N,3-bis-(4-chlorophenyl)-4-(1-methylethyl)-4-methyl-4,5-dihydro-1H-pyrazole-1-carboxamide
N,3-bis-(4-chlorophenyl)-4-(1-methylpropyl)-4-methyl-4,5-dihydro-1H-pyrazole-1-carboxamide
N,3-bis-(4-chlorophenyl)-4-(2,3-dibromopropyl)-4-methyl-4,5-dihydro-1H-pyrazole-1-carboxamide
N,3-bis-(4-chlorophenyl)-4-(2,3-dichloropropyl)-4-methyl-4,5-dihydro-1H-pyrazole-1-carboxamide
N,3-bis-(4-chlorophenyl)-4-(2-acetoxyethyl)-4-methyl-4,5-dihydro-1H-pyrazole-1-carboxamide
N,3-bis-(4-chlorophenyl)-4-(2-ethylthioethyl)-4-methyl-4,5-dihydro-1H-pyrazole-1-carboxamide
N,3-bis-(4-chlorophenyl)-4-(2-hydroxyethyl)-4-methyl-4,5-dihydro-1H-pyrazole-1-carboxamide
N,3-bis-(4-chlorophenyl)-4-(2-hydroxypropyl)-4-methyl-4,5-dihydro-1H-pyrazole-1-carboxamide
N,3-bis-(4-chlorophenyl)-4-(2-methoxyethoxymethyl)-4-methyl-4,5-dihydro-1H-pyrazole-1-carboxamide
N,3-bis-(4-chlorophenyl)-4-(2-methoxyethyl)-4-methyl-4,5-dihydro-1H-pyrazole-1-carboxamide
N,3-bis-(4-chlorophenyl)-4-(2-methylpropyl)-4-methyl-4,5-dihydro-1H-pyrazole-1-carboxamide
N,3-bis-(4-chlorophenyl)-4-(2-methylpropyl)-N,4-dimethyl-4,5-dihydro-1H-pyrazole-1-carboxamide
N,3-bis-(4-chlorophenyl)-4-(2-methylsulfonylethyl)-4-methyl-4,5-dihydro-1H-pyrazole-1-carboxamide
N,3-bis-(4-chlorophenyl)-4-(2-methylsulfoxylethyl)-4-methyl-4,5-dihydro-1H-pyrazole-1-carboxamide
N,3-bis-(4-chlorophenyl)-4-(2-methylthioethyl)-4-methyl-4,5-dihydro-1H-pyrazole-1-carboxamide
N,3-bis-(4-chlorophenyl)-4-(2-phenylthioethyl)-4-methyl-4,5-dihydro-1H-pyrazole-1-carboxamide
N,3-bis-(4-chlorophenyl)-4-(3-azidopropyl)-4-methyl-4,5-dihydro-1H-pyrazole-1-carboxamide
N,3-bis-(4-chlorophenyl)-4-(3-butenyl)-4-methyl-4,5-dihydro-1H-pyrazole-1-carboxamide
N,3-bis-(4-chlorophenyl)-4-(3-chloropropyl)-4-methyl-4,5-dihydro-1H-pyrazole-1-carboxamide
N,3-bis-(4-chlorophenyl)-4-(3-cyanopropyl)-4-methyl-4,5-dihydro-1H-pyrazole-1-carboxamide
N,3-bis-(4-chlorophenyl)-4-(4-chlorobenzoyl)-4-methyl-4,5-dihydro-1H-pyrazole-1-carboxamide
N,3-bis-(4-chlorophenyl)-4-(4-chlorobutyl)-4-methyl-4,5-dihydro-1H-pyrazole-1-carboxamide
N,3-bis-(4-chlorophenyl)-4-(4-methoxybutyl)-4-methyl-4,5-dihydro-1H-pyrazole-1-carboxamide
N,3-bis-(4-chlorophenyl)-4-(5-hexenyl)-4-methyl-4,5-dihydro-1H-pyrazole-1-carboxamide
N,3-bis-(4-chlorophenyl)-4-acetyl-4-methyl-4,5-dihydro-1H-pyrazole-1-carboxamide
N,3-bis-(4-chlorophenyl)-4-allyl-4-methyl-4,5-dihydro-1H-pyrazole-1-carboxamide
N,3-bis-(4-chlorophenyl)-4-benzoyl-4-methyl-4,5-dihydro-1H-pyrazole-1-carboxamide
N,3-bis-(4-chlorophenyl)-4-benzyl-4-methyl-4,5-dihydro-1H-pyrazole-1-carboxamide
N,3-bis-(4-chlorophenyl)-4-butyl-4-methyl-4,5-dihydro-1H-pyrazole-1-carboxamide
N,3-bis-(4-chlorophenyl)-4-butyl-N,4-dimethyl-4,5-dihydro-1H-pyrazole-1-carboxamide
N,3-bis-(4-chlorophenyl)-4-carbo(2-dimethylaminoethoxy)-4-methyl-4,5-dihydro-1H-pyrazole-1-carboxamide
N,3-bis-(4-chlorophenyl)-4-carbo(2-dimethylaminoethoxy)-4-methyl-4,5-dihydro-1H-pyrazole-1-carboxamide hydrochloride salt
N,3-bis-(4-chlorophenyl)-4-carbo(2-methylsulfonylethoxy)-4-methyl-4,5-dihydro-1H-pyrazole-1-carboxamide
N,3-bis-(4-chlorophenyl)-4-carbo(2-methylthioethoxy)-4-methyl-4,5-dihydro-1H-pyrazole-1-carboxamide
N,3-bis-(4-chlorophenyl)-4-carbobutoxy-4-methyl-4,5-dihydro-1H-pyrazole-1-carboxamide
N,3-bis-(4-chlorophenyl)-4-carboethoxy-4-methyl-4,5-dihydro-1H-pyrazole-1-carboxamide
N,3-bis-(4-chlorophenyl)-4-carboisopropoxy-4-methyl-4,5-dihydro-1H-pyrazole-1-carboxamide
N,3-bis-(4-chlorophenyl)-4-carbomenthyloxy-4-methyl-4,5-dihydro-1H-pyrazole-1-carboxamide
N,3-bis-(4-chlorophenyl)-4-carbomethoxy-4-ethyl-4,5-dihydro-1H-pyrazole-1-carboxamide
N,3-bis-(4-chlorophenyl)-4-carbomethoxy-4-methyl-4,5-dihydro-1H-pyrazole-1-carboxamide
N,3-bis-(4-chlorophenyl)-4-carbomethoxy-4-methyl-N-acetyl-4,5-dihydro-1H-pyrazole-1-carboxamide
N,3-bis-(4-chlorophenyl)-4-carbomethoxy-N,4-dimethyl-4,5-dihydro-1H-pyrazole-1-carboxamide
N,3-bis-(4-chlorophenyl)-4-carbomethoxy-N-(1-carbomethoxy-prop-2-yl-thio)-4-methyl-4,5-dihydro-1H-pyrazole-1-carboxamide
N,3-bis-(4-chlorophenyl)-4-carbomethoxy-N-(2-nitrophenylsulfenyl)-4-methyl-4,5-dihydro-1H-pyrazole-1-carboxamide
N,3-bis-(4-chlorophenyl)-4-carbomethoxy-N-(3-cyanopropylthio)-4-methyl-4,5-dihydro-1H-pyrazole-1-carboxamide
N,3-bis-(4-chlorophenyl)-4-carbomethoxy-N-acetyl-4-methyl-4,5-dihydro-1H-pyrazole-1-carbxthioamide
N,3-bis-(4-chlorophenyl)-4-carbomethoxy-N-carboethoxy-4-methyl-4,5-dihydro-1H-pyrazole-1-carboxamide
N,3-bis-(4-chlorophenyl)-4-carbomethoxy-N-carbomethoxythio-4-methyl-4,5-dihydro-1H-pyrazole-1-carboxamide
N,3-bis-(4-chlorophenyl)-4-carbomethoxy-N-carbophenoxy-4-methyl-4,5-dihydro-1H-pyrazole-1-carboxamide
N,3-bis-(4-chlorophenyl)-4-carbomethoxy-N-carbovinyloxy-4-methyl-4,5-dihydro-1H-pyrazole-1-carboxamide
N,3-bis-(4-chlorophenyl)-4-carbomethoxy-N-dimethylcarbamoyl-4-methyl-4,5-dihydro-1H-pyrazole-1-carboxamide
N,3-bis-(4-chlorophenyl)-4-carbomethoxy-N-formyl-4-methyl-4,5-dihydro-1H-pyrazole-1-carboxamide
N,3-bis-(4-chlorophenyl)-4-carbomethoxy-N-methoxymethyl-4-methyl-4,5-dihydro-1H-pyrazole-1-carboxamide N,3-bis-(4-chlorophenyl)-4-carbomethoxy-N-methyloxallyl-4-methyl-4,5-dihydro-1H-pyrazole-1-carboxamide N,3-bis-(4-chlorophenyl)-4-carbomethoxy-N-methylthio-4-methyl-4,5-dihydro-1H-pyrazole-1-carboxamide N,3-bis-(4-chlorophenyl)-4-carbomethoxy-N-phenylthio-4-methyl-4,5-dihydro-1H-pyrazole-1-carboxamide N,3-bis-(4-chlorophenyl)-4-carbomethoxy-N-propylthio-4-methyl-4,5-dihydro-1H-pyrazole-1-carboxamide N,3-bis-(4-chlorophenyl)-4-carbomethoxy-N-trifluoroacetyl-4-methyl-4,5-dihydro-1H-pyrazole-1-carboxamide N,3-bis-(4-chlorophenyl)-4-carbomethoxymethyl-4-methyl-4,5-dihydro-1H-pyrazole-1-carboxamide N,3-bis-(4-chlorophenyl)-4-carbomethylthiomethoxy-4-methyl-4,5-dihydro-1H-pyrazole-1-carboxamide N,3-bis-(4-chlorophenyl)-4-carbopropoxy-4-methyl-4,5-dihydro-1H-pyrazole-1-carboxamide N,3-bis-(4-chlorophenyl)-4-carboxy-4-methyl-4,5-dihydro-1H-pyrazole-1-carboxamide N,3-bis-(4-chlorophenyl)-4-carboxy-4-methyl-4,5-dihydro-1H-pyrazole-1-carboxamide sodium salt N,3-bis-(4-chlorophenyl)-4-cyano-4-methyl-4,5-dihydro-1H-pyrazole-1-carboxamide N,3-bis-(4-chlorophenyl)-4-cyclohexyl-4-methyl-4,5-dihydro-1H-pyrazole-1-carboxamide N,3-bis-(4-chlorophenyl)-4-diethylcarboxamido-4-methyl-4,5-dihydro-1H-pyrazole-1-carboxamide N,3-bis-(4-chlorophenyl)-4-dimethylcarboxamido-4-methyl-4,5-dihydro-1H-pyrazole-1-carboxamide N,3-bis-(4-chlorophenyl)-4-dimethylthiocarbamoyl-4-methyl-4,5-dihydro-1H-pyrazole-1-carboxamide N,3-bis-(4-chlorophenyl)-4-ethyl-4-methyl-4,5-dihydro-1H-pyrazole-1-carboxamide N,3-bis-(4-chlorophenyl)-4-hexyl-4-methyl-4,5-dihydro-1H-pyrazole-1-carboxamide N,3-bis-(4-chlorophenyl)-4-isobutyryl-4-methyl-4,5-dihydro-1H-pyrazole-1-carboxamide N,3-bis-(4-chlorophenyl)-4-methoxymethyl-4-methyl-4,5-dihydro-1H-pyrazole-1-carboxamide N,3-bis-(4-chlorophenyl)-4-methylthiomethyl-4-methyl-4,5-dihydro-1H-pyrazole-1-carboxamide N,3-bis-(4-chlorophenyl)-4-methylthiothiocarbonyl-4-methyl-4,5-dihydro-1H-pyrazole-1-carboxamide N,3-bis-(4-chlorophenyl)-4-pentyl-4-methyl-4,5-dihydro-1H-pyrazole-1-carboxamide N,3-bis-(4-chlorophenyl)-4-phenyl-4-methyl-4,5-dihydro-1H-pyrazole-1-carboxamide N,3-bis-(4-chlorophenyl)-4-phenyl-N,4-dimethyl-4,5-dihydro-1H-pyrazole-1-carboxamide N,3-bis-(4-chlorophenyl)-4-phenyl-N-acetyl-4-methyl-4,5-dihydro-1H-pyrazole-1-carboxamide N,3-bis-(4-chlorophenyl)-4-phenyl-N-benzoyl-4-methyl-4,5-dihydro-1H-pyrazole-1-carboxamide N,3-bis-(4-chlorophenyl)-4-phenyl-N-carbomethoxy-4-methyl-4,5-dihydro-1H-pyrazole-1-carboxamide N,3-bis-(4-chlorophenyl)-4-phenyl-N-carbomethoxythio-4-methyl-4,5-dihydro-1H-pyrazole-1-carboxamide N,3-bis-(4-chlorophenyl)-4-phenyl-N-cyano-4-methyl-4,5-dihydro-1H-pyrazole-1-carboxamide N,3-bis-(4-chlorophenyl)-4-phenyl-N-methoxymethyl-4-methyl-4,5-dihydro-1H-pyrazole-1-carboxamide N,3-bis-(4-chlorophenyl)-4-phenyl-N-propionyl-4-methyl-4,5-dihydro-1H-pyrazole-1-carboxamide N,3-bis-(4-chlorophenyl)-4-phenyl-N-trimethylacetyl-4-methyl-4,5-dihydro-1H-pyrazole-1-carboxamide N,3-bis-(4-chlorophenyl)-4-pivaloyl-4-methyl-4,5-dihydro-1H-pyrazole-1-carboxamide N,3-bis-(4-chlorophenyl)-4-propionyl-4-methyl-4,5-dihydro-1H-pyrazole-1-carboxamide N,3-bis-(4-chlorophenyl)-4-propyl-4-methyl-4,5-dihydro-1H-pyrazole-1-carboxamide N,3-bis-(4-dichlorophenyl)-4-phenyl-4-methyl-4,5-dihydro-1H-pyrazole-1-carboxamide N,3-bis-(4-fluorophenyl)-4-butyl-4-methyl-4,5-dihydro-1H-pyrazole-1-carboxamide N,3-bis-(4-trifluoromethylphenyl)-4-carbomethoxy-4-methyl-4,5-dihydro-1H-pyrazole-1-carboxamide N-(1-naphthyl)-3-(4-chlorophenyl)-4-carbomethoxy-4,5-dihydro-1H-pyrazole-1-carboxamide N-(2,4-dinitrophenyl)-3-(4-chlorophenyl)-4-carbomethoxy-4,5-dihydro-1H-pyrazole-1-carboxamide N-(2-fluoro-4-trifluoromethylphenyl)-3-(3-chloro-4-trifluoromethylphenyl)-4-(3-methylthiopropyl)-4-methyl-4,5-dihydro-1H-pyrazole-1-carboxamide N-(2-fluoro-4-trifluoromethylphenyl)-3-(3-chloro-4-trifluoromethylphenyl)-4-carboethoxy-4-methyl-4,5-dihydro-1H-pyrazole-1-carboxamide N-(2-fluoro-4-trifluoromethylphenyl)-3-(3-chloro-4-trifluoromethylphenyl)-4-phenyl-4-methyl-4,5-dihydro-1H-pyrazole-1-carboxamide N-(2-fluoro-4-trifluoromethylphenyl)-3-(4-chlorophenyl)-4-(3-methylthiopropyl)-4-methyl-4,5-dihydro-1H-pyrazole-1-carboxamide N-(2-fluoro-4-trifluoromethylphenyl)-3-(4-chlorophenyl)-4-carboethoxy-4-methyl-4,5-dihydro-1H-pyrazole-1-carboxamide N-(2-fluoro-4-trifluoromethylphenyl)-3-(4-chlorophenyl)-4-phenyl-4-methyl-4,5-dihydro-1H-pyrazole-1-carboxamide N-(2-methyl-4-trifluoromethylphenyl)-3-(3-chloro-4-trifluoromethylphenyl)-4-(3-methylthiopropyl)-4-methyl-4,5-dihydro-1H-pyrazole-1-carboxamide N-(2-methyl-4-trifluoromethylphenyl)-3-(3-chloro-4-trifluoromethylphenyl)-4-carboethoxy-4-methyl-4,5-dihydro-1H-pyrazole-1-carboxamide N-(2-methyl-4-trifluoromethylphenyl)-3-(3-chloro-4-trifluoromethylphenyl)-4-phenyl-4-methyl-4,5-dihydro-1H-pyrazole-1-carboxamide N-(2-methyl-4-trifluoromethylphenyl)-3-(4-chlorophenyl)-4-(3-methylthiopropyl)-4-methyl-4,5-dihydro-1H-pyrazole-1-carboxamide N-(2-methyl-4-trifluoromethylphenyl)-3-(4-chlorophenyl)-4-carboethoxy-4-methyl-4,5-dihydro-1H-pyrazole-1-carboxamide N-(2-methyl-4-trifluoromethylphenyl)-3-(4-chlorophenyl)-4-phenyl-4-methyl-4,5-dihydro-1H-pyrazole-1-carboxamide N-(3,4-dichlorophenyl)-3-(4-chlorophenyl)-4-carbomethoxy-4-methyl-4,5-dihydro-1H-pyrazole-1-carboxamide N-(3,4-dichlorophenyl)-3-(4-chlorophenyl)-4-phenyl-4-methyl-4,5-dihydro-1H-pyrazole-1-carboxamide N-(3,4-dichlorophenyl)-3-phenyl-4-carbomethoxy-4-methyl-4,5-dihydro-1H-pyrazole-1-carboxamide N-(3-bromo-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-bromo-4-trifluoromethylphenyl)-3-(3-chloro-4-trifluoromethylphenyl)-4-carboethoxy-4-methyl-4,5-dihydro-1H-pyrazole-1-carboxamide N-(3-bromo-4-trifluoromethylphenyl)-3-(3-chloro-4-trifluoromethylphenyl)-4-phenyl-4-methyl-4,5-dihydro-1H-pyrazole-1-carboxamide N-(3-bromo-4-trifluoromethylphenyl)-3-(4-chlorophenyl)-4-(3-methylthiopropyl)-4-methyl-4,5-dihydro-1H-pyrazole-1-carboxamide N-(3-bromo-4-trifluoromethylphenyl)-3-(4-chlorophenyl)-4-carboethoxy-4-methyl-4,5-dihydro-1H-pyrazole-1-carboxamide N-(3-bromo-4-trifluoromethylphenyl)-3-(4-chlorophenyl)-4-phenyl-4-methyl-4,5-dihydro-1H-pyrazole-1-carboxamide N-(3-bromophenyl)-3-(3-chloro-4-trifluoromethylphenyl)-4-(3-methylthiopropyl)-4-methyl-4,5-dihydro-1H-pyrazole-1-carboxamide N-(3-bromophenyl)-3-(3-chloro-4-trifluoromethylphenyl)-4-carboethoxy-4-methyl-4,5-dihydro-1H-pyrazole-1-carboxamide N-(3-bromophenyl)-3-(3-chloro-4-trifluoromethylphenyl)-4-phenyl-4-methyl-4,5-dihydro-1H-pyrazole-1-carboxamide N-(3-bromophenyl)-3-(4-chlorophenyl)-4-(3-methylthiopropyl)-4-methyl-4,5-dihydro-1H-pyrazole-1-carboxamide N-(3-bromophenyl)-3-(4-chlorophenyl)-4-carboethoxy-4-methyl-4,5-dihydro-1H-pyrazole-1-carboxamide N-(3-bromophenyl)-3-(4-chlorophenyl)-4-phenyl-4-methyl-4,5-dihydro-1H-pyrazole-1-carboxamide N-(3-carboethoxyphenyl)-3-(3-chloro-4-trifluoromethylphenyl)-4-(3-methylthiopropyl)-4-methyl-4,5-dihydro-1H-pyrazole-1-carboxamide N-(3-carboethoxyphenyl)-3-(3-chloro-4-trifluoromethylphenyl)-4-carboethoxy-4-methyl-4,5-dihydro-1H-pyrazole-1-carboxamide N-(3-carboethoxyphenyl)-3-(3-chloro-4-trifluoromethylphenyl)-4-phenyl-4-methyl-4,5-dihydro-1H-pyrazole-1-carboxamide N-(3-carboethoxyphenyl)-3-(4-chlorophenyl)-4-(3-methylthiopropyl)-4-methyl-4,5-dihydro-1H-pyrazole-1-carboxamide N-(3-carboethoxyphenyl)-3-(4-chlorophenyl)-4-carboethoxy-4-methyl-4,5-dihydro-1H-pyrazole-1-carboxamide N-(3-carboethoxyphenyl)-3-(4-chlorophenyl)-4-phenyl-4-methyl-4,5-dihydro-1H-pyrazole-1-carboxamide N-(3-carboisopropoxyphenyl)-3-(3-chloro-4-trifluoromethylphenyl)-4-(3-methylthiopropyl)-4-methyl-4,5-dihydro-1H-pyrazole-1-carboxamide N-(3-carboisopropoxyphenyl)-3-(3-chloro-4-trifluoromethylphenyl)-4-carboethoxy-4-methyl-4,5-dihydro-1H-pyrazole-1-carboxamide N-(3-carboisopropoxyphenyl)-3-(3-chloro-4-trifluoromethylphenyl)-4-phenyl-4-methyl-4,5-dihydro-1H-pyrazole-1-carboxamide N-(3-carboisopropoxyphenyl)-3-(4-chlorophenyl)-4-(3-methylthiopropyl)-4-methyl-4,5-dihydro-1H-pyrazole-1-carboxamide N-(3-carboisopropoxyphenyl)-3-(4-chlorophenyl)-4-carboethoxy-4-methyl-4,5-dihydro-1H-pyrazole-1-carboxamide N-(3-carboisopropoxyphenyl)-3-(4-chlorophenyl)-4-phenyl-4-methyl-4,5-dihydro-1H-pyrazole-1-carboxamide N-(3-carbomethoxyphenyl)-3-(3-chloro-4-trifluoromethylphenyl)-4-(3-methylthiopropyl)-4-methyl-4,5-dihydro-1H-pyrazole-1-carboxamide N-(3-carbomethoxyphenyl)-3-(3-chloro-4-trifluoromethylphenyl)-4-carboethoxy-4-methyl-4,5-dihydro-1H-pyrazole-1-carboxamide N-(3-carbomethoxyphenyl)-3-(3-chloro-4-trifluoromethylphenyl)-4-phenyl-4-methyl-4,5-dihydro-1H-pyrazole-1-carboxamide N-(3-carbomethoxyphenyl)-3-(4-chlorophenyl)-4-(3-methylthiopropyl)-4-methyl-4,5-dihydro-1H-pyrazole-1-carboxamide N-(3-carbomethoxyphenyl)-3-(4-chlorophenyl)-4-carboethoxy-4-methyl-4,5-dihydro-1H-pyrazole-1-carboxamide N-(3-carbomethoxyphenyl)-3-(4-chlorophenyl)-4-phenyl-4-methyl-4,5-dihydro-1H-pyrazole-1-carboxamide N-(3-chloro-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-chloro-4-trifluoromethylphenyl)-3-(3-chloro-4-trifluoromethylphenyl)-4-carboethoxy-4-methyl-4,5-dihydro-1H-pyrazole-1-carboxamide N-(3-chloro-4-trifluoromethylphenyl)-3-(3-chloro-4-trifluoromethylphenyl)-4-phenyl-4-methyl-4,5-dihydro-1H-pyrazole-1-carboxamide N-(3-chloro-4-trifluoromethylphenyl)-3-(4-chlorophenyl)-4-(3-methylthiopropyl)-4-methyl-4,5-dihydro-1H-pyrazole-1-carboxamide N-(3-chloro-4-trifluoromethylphenyl)-3-(4-chlorophenyl)-4-carboethoxy-4-methyl-4,5-dihydro-1H-pyrazole-1-carboxamide N-(3-chloro-4-trifluoromethylphenyl)-3-(4-chlorophenyl)-4-phenyl-4-methyl-4,5-dihydro-1H-pyrazole-1-carboxamide N-(3-chlorophenyl)-3-(4-chlorophenyl)-4-carbomethoxy-4-methyl-4,5-dihydro-1H-pyrazole-1-carboxamide N-(3-chlorophenyl)-3-(4-chlorophenyl)-4-phenyl-4-methyl-4,5-dihydro-1H-pyrazole-1-carboxamide N-(3-cyano-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-cyano-4-trifluoromethylphenyl)-3-(3-chloro-4-trifluoromethylphenyl)-4-carboethoxy-4-methyl-4,5-dihydro-1H-pyrazole-1-carboxamide N-(3-cyano-4-trifluoromethylphenyl)-3-(3-chloro-4-trifluoromethylphenyl)-4-phenyl-4-methyl-4,5-dihydro-1H-pyrazole-1-carboxamide N-(3-cyano-4-trifluoromethylphenyl)-3-(4-chlorophenyl)-4-(3-methylthiopropyl)-4-methyl-4,5-dihydro-1H-pyrazole-1-carboxamide N-(3-cyano-4-trifluoromethylphenyl)-3-(4-chlorophenyl)-4-carboethoxy-4-methyl-4,5-dihydro-1H-pyrazole-1-carboxamide N-(3-cyano-4-trifluoromethylphenyl)-3-(4-chlorophenyl)-4-phenyl-4-methyl-4,5-dihydro-1H-pyrazole-1-carboxamide N-(3-difluoromethoxy-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-difluoromethoxy-4-trifluoromethylphenyl)-3-(3-chloro-4-trifluoromethylphenyl)-4-carboethoxy-4-methyl-4,5-dihydro-1H-pyrazole-1-carboxamide N-(3-difluoromethoxy-4-trifluoromethylphenyl)-3-(3-chloro-4-trifluoromethylphenyl)-4-phenyl-4-methyl-4,5-dihydro-1H-pyrazole-1-carboxamide N-(3-difluoromethoxy-4-trifluoromethylphenyl)-3-(4-chlorophenyl)-4-(3-methylthiopropyl)-4-methyl-4,5-dihydro-1H-pyrazole-1-carboxamide N-(3-difluoromethoxy-4-trifluoromethylphenyl)-3-(4-chlorophenyl)-4-carboethoxy-4-methyl-4,5-dihydro-1H-pyrazole-1-carboxamide N-(3-difluoromethoxy-4-trifluoromethylphenyl)-3-(4-chlorophenyl)-4-phenyl-4-methyl-4,5-dihydro-1H-pyrazole-1-carboxamide N-(3-difluoromethoxyphenyl)-3-(3-chloro-4-trifluoromethylphenyl)-4-(3-methylthiopropyl)-4-methyl-4,5-dihydro-1H-pyrazole-1-carboxamide N-(3-difluoromethoxyphenyl)-3-(3-chloro-4-trifluoromethylphenyl)-4-carboethoxy-4-methyl-4,5-dihydro-1H-pyrazole-1-carboxamide N-(3-difluoromethoxyphenyl)-3-(3-chloro-4-trifluoromethylphenyl)-4-phenyl-4-methyl-4,5-dihydro-1H-pyrazole-1-carboxamide N-(3-difluoromethoxyphenyl)-3-(4-chlorophenyl)-4-(3-methylthiopropyl)-4-methyl-4,5-dihydro-1H-pyrazole-1-carboxamide N-(3-difluoromethoxyphenyl)-3-(4-chlorophenyl)-4-carboethoxy-4-methyl-4,5-dihydro-1H-pyrazole-1-carboxamide N-(3-difluoromethoxyphenyl)-3-(4-chlorophenyl)-4-phenyl-4-methyl-4,5-dihydro-1H-pyrazole-1-carboxamide N-(3-dimethylsulfonamidophenyl)-3-(3-chloro-4-trifluoromethylphenyl)-4-(3-methylthiopropyl)-4-methyl-4,5-dihydro-1H-pyrazole-1-carboxamide N-(3-dimethylsulfonamidophenyl)-3-(3-chloro-4-trifluoromethylphenyl)-4-carboethoxy-4-methyl-4,5-dihydro-1H-pyrazole-1-carboxamide N-(3-dimethylsulfonamidophenyl)-3-(3-chloro-4-trifluoromethylphenyl)-4-phenyl-4-methyl-4,5-dihydro-1H-pyrazole-1-carboxamide N-(3-dimethylsulfonamidophenyl)-3-(4-chlorophenyl)-4-(3-methylthiopropyl)-4-methyl-4,5-dihydro-1H-pyrazole-1-carboxamide N-(3-dimethylsulfonamidophenyl)-3-(4-chlorophenyl)-4-carboethoxy-4-methyl-4,5-dihydro-1H-pyrazole-1-carboxamide N-(3-dimethylsulfonamidophenyl)-3-(4-chlorophenyl)-4-phenyl-4-methyl-4,5-dihydro-1H-pyrazole-1-carboxamide N-(3-fluoro-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-fluoro-4-trifluoromethylphenyl)-3-(3-chloro-4-trifluoromethylphenyl)-4-carboethoxy-4-methyl-4,5-dihydro-1H-pyrazole-1-carboxamide N-(3-fluoro-4-trifluoromethylphenyl)-3-(3-chloro-4-trifluoromethylphenyl)-4-phenyl-4-methyl-4,5-dihydro-1H-pyrazole-1-carboxamide N-(3-fluoro-4-trifluoromethylphenyl)-3-(4-chlorophenyl)-4-(3-methylthiopropyl)-4-methyl-4,5-dihydro-1H-pyrazole-1-carboxamide N-(3-fluoro-4-trifluoromethylphenyl)-3-(4-chlorophenyl)-4-carboethoxy-4-methyl-4,5-dihydroxy-1H-pyrazole-1-carboxamide N-(3-fluoro-4-trifluoromethylphenyl)-3-(4-chlorophenyl)-4-phenyl-4-methyl-4,5-dihydro-1H-pyrazole-1-carboxamide N-(3-methoxy-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-methoxy-4-trifluoromethylphenyl)-3-(3-chloro-4-trifluoromethylphenyl)-4-carboethoxy-4-methyl-4,5-dihydro-1H-pyrazole-1-carboxamide N-(3-methoxy-4-trifluoromethylphenyl)-3-(3-chloro-4-trifluoromethylphenyl)-4-phenyl-4-methyl-4,5-dihydro-1H-pyrazole-1-carboxamide N-(3-methoxy-4-trifluoromethylphenyl)-3-(4-chlorophenyl)-4-(3-methylthiopropyl)-4-methyl-4,5-dihydro-1H-pyrazole-1-carboxamide N-(3-methoxy-4-trifluoromethylphenyl)-3-(4-chlorophenyl)-4-carboethoxy-4-methyl-4,5-dihydro-1H-pyrazole-1-carboxamide N-(3-methoxy-4-trifluoromethylphenyl)-3-(4-chlorophenyl)-4-phenyl-4-methyl-4,5-dihydro-1H-pyrazole-1-carboxamide N-(3-methyl-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-methyl-4-trifluoromethylphenyl)-3-(3-chloro-4-trifluoromethylphenyl)-4-carboethoxy-4-methyl-4,5-dihydro-1H-pyrazole-1-carboxamide N-(3-methyl-4-trifluoromethylphenyl)-3-(3-chloro-4-trifluoromethylphenyl)-4-phenyl-4-methyl-4,5-dihydro-1H-pyrazole-1-carboxamide N-(3-methyl-4-trifluoromethylphenyl)-3-(4-chlorophenyl)-4-(3-methylthiopropyl)-4-methyl-4,5-dihydro-1H-pyrazole-1-carboxamide N-(3-methyl-4-trifluoromethylphenyl)-3-(4-chlorophenyl)-4-carboethoxy-4-methyl-4,5-dihydro-1H-pyrazole-1-carboxamide N-(3-methyl-4-trifluoromethylphenyl)-3-(4-chlorophenyl)-4-phenyl-4-methyl-4,5-dihydro-1H-pyrazole-1-carboxamide N-(3-methylsulfonyl-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-methylsulfonyl-4-trifluoromethylphenyl)-3-(3-chloro-4-trifluoromethylphenyl)-4-carboethoxy-4-methyl-4,5-dihydro-1H-pyrazole-1-carboxamide N-(3-methylsulfonyl-4-trifluoromethylphenyl)-3-(3-chloro-4-trifluoromethylphenyl)-4-phenyl-4-methyl-4,5-dihydro-1H-pyrazole-1-carboxamide N-(3-methylsulfonyl-4-trifluoromethylphenyl)-3-(4-chlorophenyl)-4-(3-methylthiopropyl)-4-methyl-4,5-dihydro-1H-pyrazole-1-carboxamide N-(3-methylsulfonyl-4-trifluoromethylphenyl)-3-(4-chlorophenyl)-4-carboethoxy-4-methyl-4,5-dihydro-1H-pyrazole-1-carboxamide N-(3-methylsulfonyl-4-trifluoromethylphenyl)-3-(4-chlorophenyl)-4-phenyl-4-methyl-4,5-dihydro-1H-pyrazole-1-carboxamide N-(3-methylsulfonylphenyl)-3-(3-chloro-4-trifluoromethylphenyl)-4-(3-methylthiopropyl)-4-methyl-4,5-dihydro-1H-pyrazole-1-carboxamide N-(3-methylsulfonylphenyl)-3-(3-chloro-4-trifluoromethylphenyl)-4-carboethoxy-4-methyl-4,5-dihydro-1H-pyrazole-1-carboxamide N-(3-methylsulfonylphenyl)-3-(3-chloro-4-trifluoromethylphenyl)-4-phenyl-4-methyl-4,5-dihydro-1H-pyrazole-1-carboxamide N-(3-methylsulfonylphenyl)-3-(4-chlorophenyl)-4-(3-methylthiopropyl)-4-methyl-4,5-dihydro-1H-pyrazole-1-carboxamide N-(3-methylsulfonylphenyl)-3-(4-chlorophenyl)-4-carboethoxy-4-methyl-4,5-dihydro-1H-pyrazole-1-carboxamide N-(3-methylsulfonylphenyl)-3-(4-chlorophenyl)-4-carbomethoxy-4-methyl-4,5-dihydro-1H-pyrazole-1-carboxamide N-(3-methylsulfonylphenyl)-3-(4-chlorophenyl)-4-phenyl-4-methyl-4,5-dihydro-1H-pyrazole-1-carboxamide N-(3-methylthio-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-methylthio-4-trifluoromethylphenyl)-3-(3-chloro-4-trifluoromethylphenyl)-4-carboethoxy-4-methyl-4,5-dihydro-1H-pyrazole-1-carboxamide N-(3-methylthio-4-trifluoromethylphenyl)-3-(3-chloro-4-trifluoromethylphenyl)-4-phenyl-4-methyl-4,5-dihydro-1H-pyrazole-1-carboxamide N-(3-methylthio-4-trifluoromethylphenyl)-3-(4-chlorophenyl)-4-(3-methylthiopropyl)-4-methyl-4,5-dihydro-1H-pyrazole-1-carboxamide N-(3-methylthio-4-trifluoromethylphenyl)-3-(4-chlorophenyl)-4-carboethoxy-4-methyl-4,5-dihydro-1H-pyrazole-1-carboxamide N-(3-methylthio-4-trifluoromethylphenyl)-3-(4-chlorophenyl)-4-phenyl-4-methyl-4,5-dihydro-1H-pyrazole-1-carboxamide N-(3-methylthiophenyl)-3-(3-chloro-4-trifluoromethylphenyl)-4-(3-methylthiopropyl)-4-methyl-4,5-dihydro-1H-pyrazole-1-carboxamide N-(3-methylthiophenyl)-3-(3-chloro-4-trifluoromethylphenyl)-4-carboethoxy-4-methyl-4,5-dihydro-1H-pyrazole-1-carboxamide N-(3-methylthiophenyl)-3-(3-chloro-4-trifluoromethylphenyl)-4-phenyl-4-methyl-4,5-dihydro-1H-pyrazole-1-carboxamide N-(3-methylthiophenyl)-3-(4-chlorophenyl)-4-(3-methylthiopropyl)-4-methyl-4,5-dihydro-1H-pyrazole-1-carboxamide N-(3-methylthiophenyl)-3-(4-chlorophenyl)-4-carboethoxy-4-methyl-4,5-dihydro-1H-pyrazole-1-carboxamide N-(3-methylthiophenyl)-3-(4-chlorophenyl)-4-carbomethoxy-4-methyl-4,5-dihydro-1H-pyrazole-1-carboxamide N-(3-methylthiophenyl)-3-(4-chlorophenyl)-4-phenyl-4-methyl-4,5-dihydro-1H-pyrazole-1-carboxamide N-(3-nitro-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-nitro-4-trifluoromethylphenyl)-3-(3-chloro-4-trifluoromethylphenyl)-4-carboethoxy-4-methyl-4,5-dihydro-1H-pyrazole-1-carboxamide N-(3-nitro-4-trifluoromethylphenyl)-3-(3-chloro-4-trifluoromethylphenyl)-4-phenyl-4-methyl-4,5-dihydro-1H-pyrazole-1-carboxamide N-(3-nitro-4-trifluoromethylphenyl)-3-(4-chlorophenyl)-4-(3-methylthiopropyl)-4-methyl-4,5-dihydro-1H-pyrazole-1-carboxamide N-(3-nitro-4-trifluoromethylphenyl)-3-(4-chlorophenyl)-4-carboethoxy-4-methyl-4,5-dihydro-1H-pyrazole-1-carboxamide N-(3-nitro-4-trifluoromethylphenyl)-3-(4-chlorophenyl)-4-phenyl-4-methyl-4,5-dihydro-1H-pyrazole-1-carboxamide N-(3-trifluoromethoxy-4-trifluoromethylphenyl)-3-(3-chloro-4-trifluoromethylphenyl)-4-(3-methylthiopropyl)-4-methyl-4,5-dihydro-1H-pyrazole-1-carboxamide N-(3-trifluoromethoxy-4-trifluoromethylphenyl)-3-(3-chloro-4-trifluoromethylphenyl)-4-carboethoxy-4-methyl-4,5-dihydro-1H-pyrazole-1-carboxamide N-(3-trifluoromethoxy-4-trifluoromethylphenyl)-3-(3-chloro-4-trifluoromethylphenyl)-4-phenyl-4-methyl-4,5-dihydro-1H-pyrazole-b 1-carboxamide N-(3-trifluoromethoxy-4-trifluoromethylphenyl)-3-(4-chlorophenyl)-4-(3-methylthiopropyl)-4-methyl-4,5-dihydro-1H-pyrazole-1-carboxamide N-(3-trifluoromethoxy-4-trifluoromethylphenyl)-3-(4-chlorophenyl)-4-carboethoxy-4-methyl-4,5-dihydro-1H-pyrazole-1-carboxamide N-(3-trifluoromethoxy)-4-trifluoromethylphenyl)-3-(4-chlorophenyl)-4-phenyl-4-methyl-4,5-dihydro-1H-pyrazole-1-carboxamide N-(3-trifluoromethoxyphenyl)-3-(3-chloro-4-trifluoromethylphenyl)-4-(3-methylthiopropyl)-4-methyl-4,5-dihydro-1H-pyrazole-1-carboxamide N-(3-trifluoromethoxyphenyl)-3-(3-chloro-4-trifluoromethylphenyl)-4-carboethoxy-4-methyl-4,5-dihydro-1H-pyrazole-1-carboxamide N-(3-trifluoromethoxyphenyl)-3-(3-chloro-4-trifluoromethylphenyl)-4-phenyl-4-methyl-4,5-dihydro-1H-pyrazole-1-carboxamide N-(3-trifluoromethoxyphenyl)-3-(4-chlorophenyl)-4-(3-methylthiopropyl)-4-methyl-4,5-dihydro-1H-pyrazole-1-carboxamide N-(3-trifluoromethoxyphenyl)-3-(4-chlorophenyl)-4-carboethoxy-4-methyl-4,5-dihydro-1H-pyrazole-1-carboxamide N-(3-trifluoromethoxyphenyl)-3-(4-chlorophenyl)-4-phenyl-4-methyl-4,5-dihydro-1H-pyrazole-1-carboxamide N-(3-trifluoromethylphenyl)-3-(3-chloro-4-trifluoromethylphenyl)-4-(3-methylthiopropyl)-4-methyl-4,5-dihydro-1H-pyrazole-1-carboxamide N-(3-trifluoromethylphenyl)-3-(3-chloro-4-trifluoromethylphenyl)-4-carboethoxy-4-methyl-4,5-dihydro-1H-pyrazole-1-carboxamide N-(3-trifluoromethylphenyl)-3-(3-chloro-4-trifluoromethylphenyl)-4-phenyl-4-methyl-4,5-dihydro-1H-pyrazole-1-carboxamide N-(3-trifluoromethylphenyl)-3-(4-chlorophenyl)-4-(3-methylthiopropyl)-4-methyl-4,5-dihydro-1H-pyrazole-1-carboxamide N-(3-trifluoromethylphenyl)-3-(4-chlorophenyl)-4-carboethoxy-4-methyl-4,5-dihydro-1H-pyrazole-1-carboxamide N-(3-trifluoromethylphenyl)-3-(4-chlorophenyl)-4-carbomethoxy-4-methyl-4,5-dihydro-1H-pyrazole-1-carboxamide N-(3-trifluoromethylphenyl)-3-(4-chlorophenyl)-4-phenyl-4-methyl-4,5-dihydro-1H-pyrazole-1-carboxamide N-(4-(3-methylthiopropyl)phenyl)-3-(3-chloro-4-trifluoromethylphenyl)-4-(3-methylthiopropyl)-4-methyl-4,5-dihydro-1H-pyrazole-1-carboxamide N-(4-(3-methylthiopropyl)phenyl)-3-(4-chlorophenyl)-4-(3-methylthiopropyl)-4-methyl-4,5-dihydro-1H-pyrazole-1-carboxamide N-(4-bromophenyl)-3-(3-chloro-4-trifluoromethylphenyl)-4-(3-methylthiopropyl)-4-acetyl-4,5-dihydro-1H-pyrazole-1-carboxamide N-(4-bromophenyl)-3-(3-chloro-4-trifluoromethylphenyl)-4-(3-methylthiopropyl)-4-carbomethoxy-4,5-dihydro-1H-pyrazole-1-carboxamide N-(4-bromophenyl)-3-(3-chloro-4-trifluoromethylphenyl)-4-(3-methylthiopropyl)-4-ethyl-4,5-dihydro-1H-pyrazole-1-carboxamide
N-(4-bromophenyl)-3-(3-chloro-4-trifluoromethylphenyl)-4-(3-methylthiopropyl)-4-methyl-4,5-dihydro-1H-pyrazole-1-carboxamide
N-(4-bromophenyl)-3-(3-chloro-4-trifluoromethylphenyl)-4-(3-methylthiopropyl)-4-methyl-N-(2-methoxyethylsulfenyl)-4,5-dihydro-1H-pyrazole-1-carboxamide
N-(4-bromophenyl)-3-(3-chloro-4-trifluoromethylphenyl)-4-(3-methylthiophenyl)-4-methyl-N-(2-nitrophenylsulfenyl)-4,5-dihydro-1H-pyrazole-1-carboxamide
N-(4-bromophenyl)-3-(3-chloro-4-trifluoromethylphenyl)-4-(3-methylthiopropyl)-4-methyl-N-acetyl-4,5-dihydro-1H-pyrazole-1-carboxamide
N-(4-bromophenyl)-3-(3-chloro-4-trifluoromethylphenyl)-4-(3-methylthiopropyl)-4-methyl-N-carboethoxy-4,5-dihydro-1H-pyrazole-1-carboxamide
N-(4-bromophenyl)-3-(3-chloro-4-trifluoromethylphenyl)-4-(3-methylthiopropyl)-4-methyl-N-carbomethoxy-4,5-dihydro-1H-pyrazole-1-carboxamide
N-(4-bromophenyl)-3-(3-chloro-4-trifluoromethylphenyl)-4-(3-methylthiopropyl)-4-methyl-N-carbomethoxycarbonyl-4,5-dihydro-1H-pyrazole-1-carboxamide
N-(4-bromophenyl)-3-(3-chloro-4-trifluoromethylphenyl)-4-(3-methylthiopropyl)-4-methyl-N-carbomethoxysulfenyl-4,5-dihydro-1H-pyrazole-1-carboxamide
N-(4-bromophenyl)-3-(3-chloro-4-trifluoromethylphenyl)-4-(3-methylthiopropyl)-4-methyl-N-dimethylcarbamoyl-4,5-dihydro-1H-pyrazole-1-carboxamide
N-(4-bromophenyl)-3-(3-chloro-4-trifluoromethylphenyl)-4-(3-methylthiopropyl)-4-methyl-N-formyl-4,5-dihydro-1H-pyrazole-1-carboxamide
N-(4-bromophenyl)-3-(3-chloro-4-trifluoromethylphenyl)-4-(3-methylthiopropyl)-4-methyl-N-methoxymethyl-4,5-dihydro-1H-pyrazole-1-carboxamide
N-(4-bromophenyl)-3-(3-chloro-4-trifluoromethylphenyl)-4-(3-methylthiopropyl)-4-methyl-N-methyl-4,5-dihydro-1H-pyrazole-1-carboxamide
N-(4-bromophenyl)-3-(3-chloro-4-trifluoromethylphenyl)-4-(3-methylthiopropyl)-4-methyl-N-methylsulfenyl-4,5-dihydro-1H-pyrazole-1-carboxamide
N-(4-bromophenyl)-3-(3-chloro-4-trifluoromethylphenyl)-4-(3-methylthiopropyl)-4-methyl-N-trifluoroacetyl-4,5-dihydro-1H-pyrazole-1-carboxamide
N-(4-bromophenyl)-3-(3-chloro-4-trifluoromethylphenyl)-4-carboethoxy-4-(2-chloroallyl)-4,5-dihydro-1H-pyrazole-1-carboxamide
N-(4-bromophenyl)-3-(3-chloro-4-trifluoromethylphenyl)-4-carboethoxy-4-(2-methylthioethyl)-4,5-dihydro-1H-pyrazole-1-carboxamide
N-(4-bromophenyl)-3-(3-chloro-4-trifluoromethylphenyl)-4-carboethoxy-4-(3-cyanopropyl)-4,5-dihydro-1H-pyrazole-1-carboxamide
N-(4-bromophenyl)-3-(3-chloro-4-trifluoromethylphenyl)-4-carboethoxy-4-(4-chlorophenyl)-4,5-dihydro-1H-pyrazole-1-carboxamide
N-(4-bromophenyl)-3-(3-chloro-4-trifluoromethylphenyl)-4-carboethoxy-4-(4-difluoromethoxyphenyl)-4,5-dihydro-1H-pyrazole-1-carboxamide
N-(4-bromophenyl)-3-(3-chloro-4-trifluoromethylphenyl)-4-carboethoxy-4-(4-trifluoromethoxyphenyl)-4,5-dihydro-1H-pyrazole-1-carboxamide
N-(4-bromophenyl)-3-(3-chloro-4-trifluoromethylphenyl)-4-carboethoxy-4-(4-trifluoromethylphenyl)-4,5-dihydro-1H-pyrazole-1-carboxamide
N-(4-bromophenyl)-3-(3-chloro-4-trifluoromethylphenyl)-4-carboethoxy-4-acetyl-4,5-dihydro-1H-pyrazole-1-carboxamide
N-(4-bromophenyl)-3-(3-chloro-4-trifluoromethylphenyl)-4-carboethoxy-4-allyl-4,5-dihydro-1H-pyrazole-1-carboxamide
N-(4-bromophenyl)-3-(3-chloro-4-trifluoromethylphenyl)-4-carboethoxy-4-benzyl-4,5-dihydro-1H-pyrazole-1-carboxamide
N-(4-bromophenyl)-3-(3-chloro-4-trifluoromethylphenyl)-4-carboethoxy-4-carbomethoxy-4,5-dihydro-1H-pyrazole-1-carboxamide
N-(4-bromophenyl)-3-(3-chloro-4-trifluoromethylphenyl)-4-carboethoxy-4-ethyl-4,5-dihydro-1H-pyrazole-1-carboxamide
N-(4-bromophenyl)-3-(3-chloro-4-trifluoromethylphenyl)-4-carboethoxy-4-methallyl-4,5-dihydro-1H-pyrazole-1-carboxamide
N-(4-bromophenyl)-3-(3-chloro-4-trifluoromethylphenyl)-4-carboethoxy-4-methoxymethyl-4,5-dihydro-1H-pyrazole-1-carboxamide
N-(4-bromophenyl)-3-(3-chloro-4-trifluoromethylphenyl)-4-carboethoxy-4-methyl-4,5-dihydro-1H-pyrazole-1-carboxamide
N-(4-bromophenyl)-3-(3-chloro-4-trifluoromethylphenyl)-4-carboethoxy-4-methyl-N-(2-methoxyethylsulfenyl)-4,5-dihydro-1H-pyrazole-1-carboxamide
N-(4-bromophenyl)-3-(3-chloro-4-trifluoromethylphenyl)-4-carboethoxy-4-methyl-N-(2-nitrophenylsulfenyl)-4,5-dihydro-1H-pyrazole-1-carboxamide
N-(4-bromophenyl)-3-(3-chloro-4-trifluoromethylphenyl)-4-carboethoxy-4-methyl-N-acetyl-4,5-dihydro-1H-pyrazole-1-carboxamide
N-(4-bromophenyl)-3-(3-chloro-4-trifluoromethylphenyl)-4-carboethoxy-4-methyl-N-carboethoxy-4,5-dihydro-1H-pyrazole-1-carboxamide
N-(4-bromophenyl)-3-(3-chloro-4-trifluoromethylphenyl)-4-carboethoxy-4-methyl-N-carbomethoxy-4,5-dihydro-1H-pyrazole-1-carboxamide
N-(4-bromophenyl)-3-(3-chloro-4-trifluoromethylphenyl)-4-carboethoxy-4-methyl-N-carbomethoxycarbonyl-4,5-dihydro-1H-pyrazole-1-carboxamide
N-(4-bromophenyl)-3-(3-chloro-4-trifluoromethylphenyl)-4-carboethoxy-4-methyl-N-carbomethoxysulfenyl-4,5-dihydro-1H-pyrazole-1-carboxamide
N-(4-bromophenyl)-3-(3-chloro-4-trifluoromethylphenyl)-4-carboethoxy-4-methyl-N-dimethylcarbamoyl-4,5-dihydro-1H-pyrazole-1-carboxamide
N-(4-bromophenyl)-3-(3-chloro-4-trifluoromethylphenyl)-4-carboethoxy-4-methyl-N-formyl-4,5-dihydro-1H-pyrazole-1-carboxamide
N-(4-bromophenyl)-3-(3-chloro-4-trifluoromethylphenyl)-4-carboethoxy-4-methyl-N-methoxymethyl-4,5-dihydro-1H-pyrazole-1-carboxamide
N-(4-bromophenyl)-3-(3-chloro-4-trifluoromethylphenyl)-4-carboethoxy-4-methyl-N-methyl-4,5-dihydro-1H-pyrazole-1-carboxamide
N-(4-bromophenyl)-3-(3-chloro-4-trifluoromethylphenyl)-4-carboethoxy-4-methyl-N-methylsulfenyl-4,5-dihydro-1H-pyrazole-1-carboxamide N-(4-bromophenyl)-3-(3-chloro-4-trifluoromethyl-
 phenyl)-4-carboethoxy-4-methyl-N-trifluoroacetyl-
 4,5-dihydro-1H-pyrazole-1-carboxamide
N-(4-bromophenyl)-3-(3-chloro-4-trifluoromethyl-
 phenyl)-4-carboethoxy-4-methylthiomethyl-4,5-dihy-
 dro-1H-pyrazole-1-carboxamide
N-(4-bromophenyl)-3-(3-chloro-4-trifluoromethyl-
 phenyl)-4-carboethoxy-4-phenyl-4,5-dihydro-1H-
 pyrazole-1-carboxamide
N-(4-bromophenyl)-3-(3-chloro-4-trifluoromethyl-
 phenyl)-4-methyl-4-(2-chloroallyl)-4,5-dihydro-1H-
 pyrazole-1-carboxamide
N-(4-bromophenyl)-3-(3-chloro-4-trifluoromethyl-
 phenyl)-4-methyl-4-(2-methylthioethyl)-4,5-dihydro-
 1H-pyrazole-1-carboxamide
N-(4-bromophenyl)-3-(3-chloro-4-trifluoromethyl-
 phenyl)-4-methyl-4-(3-cyanopropyl)-4,5-dihydro-1H-
 pyrazole-1-carboxamide
N-(4-bromophenyl)-3-(3-chloro-4-trifluoromethyl-
 phenyl)-4-methyl-4-(4-chlorophenyl)-4,5-dihydro-
 1H-pyrazole-1-carboxamide
N-(4-bromophenyl)-3-(3-chloro-4-trifluoromethyl-
 phenyl)-4-methyl-4-(4-difluoromethoxyphenyl)-4,5-
 dihydro-1H-pyrazole-1-carboxamide
N-(4-bromophenyl)-3-(3-chloro-4-trifluoromethyl-
 phenyl)-4-methyl-4-(4-trifluoromethoxyphenyl)-4,5-
 dihydro-1H-pyrazole-1-carboxamide
N-(4-bromophenyl)-3-(3-chloro-4-trifluoromethyl-
 phenyl)-4-methyl-4-(4-trifluoromethylphenyl)-4,5-
 dihydro-1H-pyrazole-1-carboxamide
N-(4-bromophenyl)-3-(3-chloro-4-trifluoromethyl-
 phenyl)-4-methyl-4-acetyl-4,5-dihydro-1H-pyrazole-
 1-carboxamide
N-(4-bromophenyl)-3-(3-chloro-4-trifluoromethyl-
 phenyl)-4-methyl-4-allyl-4,5-dihydro-1H-pyrazole-1-
 carboxamide
N-(4-bromophenyl)-3-(3-chloro-4-trifluoromethyl-
 phenyl)-4-methyl-4-benzyl-4,5-dihydro-1H-pyrazole-
 1-carboxamide
N-(4-bromophenyl)-3-(3-chloro-4-trifluoromethyl-
 phenyl)-4-methyl-4-carbomethoxy-4,5-dihydro-1H-
 pyrazole-1-carboxamide
N-(4-bromophenyl)-3-(3-chloro-4-trifluoromethyl-
 phenyl)-4-methyl-4-ethyl-4,5-dihydro-1H-pyrazole-
 1-carboxamide
N-(4-bromophenyl)-3-(3-chloro-4-trifluoromethyl-
 phenyl)-4-methyl-4-methallyl-4,5-dihydro-1H-
 pyrazole-1-carboxamide
N-(4-bromophenyl)-3-(3-chloro-4-trifluoromethyl-
 phenyl)-4-methyl-4-methoxymethyl-4,5-dihydro-1H-
 pyrazole-1-carboxamide
N-(4-bromophenyl)-3-(3-chloro-4-trifluoromethyl-
 phenyl)-4-methyl-4-methylthiomethyl-4,5-dihydro-
 1H-pyrazole-1-carboxamide
N-(4-bromophenyl)-3-(3-chloro-4-trifluoromethyl-
 phenyl)-4-methyl-4-phenyl-4,5-dihydro-1H-pyrazole-
 1-carboxamide
N-(4-bromophenyl)-3-(3-chloro-4-trifluoromethyl-
 phenyl)-4-phenyl-4-(2-chloroallyl)-4,5-dihydro-1H-
 pyrazole-1-carboxamide
N-(4-bromophenyl)-3-(3-chloro-4-trifluoromethyl-
 phenyl)-4-phenyl-4-(2-methylthioethyl)-4,5-dihydro-
 1H-pyrazole-1-carboxamide
N-(4-bromophenyl)-3-(3-chloro-4-trifluoromethyl-
 phenyl)-4-phenyl-4-(3-cyanopropyl)-4,5-dihydro-1H-
 pyrazole-1-carboxamide
N-(4-bromophenyl)-3-(3-chloro-4-trifluoromethyl-
 phenyl)-4-phenyl-4-(4-chlorophenyl)-4,5-dihydro-
 1H-pyrazole-1-carboxamide
N-(4-bromophenyl)-3-(3-chloro-4-trifluoromethyl-
 phenyl)-4-phenyl-4-(4-difluoromethoxyphenyl)-4,5-
 dihydro-1H-pyrazole-1-carboxamide
N-(4-bromophenyl)-3-(3-chloro-4-trifluoromethyl-
 phenyl)-4-phenyl-4-(4-trifluoromethoxyphenyl)-4,5-
 dihydro-1H-pyrazole-1-carboxamide
N-(4-bromophenyl)-3-(3-chloro-4-trifluoromethyl-
 phenyl)-4-phenyl-4-(4-trifluoromethylphenyl)-4,5-
 dihydro-1H-pyrazole-1-carboxamide
N-(4-bromophenyl)-3-(3-chloro-4-trifluoromethyl-
 phenyl)-4-phenyl-4-acetyl-4,5-dihydro-1H-pyrazole-
 1-carboxamide
N-(4-bromophenyl)-3-(3-chloro-4-trifluoromethyl-
 phenyl)-4-phenyl-4-allyl-4,5-dihydro-1H-pyrazole-1-
 carboxamide
N-(4-bromophenyl)-3-(3-chloro-4-trifluoromethyl-
 phenyl)-4-phenyl-4-benzyl-4,5-dihydro-1H-pyrazole-
 1-carboxamide
N-(4-bromophenyl)-3-(3-chloro-4-trifluoromethyl-
 phenyl)-4-phenyl-4-carbomethoxy-4,5-dihydro-1H-
 pyrazole-1-carboxamide
N-(4-bromophenyl)-3-(3-chloro-4-trifluoromethyl-
 phenyl)-4-phenyl-4-ethyl-4,5-dihydro-1H-pyrazole-1-
 carboxamide
N-(4-bromophenyl)-3-(3-chloro-4-trifluoromethyl-
 phenyl)-4-phenyl-4-methallyl-4,5-dihydro-1H-
 pyrazole-1-carboxamide
N-(4-bromophenyl)-3-(3-chloro-4-trifluoromethyl-
 phenyl)-4-phenyl-4-methoxymethyl-4,5-dihydro-1H-
 pyrazole-1-carboxamide
N-(4-bromophenyl)-3-(3-chloro-4-trifluoromethyl-
 phenyl)-4-phenyl-4-methyl-4,5-dihydro-1H-pyrazole-
 1-carboxamide
N-(4-bromophenyl)-3-(3-chloro-4-trifluoromethyl-
 phenyl)-4-phenyl-4-methyl-N-(2-methoxyethylsul-
 fenyl)-4,5-dihydro-1H-pyrazole-1-carboxamide
N-(4-bromophenyl)-3-(3-chloro-4-trifluoromethyl-
 phenyl)-4-phenyl-4-methyl-N-(2-nitrophenylsul-
 fenyl)-4,5-dihydro-1H-pyrazole-1-carboxamide
N-(4-bromophenyl)-3-(3-chloro-4-trifluoromethyl-
 phenyl)-4-phenyl-4-methyl-N-acetyl-4,5-dihydro-1H-
 pyrazole-1-carboxamide
N-(4-bromophenyl)-3-(3-chloro-4-trifluoromethyl-
 phenyl)-4-phenyl-4-methyl-N-carboethoxy-4,5-dihy-
 dro-1H-pyrazole-1-carboxamide
N-(4-bromophenyl)-3-(3-chloro-4-trifluoromethyl-
 phenyl)-4-phenyl-4-methyl-N-carbomethoxy-4,5-
 dihydro-1H-pyrazole-1-carboxamide
N-(4-bromophenyl)-3-(3-chloro-4-trifluoromethyl-
 phenyl)-4-phenyl-4-methyl-N-carbomethoxycarbo-
 nyl-4,5-dihydro-1H-pyrazole-1-carboxamide
N-(4-bromophenyl)-3-(3-chloro-4-trifluoromethyl-
 phenyl)-4-phenyl-4-methyl-N-carbomethoxysulfenyl-
 4,5-dihydro-1H-pyrazole-1-carboxamide
N-(4-bromophenyl)-3-(3-chloro-4-trifluoromethyl-
 phenyl)-4-phenyl-4-methyl-N-dimethylcarbamoyl-
 4,5-dihydro-1H-pyrazole-1-carboxamide
N-(4-bromophenyl)-3-(3-chloro-4-trifluoromethyl-
 phenyl)-4-phenyl-4-methyl-N-formyl-4,5-dihydro-
 1H-pyrazole-1-carboxamide
N-(4-bromophenyl)-3-(3-chloro-4-trifluoromethyl-
 phenyl)-4-phenyl-4-methyl-N-methoxymethyl-4,5-
 dihydro-1H-pyrazole-1-carboxamide N-(4-bromophenyl)-3-(3-chloro-4-trifluoromethyl-phenyl)-4-phenyl-4-methyl-N-methyl-4,5-dihydro-1H-pyrazole-1-carboxamide N-(4-bromophenyl)-3-(3-chloro-4-trifluoromethyl-phenyl)-4-phenyl-4-methyl-N-methylsulfenyl-4,5-dihydro-1H-pyrazole-1-carboxamide N-(4-bromophenyl)-3-(3-chloro-4-trifluoromethyl-phenyl)-4-phenyl-4-methyl-N-trifluoroacetyl-4,5-dihydro-1H-pyrazole-1-carboxamide N-(4-bromophenyl)-3-(3-chloro-4-trifluoromethyl-phenyl)-4-phenyl-4-methylthiomethyl-4,5-dihydro-1H-pyrazole-1-carboxamide N-(4-bromophenyl)-3-(4-chlorophenyl)-4-(3-methylthiopropyl)-4-acetyl-4,5-dihydro-1H-pyrazole-1-carboxamide N-(4-bromophenyl)-3-(4-chlorophenyl)-4-(3-methylthiopropyl)-4-carbomethoxy-4,5-dihydro-1H-pyrazole-1-carboxamide N-(4-bromophenyl)-3-(4-chlorophenyl)-4-(3-methylthiopropyl)-4-ethyl-4,5-dihydro-1H-pyrazole-1-carboxamide N-(4-bromophenyl)-3-(4-chlorophenyl)-4-(3-methylthiopropyl)-4-methyl-4,5-dihydro-1H-pyrazole-1-carboxamide N-(4-bromophenyl)-3-(4-chlorophenyl)-4-(3-methylthiopropyl)-4-methyl-N-(2-methoxyethylsulfenyl)-4,5-dihydro-1H-pyrazole-1-carboxamide N-(4-bromophenyl)-3-(4-chlorophenyl)-4-(3-methylthiopropyl)-4-methyl-N-(2-nitrophenylsulfenyl)-4,5-dihydro-1H-pyrazole-1-carboxamide N-(4-bromophenyl)-3-(4-chlorophenyl)-4-(3-methylthiopropyl)-4-methyl-N-acetyl-4,5-dihydro-1H-pyrazole-1-carboxamide N-(4-bromophenyl)-3-(4-chlorophenyl)-4-(3-methylthiopropyl)-4-methyl-N-carboethoxy-4,5-dihydro-1H-pyrazole-1-carboxamide N-(4-bromophenyl)-3-(4-chlorophenyl)-4-(3-methylthiopropyl)-4-methyl-N-carbomethoxy-4,5-dihydro-1H-pyrazole-1-carboxamide N-(4-bromophenyl)-3-(4-chlorophenyl)-4-(3-methylthiopropyl)-4-methyl-N-carbomethoxysulfenyl-4,5-dihydro-1H-pyrazole-1-carboxamide N-(4-bromophenyl)-3-(4-chlorophenyl)-4-(3-methylthiopropyl)-4-methyl-N-dimethylcarbamoyl-4,5-dihydro-1H-pyrazole-1-carboxamide N-(4-bromophenyl)-3-(4-chlorophenyl)-4-(3-methylthiopropyl)-4-methyl-N-formyl-4,5-dihydro-1H-pyrazole-1-carboxamide N-(4-bromophenyl)-3-(4-chlorophenyl)-4-(3-methylthiopropyl)-4-methyl-N-methoxymethyl-4,5-dihydro-1H-pyrazole-1-carboxamide N-(4-bromophenyl)-3-(4-chlorophenyl)-4-(3-methylthiopropyl)-4-methyl-N-methyl-4,5-dihydro-1H-pyrazole-1-carboxamide N-(4-bromophenyl)-3-(4-chlorophenyl)-4-(3-methylthiopropyl)-4-methyl-N-methylsulfenyl-4,5-dihydro-1H-pyrazole-1-carboxamide N-(4-bromophenyl)-3-(4-chlorophenyl)-4-(3-methylthiopropyl)-4-methyl-N-trifluoroacetyl-4,5-dihydro-1H-pyrazole-1-carboxamide N-(4-bromophenyl)-3-(4-chlorophenyl)-4-(3-methylthiopropyl)-4-methylthiomethyl-4,5-dihydro-1H-pyrazole-1-carboxamide N-(4-bromophenyl)-3-(4-chlorophenyl)-4-(3-methylthiopropyl)-4-phenyl-4,5-dihydro-1H-pyrazole-1-carboxamide N-(4-bromophenyl)-3-(4-chlorophenyl)-4-carboethoxy-4-(2-chloroallyl)-4,5-dihydro-1H-pyrazole-1-carboxamide N-(4-bromophenyl)-3-(4-chlorophenyl)-4-carboethoxy-4-(2-methylthioethyl)-4,5-dihydro-1H-pyrazole-1-carboxamide N-(4-bromophenyl)-3-(4-chlorophenyl)-4-carboethoxy-4-(3-cyanopropyl)-4,5-dihydro-1H-pyrazole-1-carboxamide N-(4-bromophenyl)-3-(4-chlorophenyl)-4-carboethoxy-4-(chlorophenyl)-4,5-dihydro-1H-pyrazole-1-carboxamide N-(4-bromophenyl)-3-(4-chlorophenyl)-4-carboethoxy-4-(4-difluoromethoxyphenyl)-4,5-dihydro-1H-pyrazole-1-carboxamide N-(4-bromophenyl)-3-(4-chlorophenyl)-4-carboethoxy-4-(4-trifluoromethoxyphenyl)-4,5-dihydro-1H-pyrazole-1-carboxamide N-(4-bromophenyl)-3-(4-chlorophenyl)-4-carboethoxy-4-(4-trifluoromethylphenyl)-4,5-dihydro-1H-pyrazole-1-carboxamide N-(4-bromophenyl)-3-(4-chlorophenyl)-4-carboethoxy-4-acetyl-4,5-dihydro-1H-pyrazole-1-carboxamide N-(4-bromophenyl)-3-(4-chlorophenyl)-4-carboethoxy-4-allyl-4,5-dihydro-1H-pyrazole-1-carboxamide N-(4-bromophenyl)-3-(4-chlorophenyl)-4-carboethoxy-4-benzyl-4,5-dihydro-1H-pyrazole-1-carboxamide N-(4-bromophenyl)-3-(4-chlorophenyl)-4-carboethoxy-4-carbomethoxy-4,5-dihydro-1H-pyrazole-1-carboxamide N-(4-bromophenyl)-3-(4-chlorophenyl)-4-carboethoxy-4-ethyl-4,5-dihydro-1H-pyrazole-1-carboxamide N-(4-bromophenyl)-3-(4-chlorophenyl)-4-carboethoxy-4-methallyl-4,5-dihydro-1H-pyrazole-1-carboxamide N-(4-bromophenyl)-3-(4-chlorophenyl)-4-carboethoxy-4-methoxymethyl-4,5-dihydro-1H-pyrazole-1-carboxamide N-(4-bromophenyl)-3-(4-chlorophenyl)-4-carboethoxy-4-methyl-4,5-dihydro-1H-pyrazole-1-carboxamide N-(4-bromophenyl)-3-(4-chlorophenyl)-4-carboethoxy-4-methyl-N-(2-methoxyethylsulfenyl)-4,5-dihydro-1H-pyrazole-1-carboxamide N-(4-bromophenyl)-3-(4-chlorophenyl)-4-carboethoxy-4-methyl-N-(2-nitrophenylsulfenyl)-4,5-dihydro-1H-pyrazole-1-carboxamide N-(4-bromophenyl)-3-(4-chlorophenyl)-4-carboethoxy-4-methyl-N-acetyl-4,5-dihydro-1H-pyrazole-1-carboxamide N-(4-bromophenyl)-3-(4-chlorophenyl)-4-carboethoxy-4-methyl-N-carboethoxy-4,5-dihydro-1H-pyrazole-1-carboxamide N-(4-bromophenyl)-3-(4-chlorophenyl)-4-carboethoxy-4-methyl-N-carbomethoxy-4,5-dihydro-1H-pyrazole-1-carboxamide N-(4-bromophenyl)-3-(4-chlorophenyl)-4-carboethoxy-4-methyl-N-carbomethoxycarbonyl-4,5-dihydro-1H-pyrazole-1-carboxamide N-(4-bromophenyl)-3-(4-chlorophenyl)-4-carboethoxy-4-methyl-N-carbomethoxysulfenyl-4,5-dihydro-1H-pyrazole-1-carboxamide N-(4-bromophenyl)-3-(4-chlorophenyl)-4-carboethoxy-4-methyl-N-dimethylcarbamoyl-4,5-dihydro-1H-pyrazole-1-carboxamide N-(4-bromophenyl)-3-(4-chlorophenyl)-4-carboethoxy-4-methyl-N-formyl-4,5-dihydro-1H-pyrazole-1-carboxamide N-(4-bromophenyl)-3-(4-chlorophenyl)-4-carboethoxy-4-methyl-N-methoxymethyl-4,5-dihydro-1H-pyrazole-1-carboxamide
N-(4-bromophenyl)-3-(4-chlorophenyl)-4-carboethoxy-4-methyl-N-methyl-4,5-dihydro-1H-pyrazole-1-carboxamide
N-(4-bromophenyl)-3-(4-chlorophenyl)-4-carboethoxy-4-methyl-N-methylsulfenyl-4,5-dihydro-1H-pyrazole-1-carboxamide
N-(4-bromophenyl)-3-(4-chlorophenyl)-4-carboethoxy-4-methyl-N-trifluoroacetyl-4,5-dihydro-1H-pyrazole-1-carboxamide
N-(4-bromophenyl)-3-(4-chlorophenyl)-4-carboethoxy-4-methylthiomethyl-4,5-dihydro-1H-pyrazole-1-carboxamide
N-(4-bromophenyl)-3-(4-chlorophenyl)-4-carboethoxy-4-phenyl-4,5-dihydro-1H-pyrazole-1-carboxamide
N-(4-bromophenyl)-3-(4-chlorophenyl)-4-carbomethoxy-4-methyl-4,5-dihydro-1H-pyrazole-1-carboxamide
N-(4-bromophenyl)-3-(4-chlorophenyl)-4-methyl-4-(2-chloroallyl)-4,5-dihydro-1H-pyrazole-1-carboxamide
N-(4-bromophenyl)-3-(4-chlorophenyl)-4-methyl-4-(2-methylthioethyl)-4,5-dihydro-1H-pyrazole-1-carboxamide
N-(4-bromophenyl)-3-(4-chlorophenyl)-4-methyl-4-(3-cyanopropyl)-4,5-dihydro-1H-pyrazole-1-carboxamide
N-(4-bromophenyl)-3-(4-chlorophenyl)-4-methyl-4-(4-chlorophenyl)-4,5-dihydro-1H-pyrazole-1-carboxamide
N-(4-bromophenyl)-3-(4-chlorophenyl)-4-methyl-4-(4-difluoromethoxyphenyl)-4,5-dihydro-1H-pyrazole-1-carboxamide
N-(4-bromophenyl)-3-(4-chlorophenyl)-4-methyl-4-(4-trifluoromethoxyphenyl)-4,5-dihydro-1H-pyrazole-1-carboxamide
N-(4-bromophenyl)-3-(4-chlorophenyl)-4-methyl-4-(4-trifluoromethylphenyl)-4,5-dihydro-1H-pyrazole-1-carboxamide
N-(4-bromophenyl)-3-(4-chlorophenyl)-4-methyl-4-acetyl-4,5-dihydro-1H-pyrazole-1-carboxamide
N-(4-bromophenyl)-3-(4-chlorophenyl)-4-methyl-4-allyl-4,5-dihydro-1H-pyrazole-1-carboxamide
N-(4-bromophenyl)-3-(4-chlorophenyl)-4-methyl-4-benzyl-4,5-dihydro-1H-pyrazole-1-carboxamide
N-(4-bromophenyl)-3-(4-chlorophenyl)-4-methyl-4-carbomethoxy-4,5-dihydro-1H-pyrazole-1-carboxamide
N-(4-bromophenyl)-3-(4-chlorophenyl)-4-methyl-4-ethyl-4,5-dihydro-1H-pyrazole-1-carboxamide
N-(4-bromophenyl)-3-(4-chlorophenyl)-4-methyl-4-methallyl-4,5-dihydro-1H-pyrazole-1-carboxamide
N-(4-bromophenyl)-3-(4-chlorophenyl)-4-methyl-4-methoxymethyl-4,5-dihydro-1H-pyrazole-1-carboxamide
N-(4-bromophenyl)-3-(4-chlorophenyl)-4-methyl-4-methylthiomethyl-4,5-dihydro-1H-pyrazole-1-carboxamide
N-(4-bromophenyl)-3-(4-chlorophenyl)-4-methyl-4-phenyl-4,5-dihydro-1H-pyrazole-1-carboxamide
N-(4-bromophenyl)-3-(4-chlorophenyl)-4-phenyl-4-(2-chloroallyl)-4,5-dihydro-1H-pyrazole-1-carboxamide
N-(4-bromophenyl)-3-(4-chlorophenyl)-4-phenyl-4-(2-methylthioethyl)-4,5-dihydro-1H-pyrazole-1-carboxamide
N-(4-bromophenyl)-3-(4-chlorophenyl)-4-phenyl-4-(3-cyanopropyl)-4,5-dihydro-1H-pyrazole-1-carboxamide
N-(4-bromophenyl)-3-(4-chlorophenyl)-4-phenyl-4-(4-chlorophenyl)-4,5-dihydro-1H-pyrazole-1-carboxamide
N-(4-bromophenyl)-3-(4-chlorophenyl)-4-phenyl-4-(4-difluoromethoxyphenyl)-4,5-dihydro-1H-pyrazole-1-carboxamide
N-(4-bromophenyl)-3-(4-chlorophenyl)-4-phenyl-4-(4-trifluoromethoxyphenyl)-4,5-dihydro-1H-pyrazole-1-carboxamide
N-(4-bromophenyl)-3-(4-chlorophenyl)-4-phenyl-4-(4-trifluoromethylphenyl)-4,5-dihydro-1H-pyrazole-1-carboxamide
N-(4-bromophenyl)-3-(4-chlorophenyl)-4-phenyl-4-acetyl-4,5-dihydro-1H-pyrazole-1-carboxamide
N-(4-bromophenyl)-3-(4-chlorophenyl)-4-phenyl-4-allyl-4,5-dihydro-1H-pyrazole-1-carboxamide
N-(4-bromophenyl)-3-(4-chlorophenyl)-4-phenyl-4-benzyl-4,5-dihydro-1H-pyrazole-1-carboxamide
N-(4-bromophenyl)-3-(4-chlorophenyl)-4-phenyl-4-carbomethoxy-4,5-dihydro-1H-pyrazole-1-carboxamide
N-(4-bromophenyl)-3-(4-chlorophenyl)-4-phenyl-4-ethyl-4,5-dihydro-1H-pyrazole-1-carboxamide
N-(4-bromophenyl)-3-(4-chlorophenyl)-4-phenyl-4-methallyl-4,5-dihydro-1H-pyrazole-1-carboxamide
N-(4-bromophenyl)-3-(4-chlorophenyl)-4-phenyl-4-methoxymethyl-4,5-dihydro-1H-pyrazole-1-carboxamide
N-(4-bromophenyl)-3-(4-chlorophenyl)-4-phenyl-4-methyl-4,5-dihydro-1H-pyrazole-1-carboxamide
N-(4-bromophenyl)-3-(4-chlorophenyl)-4-phenyl-4-methyl-N-(2-methoxyethylsulfenyl)-4,5-dihydro-1H-pyrazole-1-carboxamide
N-(4-bromophenyl)-3-(4-chlorophenyl)-4-phenyl-4-methyl-N-(2-nitrophenylsulfenyl)-4,5-dihydro-1H-pyrazole-1-carboxamide
N-(4-bromophenyl)-3-(4-chlorophenyl)-4-phenyl-4-methyl-N-acetyl-4,5-dihydro-1H-pyrazole-1-carboxamide
N-(4-bromophenyl)-3-(4-chlorophenyl)-4-phenyl-4-methyl-N-carboethoxy-4,5-dihydro-1H-pyrazole-1-carboxamide
N-(4-bromophenyl)-3-(4-chlorophenyl)-4-phenyl-4-methyl-N-carbomethoxy-4,5-dihydro-1H-pyrazole-1-carboxamide
N-(4-bromophenyl)-3-(4-chlorophenyl)-4-phenyl-4-methyl-N-carbomethoxycarbonyl-4,5-dihydro-1H-pyrazole-1-carboxamide
N-(4-bromophenyl)-3-(4-chlorophenyl)-4-phenyl-4-methyl-N-carbomethoxysulfenyl-4,5-dihydro-1H-pyrazole-1-carboxamide
N-(4-bromophenyl)-3-(4-chlorophenyl)-4-phenyl-4-methyl-N-dimethylcarbamoyl-4,5-dihydro-1H-pyrazole-1-carboxamide
N-(4-bromophenyl)-3-(4-chlorophenyl)-4-phenyl-4-methyl-N-formyl-4,5-dihydro-1H-pyrazole-1-carboxamide
N-(4-bromophenyl)-3-(4-chlorophenyl)-4-phenyl-4-methyl-N-methoxymethyl-4,5-dihydro-1H-pyrazole-1-carboxamide
N-(4-bromophenyl)-3-(4-chlorophenyl)-4-phenyl-4-methyl-N-methyl-4,5-dihydro-1H-pyrazole-1-carboxamide
N-(4-bromophenyl)-3-(4-chlorophenyl)-4-phenyl-4-methyl-N-methylsulfenyl-4,5-dihydro-1H-pyrazole-1-carboxamide
N-(4-bromophenyl)-3-(4-chlorophenyl)-4-phenyl-4-methyl-N-trifluoroacetyl-4,5-dihydro-1H-pyrazole-1-carboxamide N-(4-bromophenyl)-3-(4-chlorophenyl)-4-phenyl-4-methylthiomethyl-4,5-dihydro-1H-pyrazole-1-carboxamide
N-(4-bromophenyl)-3-(4-fluorophenyl)-4-butyl-4-methyl-4,5-dihydro-1H-pyrazole-1-carboxamide
N-(4-bromophenyl)-3-(4-fluorophenyl)-4-carbomethoxy-4-methyl-4,5-dihydro-1H-pyrazole-1-carboxamide
N-(4-bromophenyl)-3-phenyl-4-carbomethoxy-4-methyl-4,5-dihydro-1H-pyrazole-1-carboxamide
N-(4-carboethoxyphenyl)-3-(3-chloro-4-trifluoromethylphenyl)-4-carboethoxy-4-methyl-4,5-dihydro-1H-pyrazole-1-carboxamide
N-(4-carboethoxyphenyl)-3-(4-chlorophenyl)-4-carboethoxy-4-methyl-4,5-dihydro-1H-pyrazole-1-carboxamide
N-(4-carboethoxyphenyl)-3-(4-chlorophenyl)-4-phenyl-4-methyl-4,5-dihydro-1H-pyrazole-1-carboxamide
N-(4-carboisopropoxyphenyl)-3-(3-chloro-4-trifluoromethylphenyl)-4-(3-methylthiopropyl)-4-methyl-4,5-dihydro-1H-pyrazole-1-carboxamide
N-(4-carboisopropoxyphenyl)-3-(3-chloro-4-trifluoromethylphenyl)-4-carboethoxy-4-methyl-4,5-dihydro-1H-pyrazole-1-carboxamide
N-(4-carboisopropoxyphenyl)-3-(3-chloro-4-trifluoromethylphenyl)-4-phenyl-4-methyl-4,5-dihydro-1H-pyrazole-1-carboxamide
N-(4-carboisopropoxyphenyl)-3-(4-chlorophenyl)-4-(3-methylthiopropyl)-4-methyl-4,5-dihydro-1H-pyrazole-1-carboxamide
N-(4-carboisopropoxyphenyl)-3-(4-chlorophenyl)-4-carboethoxy-4-methyl-4,5-dihydro-1H-pyrazole-1-carboxamide
N-(4-carboisopropoxyphenyl)-3-(4-chlorophenyl)-4-phenyl-4-methyl-4,5-dihydro-1H-pyrazole-1-carboxamide
N-(4-carbomethoxyphenyl)-3-(3-chloro-4-trifluoromethylphenyl)-4-(3-methylthiopropyl)-4-methyl-4,5-dihydro-1H-pyrazole-1-carboxamide
N-(4-carbomethoxyphenyl)-3-(3-chloro-4-trifluoromethylphenyl)-4-carboethoxy-4-methyl-4,5-dihydro-1H-pyrazole-1-carboxamide
N-(4-carbomethoxyphenyl)-3-(3-chloro-4-trifluoromethylphenyl)-4-phenyl-4-methyl-4,5-dihydro-1H-pyrazole-1-carboxamide
N-(4-carbomethoxyphenyl)-3-(4-chlorophenyl)-4-(3-methylthiopropyl)-4-methyl-4,5-dihydro-1H-pyrazole-1-carboxamide
N-(4-carbomethoxyphenyl)-3-(4-chlorophenyl)-4-carboethoxy-4-methyl-4,5-dihydro-1H-pyrazole-1-carboxamide
N-(4-carbomethoxyphenyl)-3-(4-chlorophenyl)-4-phenyl-4-methyl-4,5-dihydro-1H-pyrazole-1-carboxamide
N-(4-bromo-3-methylphenyl)-3-(4-chlorophenyl)-4-carbomethoxy-4-methyl-4,5-dihydro-1H-pyrazole-1-carboxamide
N-(4-chloro-3-trifluoromethylphenyl)-3-(4-chlorophenyl)-4-carbomethoxy-4-methyl-4,5-dihydro-1H-pyrazole-1-carboxamide
N-(4-chlorophenyl)-3-(3,4-dichlorophenyl)-4-phenyl-4-methyl-4,5-dihydro-1H-pyrazole-1-carboxamide
N-(4-chlorophenyl)-3-(4-bromophenyl)-4-butyl-4-methyl-4,5-dihydro-1H-pyrazole-1-carboxamide
N-(4-chlorophenyl)-3-(4-bromophenyl)-4-butyl-4-methyl-N-(1-methylethyl)-4,5-dihydro-1H-pyrazole-1-carboxamide
N-(4-chlorophenyl)-3-(4-bromophenyl)-4-carbomethoxy-4-methyl-4,5-dihydro-1H-pyrazole-1-carboxamide
N-(4-chlorophenyl)-3-(4-fluorophenyl)-4-butyl-4-methyl-4,5-dihydro-1H-pyrazole-1-carboxamide
N-(4-chlorophenyl)-3-(4-fluorophenyl)-4-carbomethoxy-4-methyl-4,5-dihydro-1H-pyrazole-1-carboxamide
N-(4-chlorophenyl)-3-(4-methylphenyl)-4-carbomethoxy-4-methyl-4,5-dihydro-1H-pyrazole-1-carboxamide
N-(4-chlorophenyl)-3-(4-methoxyphenyl)-4-carbomethoxy-4-methyl-4,5-dihydro-1H-pyrazole-1-carboxamide
N-(4-chlorophenyl)-3-(4-methylsulfonylphenyl)-4-carbomethoxy-4-methyl-4,5-dihydro-1H-pyrazole-1-carboxamide
N-(4-chlorophenyl)-3-(4-methylthiophenyl)-4-carbomethoxy-4-methyl-4,5-dihydro-1H-pyrazole-1-carboxamide
N-(4-chlorophenyl)-3-(4-trifluoromethylphenyl)-4-carbomethoxy-4-methyl-4,5-dihydro-1H-pyrazole-1-carboxamide
N-(4-chlorophenyl)-3-phenyl-4-carboethoxy-4-methyl-4,5-dihydro-1H-pyrazole-1-carboxamide
N-(4-chlorophenyl)-3-phenyl-4-carbomethoxy-4-methyl-4,5-dihydro-1H-pyrazole-1-carboxamide
N-(4-chlorophenyl)-3-phenyl-4-dimethylcarboxamido-4-methyl-4,5-dihydro-1H-pyrazole-1-carboxamide
N-(4-chlorophenyl)-3-phenyl-N,4-bis-carbomethoxy-4-methyl-4,5-dihydro-1H-pyrazole-1-carboxamide
N-(4-chlorophenyl)-4-methyl-3,4-diphenyl-4,5-dihydro-1H-pyrazole-1-carboxamide
N-(4-difluoromethoxyphenyl)-3-(3-chloro-4-trifluoromethylphenyl)-4-(3-methylthiopropyl)-4-methyl-4,5-dihydro-1H-pyrazole-1-carboxamide
N-(4-difluoromethoxyphenyl)-3-(3-chloro-4-trifluoromethylphenyl)-4-carboethoxy-4-methyl-4,5-dihydro-1H-pyrazole-1-carboxamide
N-(4-difluoromethoxyphenyl)-3-(3-chloro-4-trifluoromethylphenyl)-4-phenyl-4-methyl-4,5-dihydro-1H-pyrazole-1-carboxamide
N-(4-difluoromethoxyphenyl)-3-(4-chlorophenyl)-4-(3-methylthiopropyl)-4-methyl-4,5-dihydro-1H-pyrazole-1-carboxamide
N-(4-difluoromethoxyphenyl)-3-(4-chlorophenyl)-4-carboethoxy-4-methyl-4,5-dihydro-1H-pyrazole-1-carboxamide
N-(4-difluoromethoxyphenyl)-3-(4-chlorophenyl)-4-phenyl-4-methyl-4,5-dihydro-1H-pyrazole-1-carboxamide
N-(4-dimethylaminoxyphenyl)-3-(4-chlorophenyl)-4-carbomethoxy-4-methyl-4,5-dihydro-1H-pyrazole-1-carboxamide
N-(4-dimethylsulfonamidophenyl)-3-(3-chloro-4-trifluoromethylphenyl)-4-(3-methylthiopropyl)-4-methyl-4,5-dihydro-1H-pyrazole-1-carboxamide
N-(4-dimethylsulfonamidophenyl)-3-(3-chloro-4-trifluoromethylphenyl)-4-carboethoxy-4-methyl-4,5-dihydro-1H-pyrazole-1-carboxamide
N-(4-dimethylsulfonamidophenyl)-3-(3-chloro-4-trifluoromethylphenyl)-4-phenyl-4-methyl-4,5-dihydro-1H-pyrazole-1-carboxamide
N-(4-dimethylsulfonamidophenyl)-3-(4-chlorophenyl)-4-(3-methylthiopropyl)-4-methyl-4,5-dihydro-1H-pyrazole-1-carboxamide N-(4-dimethylsulfonamidophenyl)-3-(4-chlorophenyl)-4-carboethoxy-4-methyl-4,5-dihydro-1H-pyrazole-1-carboxamide N-(4-dimethylsulfonamidophenyl)-3-(4-chlorophenyl)-4-phenyl-4-methyl-4,5-dihydro-1H-pyrazole-1-carboxamide N-(4-fluorophenyl)-3-(4-bromophenyl)-4-carbomethoxy-4-methyl-4,5-dihydro-1H-pyrazole-1-carboxamide N-(4-fluorophenyl)-3-(4-chlorophenyl)-4-carbomethoxy-4-methyl-4,5-dihydro-1H-pyrazole-1-carboxamide N-(4-fluorophenyl)-3-(4-fluorophenyl)-4-carbomethoxy-4-methyl-4,5-dihydro-1H-pyrazole-1-carboxamide N-(4-fluorophenyl)-3-phenyl-4-carbomethoxy-4-methyl-4,5-dihydro-1H-pyrazole-1-carboxamide N-(4-iodophenyl)-3-(4-chlorophenyl)-4-carbomethoxy-4-methyl-4,5-dihydro-1H-pyrazole-1-carboxamide N-(4-methoxyphenyl)-3-(4-chlorophenyl)-4-carbomethoxy-4-methyl-4,5-dihydro-1H-pyrazole-1-carboxamide N-(4-methylphenyl)-3-(4-chlorophenyl)-4-carbomethoxy-4-methyl-4,5-dihydro-1H-pyrazole-1-carboxamide N-(4-methylsulfonylphenyl)-3-(3-chloro-4-trifluoromethylphenyl)-4-(3-methylthiopropyl)-4-methyl-4,5-dihydro-1H-pyrazole-1-carboxamide N-(4-methylsulfonylphenyl)-3-(3-chloro-4-trifluoromethylphenyl)-4-carboethoxy-4-methyl-4,5-dihydro-1H-pyrazole-1-carboxamide N-(4-methylsulfonylphenyl)-3-(3-chloro-4-trifluoromethylphenyl)-4-phenyl-4-methyl-4,5-dihydro-1H-pyrazole-1-carboxamide N-(4-methylsulfonylphenyl)-3-(4-chlorophenyl)-4-(3-methylthiopropyl)-4-methyl-4,5-dihydro-1H-pyrazole-1-carboxamide N-(4-methylsulfonylphenyl)-3-(4-chlorophenyl)-4-carboethoxy-4-methyl-4,5-dihydro-1H-pyrazole-1-carboxamide N-(4-methylsulfonylphenyl)-3-(4-chlorophenyl)-4-carbomethoxy-4-methyl-4,5-dihydro-1H-pyrazole-1-carboxamide N-(4-methylsulfonylphenyl)-3-(4-chlorophenyl)-4-phenyl-4-methyl-4,5-dihydro-1H-pyrazole-1-carboxamide N-(4-methylsulfoxylphenyl)-3-(4-chlorophenyl)-4-carbomethoxy-4-methyl-4,5-dihydro-1H-pyrazole-1-carboxamide N-(4-methylthiophenyl)-3-(3-chloro-4-trifluoromethylphenyl)-4-(3-methylthiopropyl)-4-methyl-4,5-dihydro-1H-pyrazole-1-carboxamide N-(4-methylthiophenyl)-3-(3-chloro-4-trifluoromethylphenyl)-4-carboethoxy-4-methyl-4,5-dihydro-1H-pyrazole-1-carboxamide N-(4-methylthiophenyl)-3-(3-chloro-4-trifluoromethylphenyl)-4-phenyl-4-methyl-4,5-dihydro-1H-pyrazole-1-carboxamide N-(4-methylthiophenyl)-3-(4-chlorophenyl)-4-(3-methylthiopropyl)-4-methyl-4,5-dihydro-1H-pyrazole-1-carboxamide N-(4-methylthiophenyl)-3-(4-chlorophenyl)-4-carboethoxy-4-methyl-4,5-dihydro-1H-pyrazole-1-carboxamide N-(4-methylthiophenyl)-3-(4-chlorophenyl)-4-carbomethoxy-4-methyl-4,5-dihydro-1H-pyrazole-1-carboxamide N-(4-methylthiophenyl)-3-(4-chlorophenyl)-4-phenyl-4-methyl-4,5-dihydro-1H-pyrazole-1-carboxamide N-(4-nitrophenyl)-3-(3-chloro-4-trifluoromethylphenyl)-4-(3-methylthiopropyl)-4-methyl-4,5-dihydro-1H-pyrazole-1-carboxamide N-(4-nitrophenyl)-3-(3-chloro-4-trifluoromethylphenyl)-4-carboethoxy-4-methyl-4,5-dihydro-1H-pyrazole-1-carboxamide N-(4-nitrophenyl)-3-(3-chloro-4-trifluoromethylphenyl)-4-phenyl-4-methyl-4,5-dihydro-1H-pyrazole-1-carboxamide N-(4-nitrophenyl)-3-(4-chlorophenyl)-4-(3-methylthiopropyl)-4-methyl-4,5-dihydro-1H-pyrazole-1-carboxamide N-(4-nitrophenyl)-3-(4-chlorophenyl)-4-carboethoxy-4-methyl-4,5-dihydro-1H-pyrazole-1-carboxamide N-(4-nitrophenyl)-3-(4-chlorophenyl)-4-carbomethoxy-4,5-dihydro-1H-pyrazole-1-carboxamide N-(4-nitrophenyl)-3-(4-chlorophenyl)-4-phenyl-4-methyl-4,5-dihydro-1H-pyrazole-1-carboxamide N-(4-phenylphenyl)-3-(3-chloro-4-trifluoromethylphenyl)-4-phenyl-4-methyl-4,5-dihydro-1H-pyrazole-1-carboxamide N-(4-phenylphenyl)-3-(4-chlorophenyl)-4-phenyl-4-methyl-4,5-dihydro-1H-pyrazole-1-carboxamide N-(4-trifluoromethoxyphenyl)-3-(3-chloro-4-trifluoromethylphenyl)-4-(3-methylthiopropyl)-4-methyl-4,5-dihydro-1H-pyrazole-1-carboxamide N-(4-trifluoromethoxyphenyl)-3-(3-chloro-4-trifluoromethylphenyl)-4-carboethoxy-4-methyl-4,5-dihydro-1H-pyrazole-1-carboxamide N-(4-trifluoromethoxyphenyl)-3-(3-chloro-4-trifluoromethylphenyl)-4-phenyl-4-methyl-4,5-dihydro-1H-pyrazole-1-carboxamide N-(4-trifluoromethoxyphenyl)-3-(4-chlorophenyl)-4-(3-methylthiopropyl)-4-methyl-4,5-dihydro-1H-pyrazole-1-carboxamide N-(4-trifluoromethoxyphenyl)-3-(4-chlorophenyl)-4-carboethoxy-4-methyl-4,5-dihydro-1H-pyrazole-1-carboxamide N-(4-trifluoromethoxyphenyl)-3-(4-chlorophenyl)-4-carbomethoxy-4-methyl-4,5-dihydro-1H-pyrazole-1-carboxamide N-(4-trifluoromethoxyphenyl)-3-(4-chlorophenyl)-4-phenyl-4-methyl-4,5-dihydro-1H-pyrazole-1-carboxamide N-(trimethylammoniumphenyl)-3-(4-chlorophenyl)-4-carbomethoxy-4-methyl-4,5-dihydro-1H-pyrazole-1-carboxamide iodide N-(4-trifluoromethylphenyl)-3-(3-chloro-4-trifluoromethylphenyl)-4-(3-methylthiopropyl)-4-acetyl-4,5-dihydro-1H-pyrazole-1-carboxamide N-(4-trifluoromethylphenyl)-3-(3-chloro-4-trifluoromethylphenyl)-4-(3-methylthiopropyl)-4-carbomethoxy-4,5-dihydro-1H-pyrazole-1-carboxamide N-(4-trifluoromethylphenyl)-3-(3-chloro-4-trifluoromethylphenyl)-4-(3-methylthiopropyl)-4-ethyl-4,5-dihydro-1H-pyrazole-1-carboxamide N-(4-trifluoromethylphenyl)-3-(3-chloro-4-trifluoromethylphenyl)-4-(3-methylthiopropyl)-4-methyl-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-(2-methoxyethylsulfenyl)-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-(2- nitrophenylsulfenyl)-4,5-dihydro-1H-pyrazole-1-carboxamide

N-(4-trifluoromethylphenyl)-3-(3-chloro-4-trifluoromethylphenyl)-4-(3-methylthiopropyl)-4-methyl-N-acetyl-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-carboethoxy-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-carbomethoxy-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-carbomethoxycarbonyl-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-carbomethoxysulfenyl-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-dimethylcarbamoyl-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-formyl-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-methoxymethyl-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-methyl-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-methylsulfenyl-4,5-dihydro-1H-pyrazole-1-carboxamide N-(4-trifluoromethylphenyl)-3-(3-chloro-4-trifluoromethylphenyl)-4-(3-methylthiopropyl)-4-methyl-N-trifluoroacetyl-4,5-dihydro-1H-pyrazole-1-carboxamide N-(4-trifluoromethylphenyl)-3-(3-chloro-4-trifluoromethylphenyl)-4-carboethoxy-4-(2-chloroallyl)-4,5-dihydro-1H-pyrazole-1-carboxamide N-(4-trifluoromethylphenyl)-3-(3-chloro-4-trifluoromethylphenyl)-4-carboethoxy-4-(2-methylthioethyl)-4,5-dihydro-1H-pyrazole-1-carboxamide N-(4-trifluoromethylphenyl)-3-(3-chloro-4-trifluoromethylphenyl)-4-carboethoxy-4-(3-cyanopropyl)-4,5-dihydro-1H-pyrazole-1-carboxamide N-(4-trifluoromethylphenyl)-3-(3-chloro-4-trifluoromethylphenyl)-4-carboethoxy-4-(4-chlorophenyl)-4,5-dihydro-1H-pyrazole-1-carboxamide N-(4-trifluoromethylphenyl)-3-(3-chloro-4-trifluoromethylphenyl)-4-carboethoxy-4-(4-difluoromethoxyphenyl)-4,5-dihydro-1H-pyrazole-1-carboxamide N-(4-trifluoromethylphenyl)-3-(3-chloro-4-trifluoromethylphenyl)-4-carboethoxy-4-(4-trifluoromethoxyphenyl)-4,5-dihydro-1H-pyrazole-1-carboxamide N-(4-trifluoromethylphenyl)-3-(3-chloro-4-trifluoromethylphenyl)-4-carboethoxy-4-(4-trifluoromethylphenyl)-4,5-dihydro-1H-pyrazole-1-carboxamide N-(4-trifluoromethylphenyl)-3-(3-chloro-4-trifluoromethylphenyl)-4-carboethoxy-4-acetyl-4,5-dihydro-1H-pyrazole-1-carboxamide N-(4-trifluoromethylphenyl)-3-(3-chloro-4-trifluoromethylphenyl)-4-carboethoxy-4-allyl-4,5-dihydro-1H-pyrazole-1-carboxamide N-(4-trifluoromethylphenyl)-3-(3-chloro-4-trifluoromethylphenyl)-4-carboethoxy-4-benzyl-4,5-dihydro-1H-pyrazole-1-carboxamide N-(4-trifluoromethylphenyl)-3-(3-chloro-4-trifluoromethylphenyl)-4-carboethoxy-4-carbomethoxy-4,5-dihydro-1H-pyrazole-1-carboxamide N-(4-trifluoromethylphenyl)-3-(3-chloro-4-trifluoromethylphenyl)-4-carboethoxy-4-ethyl-4,5-dihydro-1H-pyrazole-1-carboxamide N-(4-trifluoromethylphenyl)-3-(3-chloro-4-trifluoromethylphenyl)-4-carboethoxy-4-methallyl-4,5-dihydro-1H-pyrazole-1-carboxamide N-(4-trifluoromethylphenyl)-3-(3-chloro-4-trifluoromethylphenyl)-4-carboethoxy-4-methoxymethyl-4,5-dihydro-1H-pyrazole-1-carboxamide N-(4-trifluoromethylphenyl)-3-(3-chloro-4-trifluoromethylphenyl)-4-carboethoxy-4-methyl-4,5-dihydro-1H-pyrazole-1-carboxamide N-(4-trifluoromethylphenyl)-3-(3-chloro-4-trifluoromethylphenyl)-4-carboethoxy-4-methyl-N-(2-methoxyethylsulfenyl)-4,5-dihydro-1H-pyrazole-1-carboxamide N-(4-trifluoromethylphenyl)-3-(3-chloro-4-trifluoromethylphenyl)-4-carboethoxy-4-methyl-N-(2-nitrophenylsulfenyl)-4,5-dihydro-1H-pyrazole-1-carboxamide N-(4-trifluoromethylphenyl)-3-(3-chloro-4-trifluoromethylphenyl)-4-carboethoxy-4-methyl-N-acetyl-4,5-dihydro-1H-pyrazole-1-carboxamide N-(4-trifluoromethylphenyl)-3-(3-chloro-4-trifluoromethylphenyl)-4-carboethoxy-4-methyl-N-carboethoxy-4,5-dihydro-1-H-pyrazole-1-carboxamide N-(4-trifluoromethylphenyl)-3-(3-chloro-4-trifluoromethylphenyl)-4-carboethoxy-4-methyl-N-carbomethoxy-4,5-dihydro-1H-pyrazole-1-carboxamide N-(4-trifluoromethylphenyl)-3-(3-chloro-4-trifluoromethylphenyl)-4-carboethoxy-4-methyl-N-carbomethoxycarbonyl-4,5-dihydro-1-H-pyrazole-1-carboxamide N-(4-trifluoromethylphenyl)-3-(3-chloro-4-trifluoromethylphenyl)-4-carboethoxy-4-methyl-N-carbomethoxysulfenyl-4,5-dihydro-1H-pyrazole-1-carboxamide N-(4-trifluoromethylphenyl)-3-(3-chloro-4-trifluoromethylphenyl)-4-carboethoxy-4-methyl-N-dimethylcarbamoyl-4,5-dihydro-1H-pyrazole-1-carboxamide N-(4-trifluoromethylphenyl)-3-(3-chloro-4-trifluoromethylphenyl)-4-carboethoxy-4-methyl-N-formyl-4,5-dihydro-1H-pyrazole-1-carboxamide N-(4-trifluoromethylphenyl)-3-(3-chloro-4-trifluoromethylphenyl)-4-carboethoxy-4-methyl-N-methoxymethyl-4,5-dihydro-1H-pyrazole-1-carboxamide N-(4-trifluoromethylphenyl)-3-(3-chloro-4-trifluoromethylphenyl)-4-carboethoxy-4-methyl-N-methyl-4,5-dihydro-1H-pyrazole-1-carboxamide N-(4-trifluoromethylphenyl)-3-(3-chloro-4-trifluoromethylphenyl)-4-carboethoxy-4-methyl-N-methylsulfenyl-4,5-dihydro-1H-pyrazole-1-carboxamide N-(4-trifluoromethylphenyl)-3-(3-chloro-4-trifluoromethylphenyl)-4-carboethoxy-4-methyl-N-trifluoroacetyl-4,5-dihydro-1H-pyrazole-1-carboxamide N-(4-trifluoromethylphenyl)-3-(3-chloro-4-trifluoromethylphenyl)-4-carboethoxy-4-methylthiomethyl-4,5-dihydro-1H-pyrazole-1-carboxamide N-(4-trifluoromethylphenyl)-3-(3-chloro-4-trifluoromethylphenyl)-4-carboethoxy-4-phenyl-4,5-dihydro-1H-pyrazole-1-carboxamide N-(4-trifluoromethylphenyl)-3-(3-chloro-4-trifluoromethylphenyl)-4-methyl-4-(2-chloroally)-4,5-dihydro-1H-pyrazole-1-carboxamide
N-(4-trifluoromethylphenyl)-3-(3-chloro-4-trifluoromethylphenyl)-4-methyl-4-(2-methylthioethyl)-4,5-dihydro-1H-pyrazole-1-carboxamide
N-(4-trifluoromethylphenyl)-3-(3-chloro-4-trifluoromethylphenyl)-4-methyl-4-(3-cyanopropyl)-4,5-dihydro-1H-pyrazole-1-carboxamide
N-(4-trifluoromethylphenyl)-3-(3-chloro-4-trifluoromethylphenyl)-4-methyl-4-(4-chlorophenyl)-4,5-dihydro-1H-pyrazole-1-carboxamide
N-(4-trifluoromethylphenyl)-3-(3-chloro-4-trifluoromethylphenyl)-4-methyl-4-(4-difluoromethoxyphenyl)-4,5-dihydro-1H-pyrazole-1-carboxamide
N-(4-trifluoromethylphenyl)-3-(3-chloro-4-trifluoromethylphenyl)-4-methyl-4-(4-trifluoromethoxyphenyl)-4,5-dihydro-1H-pyrazole-1-carboxamide
N-(4-trifluoromethylphenyl)-3-(3-chloro-4-trifluoromethylphenyl)-4-methyl-4-(4-trifluoromethylphenyl)-4,5-dihydro-1H-pyrazole-1-carboxamide
N-(4-trifluoromethylphenyl)-3-(3-chloro-4-trifluoromethylphenyl)-4-methyl-4-acetyl-4,5-dihydro-1H-pyrazole-1-carboxamide
N-(4-trifluoromethylphenyl)-3-(3-chloro-4-trifluoromethylphenyl)-4-methyl-4-allyl-4,5-dihydro-1H-pyrazole-1-carboxamide
N-(4-trifluoromethylphenyl)-3-(3-chloro-4-trifluoromethylphenyl)-4-methyl-4-benzyl-4,5-dihydro-1H-pyrazole-1-carboxamide
N-(4-trifluoromethylphenyl)-3-(3-chloro-4-trifluoromethylphenyl)-4-methyl-4-carbomethoxy-4,5-dihydro-1H-pyrazole-1-carboxamide
N-(4-trifluoromethylphenyl)-3-(3-chloro-4-trifluoromethylphenyl)-4-methyl-4-ethyl-4,5-dihydro-1H-pyrazole-1-carboxamide
N-(4-trifluoromethylphenyl)-3-(3-chloro-4-trifluoromethylphenyl)-4-methyl-4-methallyl-4,5-dihydro-1H-pyrazole-1-carboxamide
N-(4-trifluoromethylphenyl)-3-(3-chloro-4-trifluoromethylphenyl)-4-methyl-4-methoxymethyl-4,5-dihydro-1H-pyrazole-1-carboxamide
N-(4-trifluoromethylphenyl)-3-(3-chloro-4-trifluoromethylphenyl)-4-methyl-4-methylthiomethyl-4,5-dihydro-1H-pyrazole-1-carboxamide
N-(4-trifluoromethylphenyl)-3-(3-chloro-4-trifluoromethylphenyl)-4-methyl-4-phenyl-4,5-dihydro-1H-pyrazole-1-carboxamide
N-(4-trifluoromethylphenyl)-3-(3-chloro-4-trifluoromethylphenyl)-4-phenyl-4-(2-chloroallyl)-4,5-dihydro-1H-pyrazole-1-carboxamide
N-(4-trifluoromethylphenyl)-3-(3-chloro-4-trifluoromethylphenyl)-4-phenyl-4-(2-methylthioethyl)-4,5-dihydro-1H-pyrazole-1-carboxamide
N-(4-trifluoromethylphenyl)-3-(3-chloro-4-trifluoromethylphenyl)-4-phenyl-4-(3-cyanopropyl)-4,5-dihydro-1H-pyrazole-1-carboxamide
N-(4-trifluoromethylphenyl)-3-(3-chloro-4-trifluoromethylphenyl)-4-phenyl-4-(4-chlorophenyl)-4,5-dihydro-1H-pyrazole-1-carboxamide
N-(4-trifluoromethylphenyl)-3-(3-chloro-4-trifluoromethylphenyl)-4-phenyl-4-(4-difluoromethoxyphenyl)-4,5-dihydro-1H-pyrazole-1-carboxamide
N-(4-trifluoromethylphenyl)-3-(3-chloro-4-trifluoromethylphenyl)-4-phenyl-4-(4-trifluoromethoxyphenyl)-4,5-dihydro-1H-pyrazole-1-carboxamide
N-(4-trifluoromethylphenyl)-3-(3-chloro-4-trifluoromethylphenyl)-4-phenyl-4-(4-trifluoromethylphenyl)-4,5-dihydro-1H-pyrazole-1-carboxamide
N-(4-trifluoromethylphenyl)-3-(3-chloro-4-trifluoromethylphenyl)-4-phenyl-4-acetyl-4,5-dihydro-1H-pyrazole-1-carboxamide
N-(4-trifluoromethylphenyl)-3-(3-chloro-4-trifluoromethylphenyl)-4-phenyl-4-allyl-4,5-dihydro-1H-pyrazole-1-carboxamide
N-(4-trifluoromethylphenyl)-3-(3-chloro-4-trifluoromethylphenyl)-4-phenyl-4-benzyl-4,5-dihydro-1H-pyrazole-1-carboxamide
N-(4-trifluoromethylphenyl)-3-(3-chloro-4-trifluoromethylphenyl)-4-phenyl-4-carbomethoxy-4,5-dihydro-1H-pyrazole-1-carboxamide
N-(4-trifluoromethylphenyl)-3-(3-chloro-4-trifluoromethylphenyl)-4-phenyl-4-ethyl-4,5-dihydro-1H-pyrazole-1-carboxamide
N-(4-trifluoromethylphenyl)-3-(3-chloro-4-trifluoromethylphenyl)-4-phenyl-4-methallyl-4,5-dihydro-1H-pyrazole-1-carboxamide
N-(4-trifluoromethylphenyl)-3-(3-chloro-4-trifluoromethylphenyl)-4-phenyl-4-methoxymethyl-4,5-dihydro-1H-pyrazole-1-carboxamide
N-(4-trifluoromethylphenyl)-3-(3-chloro-4-trifluoromethylphenyl)-4-phenyl-4-methyl-4,5-dihydro-1H-pyrazole-1-carboxamide
N-(4-trifluoromethylphenyl)-3-(3-chloro-4-trifluoromethylphenyl)-4-phenyl-4-methyl-N-(2-methoxyethylsulfenyl)-4,5-dihydro-1H-pyrazole-1-carboxamide
N-(4-trifluoromethylphenyl)-3-(3-chloro-4-trifluoromethylphenyl)-4-phenyl-4-methyl-N-(2-nitrophenylsulfenyl)-4,5-dihydro-1H-pyrazole-1-carboxamide
N-(4-trifluoromethylphenyl)-3-(3-chloro-4-trifluoromethylphenyl)-4-phenyl-4-methyl-N-acetyl-4,5-dihydro-1H-pyrazole-1-carboxamide
N-(4-trifluoromethylphenyl)-3-(3-chloro-4-trifluoromethylphenyl)-4-phenyl-4-methyl-N-carboethoxy-4,5-dihydro-1H-pyrazole-1-carboxamide
N-(4-trifluoromethylphenyl)-3-(3-chloro-4-trifluoromethylphenyl)-4-phenyl-4-methyl-N-carbomethoxy-4,5-dihydro-1H-pyrazole-1-carboxamide
N-(4-trifluoromethylphenyl)-3-(3-chloro-4-trifluoromethylphenyl)-4-phenyl-4-methyl-N-carbomethoxycarbonyl-4,5-dihydro-1H-pyrazole-1-carboxamide
N-(4-trifluoromethylphenyl)-3-(3-chloro-4-trifluoromethylphenyl)-4-phenyl-4-methyl-N-carbomethoxysulfenyl-4,5-dihydro-1H-pyrazole-1-carboxamide
N-(4-trifluoromethylphenyl)-3-(3-chloro-4-trifluoromethylphenyl)-4-phenyl-4-methyl-N-dimethylcarbamoyl-4,5-dihydro-1H-pyrazole-1-carboxamide
N-(4-trifluoromethylphenyl)-3-(3-chloro-4-trifluoromethylphenyl)-4-phenyl-4-methyl-N-formyl-4,5-dihydro-1H-pyrazole-1-carboxamide
N-(4-trifluoromethylphenyl)-3-(3-chloro-4-trifluoromethylphenyl)-4-phenyl-4-methyl-N-methoxymethyl-4,5-dihydro-1H-pyrazole-1-carboxamide
N-(4-trifluoromethylphenyl)-3-(3-chloro-4-trifluoromethylphenyl)-4-phenyl-4-methyl-N-methyl-4,5-dihydro-1H-pyrazole-1-carboxamide
N-(4-trifluoromethylphenyl)-3-(3-chloro-4-trifluoromethylphenyl)-4-phenyl-4-methyl-N-methylsulfenyl-4,5-dihydro-1H-pyrazole-1-carboxamide
N-(4-trifluoromethylphenyl)-3-(3-chloro-4-trifluoromethylphenyl)-4-phenyl-4-methyl-N-trifluoroacetyl-4,5-dihydro-1H-pyrazole-1-carboxamide N-(4-trifluoromethylphenyl)-3-(3-chloro-4-trifluoromethylphenyl)-4-phenyl-4-methylthiomethyl-4,5-dihydro-1H-pyrazole-1-carboxamide
N-(4-trifluoromethylphenyl)-3-(4-chlorophenyl)-4-(3-methylthiopropyl)-4-acetyl-4,5-dihydro-1H-pyrazole-1-carboxamide
N-(4-trifluoromethylphenyl)-3-(4-chlorophenyl)-4-(3-methylthiopropyl)-4-carbomethoxy-4,5-dihydro-1H-pyrazole-1-carboxamide
N-(4-trifluoromethylphenyl)-3-(4-chlorophenyl)-4-(3-methylthiopropyl)-4-ethyl-4,5-dihydro-1H-pyrazole-1-carboxamide
N-(4-trifluoromethylphenyl)-3-(4-chlorophenyl)-4-(3-methylthiopropyl)-4-methyl-4,5-dihydro-1H-pyrazole-1-carboxamide
N-(4-trifluoromethylphenyl)-3-(4-chlorophenyl)-4-(3-methylthiopropyl)-4-methyl-N-(2-methoxyethylsulfenyl)-4,5-dihydro-1H-pyrazole-1-carboxamide
N-(4-trifluoromethylphenyl)-3-(4-chlorophenyl)-4-(3-methylthiopropyl)-4-methyl-N-(2-nitrophenylsulfenyl)-4,5-dihydro-1H-pyrazole-1-carboxamide
N-(4-trifluoromethylphenyl)-3-(4-chlorophenyl)-4-(3-methylthiopropyl)-4-methyl-N-acetyl-4,5-dihydro-1H-pyrazole-1-carboxamide
N-(4-trifluoromethylphenyl)-3-(4-chlorophenyl)-4-(3-methylthiopropyl)-4-methyl-N-carboethoxy-4,5-dihydro-1H-pyrazole-1-carboxamide
N-(4-trifluoromethylphenyl)-3-(4-chlorophenyl)-4-(3-methylthiopropyl)-4-methyl-N-carbomethoxy-4,5-dihydro-1H-pyrazole-1-carboxamide
N-(4-trifluoromethylphenyl)-3-(4-chlorophenyl)-4-(3-methylthiopropyl)-4-methyl-N-carbomethoxycarbonyl)-4,5-dihydro-1H-pyrazole-1-carboxamide
N-(4-trifluoromethylphenyl)-3-(4-chlorophenyl)-4-(3-methylthiopropyl)-4-methyl-N-carbomethoxysulfenyl-4,5-dihydro-1H-pyrazole-1-carboxamide
N-(4-trifluoromethylphenyl)-3-(4-chlorophenyl)-4-(3-methylthiopropyl)-4-methyl-N-dimethylcarbamoyl-4,5-dihydro-1H-pyrazole-1-carboxamide
N-(4-trifluoromethylphenyl)-3-(4-chlorophenyl)-4-(3-methylthiopropyl)-4-methyl-N-formyl-4,5-dihydro-1H-pyrazole-1-carboxamide
N-(4-trifluoromethylphenyl)-3-(4-chlorophenyl)-4-(3-methylthiopropyl)-4-methyl-N-methoxymethyl-4,5-dihydro-1H-pyrazole-1-carboxamide
N-(4-trifluoromethylphenyl)-3-(4-chlorophenyl)-4-(3-methylthiopropyl)-4-methyl-N-methyl-4,5-dihydro-1H-pyrazole-1-carboxamide
N-(4-trifluoromethylphenyl)-3-(4-chlorophenyl)-4-(3-methylthiopropyl)-4-methyl-N-methylsulfenyl-4,5-dihydro-1H-pyrazole-1-carboxamide
N-(4-trifluoromethylphenyl)-3-(4-chlorophenyl)-4-(3-methylthiopropyl)-4-methyl-N-trifluoroacetyl-4,5-dihydro-1H-pyrazole-1-carboxamide
N-(4-trifluoromethylphenyl)-3-(4-chlorophenyl)-4-carboethoxy-4-(2-chloroallyl)-4,5-dihydro-1H-pyrazole-1-carboxamide
N-(4-trifluoromethylphenyl)-3-(4-chlorophenyl)-4-carboethoxy-4-(2-methylthioethyl)-4,5-dihydro-1H-pyrazole-1-carboxamide
N-(4-trifluoromethylphenyl)-3-(4-chlorophenyl)-4-carboethoxy-4-(3-cyanopropyl)-4,5-dihydro-1H-pyrazole-1-carboxamide
N-(4-trifluoromethylphenyl)-3-(4-chlorophenyl)-4-carboethoxy-4-(4-chlorophenyl)-4,5-dihydro-1H-pyrazole-1-carboxamide
N-(4-trifluoromethylphenyl)-3-(4-chlorophenyl)-4-carboethoxy-4-(4-difluoromethoxyphenyl)-4,5-dihydro-1H-pyrazole-1-carboxamide
N-(4-trifluoromethylphenyl)-3-(4-chlorophenyl)-4-carboethoxy-4-(4-trifluoromethoxyphenyl)-4,5-dihydro-1H-pyrazole-1-carboxamide
N-(4-trifluoromethylphenyl)-3-(4-chlorophenyl)-4-carboethoxy-4-(4-trifluoromethylphenyl)-4,5-dihydro-1H-pyrazole-1-carboxamide
N-(4-trifluoromethylphenyl)-3-(4-chlorophenyl)-4-carboethoxy-4-acetyl-4,5-dihydro-1H-pyrazole-1-carboxamide
N-(4-trifluoromethylphenyl)-3-(4-chlorophenyl)-4-carboethoxy-4-allyl-4,5-dihydro-1H-pyrazole-1-carboxamide
N-(4-trifluoromethylphenyl)-3-(4-chlorophenyl)-4-carboethoxy-4-benzyl-4,5-dihydro-1H-pyrazole-1-carboxamide
N-(4-trifluoromethylphenyl)-3-(4-chlorophenyl)-4-carboethoxy-4-carbomethoxy-4,5-dihydro-1H-pyrazole-1-carboxamide
N-(4-trifluoromethylphenyl)-3-(4-chlorophenyl)-4-carboethoxy-4-ethyl-4,5-dihydro-1H-pyrazole-1-carboxamide
N-(4-trifluoromethylphenyl)-3-(4-chlorophenyl)-4-carboethoxy-4-methallyl-4,5-dihydro-1H-pyrazole-1-carboxamide
N-(4-trifluoromethylphenyl)-3-(4-chlorophenyl)-4-carboethoxy-4-methoxymethyl-4,5-dihydro-1H-pyrazole-1-carboxamide
N-(4-trifluoromethylphenyl)-3-(4-chlorophenyl)-4-carboethoxy-4-methyl-4,5-dihydro-1H-pyrazole-1-carboxamide
N-(4-trifluoromethylphenyl)-3-(4-chlorophenyl)-4-carboethoxy-4-methyl-N-(2-methoxyethylsulfenyl)-4,5-dihydro-1H-pyrazole-1-carboxamide
N-(4-trifluoromethylphenyl)-3-(4-chlorophenyl)-4-carboethoxy-4-methyl-N-(2-nitrophenylsulfenyl)-4,5-dihydro-1H-pyrazole-1-carboxamide
N-(4-trifluoromethylphenyl)-3-(4-chlorophenyl)-4-carboethoxy-4-methyl-N-acetyl-4,5-dihydro-1H-pyrazole-1-carboxamide
N-(4-trifluoromethylphenyl)-3-(4-chlorophenyl)-4-carboethoxy-4-methyl-N-carboethoxy-4,5-dihydro-1H-pyrazole-1-carboxamide
N-(4-trifluoromethylphenyl)-3-(4-chlorophenyl)-4-carboethoxy-4-methyl-N-carbomethoxy-4,5-dihydro-1H-pyrazole-1-carboxamide
N-(4-trifluoromethylphenyl)-3-(4-chlorophenyl)-4-carboethoxy-4-methyl-N-carbomethoxycarbonyl-4,5-dihydro-1H-pyrazole-1-carboxamide
N-(4-trifluoromethylphenyl)-3-(4-chlorophenyl)-4-carboethoxy-4-methyl-N-carbomethoxysulfenyl-4,5-dihydro-1H-pyrazole-1-carboxamide
N-(4-trifluoromethylphenyl)-3-(4-chlorophenyl)-4-carboethoxy-4-methyl-N-dimethylcarbamoyl-4,5-dihydro-1H-pyrazole-1-carboxamide
N-(4-trifluoromethylphenyl)-3-(4-chlorophenyl)-4-carboethoxy-4-methyl-N-formyl-4,5-dihydro-1H-pyrazole-1-carboxamide
N-(4-trifluoromethylphenyl)-3-(4-chlorophenyl)-4-carboethoxy-4-methyl-N-methoxymethyl-4,5-dihydro-1H-pyrazole-1-carboxamide
N-(4-trifluoromethylphenyl)-3-(4-chlorophenyl)-4-carboethoxy-4-methyl-N-methyl-4,5-dihydro-1H-pyrazole-1-carboxamide N-(4-trifluoromethylphenyl)-3-(4-chlorophenyl)-4-carboethoxy-4-methyl-N-methylsulfenyl-4,5-dihydro-1H-pyrazole-1-carboxamide N-(4-trifluoromethylphenyl)-3-(4-chlorophenyl)-4-carboethoxy-4-methyl-N-trifluoroacetyl-4,5-dihydro-1H-pyrazole-1-carboxamide N-(4-trifluoromethylphenyl)-3-(4-chlorophenyl)-4-carboethoxy-4-methylthiomethyl-4,5-dihydro-1H-pyrazole-1-carboxamide N-(4-trifluoromethylphenyl)-3-(4-chlorophenyl)-4-carboethoxy-4-phenyl-4,5-dihydro-1H-pyrazole-1-carboxamide N-(4-trifluoromethylphenyl)-3-(4-chlorophenyl)-4-carbomethoxy-4-methyl-4,5-dihydro-1H-pyrazole-1-carboxamide N-(4-trifluoromethylphenyl)-3-(4-chlorophenyl)-4-dimethylcarbamoyl-4-methyl-4,5-dihydro-1H-pyrazole-1-carboxamide N-(4-trifluoromethylphenyl)-3-(4-chlorophenyl)-4-methyl-4-(2-chloroallyl)-4,5-dihydro-1H-pyrazole-1-carboxamide N-(4-trifluoromethylphenyl)-3-(4-chlorophenyl)-4-methyl-4-(2-methylthioethyl)-4,5-dihydro-1H-pyrazole-1-carboxamide N-(4-trifluoromethylphenyl)-3-(4-chlorophenyl)-4-methyl-4-(3-cyanopropyl)-4,5-dihydro-1H-pyrazole-1-carboxamide N-(4-trifluoromethylphenyl)-3-(4-chlorophenyl)-4-methyl-4-(4-chlorophenyl)-4,5-dihydro-1H-pyrazole-1-carboxamide N-(4-trifluoromethylphenyl)-3-(4-chlorophenyl)-4-methyl-4-(4-difluoromethoxyphenyl)-4,5-dihydro-1H-pyrazole-1-carboxamide N-(4-trifluoromethylphenyl)-3-(4-chlorophenyl)-4-methyl-4-(4-trifluoromethoxyphenyl)-4,5-dihydro-1H-pyrazole-1-carboxamide N-(4-trifluoromethylphenyl)-3-(4-chlorophenyl)-4-methyl-4-(4-trifluoromethylphenyl)-4,5-dihydro-1H-pyrazole-1-carboxamide N-(4-trifluoromethylphenyl)-3-(4-chlorophenyl)-4-methyl-4-acetyl-4,5-dihydro-1H-pyrazole-1-carboxamide N-(4-trifluoromethylphenyl)-3-(4-chlorophenyl)-4-methyl-4-allyl-4,5-dihydro-1H-pyrazole-1-carboxamide N-(4-trifluoromethylphenyl)-3-(4-chlorophenyl)-4-methyl-4-benzyl-4,5-dihydro-1H-pyrazole-1-carboxamide N-(4-trifluoromethylphenyl)-3-(4-chlorophenyl)-4-methyl-4-carbomethoxy-4,5-dihydro-1H-pyrazole-1-carboxamide N-(4-trifluoromethylphenyl)-3-(4-chlorophenyl)-4-methyl-4-ethyl-4,5-dihydro-1H-pyrazole-1carboxamide N-(4-trifluoromethylphenyl)-3-(4-chlorophenyl)-4-methyl-4-methallyl-4,5-dihydro-1H-pyrazole-1-carboxamide N-(4-trifluoromethylphenyl)-3-(4-chlorophenyl)-4-methyl-4-methoxymethyl-4,5-dihydro-1H-pyrazole-1-carboxamide N-(4-trifluoromethylphenyl)-3-(4-chlorophenyl)-4-methyl-4-methylthiomethyl-4,5-dihydro-1H-pyrazole-1-carboxamide N-(4-trifluoromethylphenyl)-3-(4-chlorophenyl)-4-methyl-4-phenyl-4,5-dihydro-1H-pyrazole-1-carboxamide N-(4-trifluoromethylphenyl)-3-(4-chlorophenyl)-4-phenyl-4-(2-chloroallyl)-4,5-dihydro-1H-pyrazole-1-carboxamide N-(4-trifluoromethylphenyl)-3-(4-chlorophenyl)-4-phenyl-4-(2-methylthioethyl)-4,5-dihydro-1H-pyrazole-1-carboxamide N-(4-trifluoromethylphenyl)-3-(4-chlorophenyl)-4-phenyl-4-(3-cyanopropyl)-4,5-dihydro-1H-pyrazole-1-carboxamide N-(4-trifluoromethylphenyl)-3-(4-chlorophenyl)-4-phenyl-4-(4-chlorophenyl)-4,5-dihydro-1H-pyrazole-1-carboxamide N-(4-trifluoromethylphenyl)-3-(4-chlorophenyl)-4-phenyl-4-(4-difluoromethoxyphenyl)-4,5-dihydro-1H-pyrazole-1-carboxamide N-(4-trifluoromethylphenyl)-3-(4-chlorophenyl)-4-phenyl-4-trifluoromethoxyphenyl)-4,5-dihydro-1H-pyrazole-1-carboxamide N-(4-trifluoromethylphenyl)-3-(4-chlorophenyl)-4-phenyl-4-(4-trifluoromethylphenyl)-4,5-dihydro-1H-pyrazole-1-carboxamide N-(4-trifluoromethylphenyl)-3-(4-chlorophenyl)-4-phenyl-4-acetyl-4,5-dihydro-1H-pyrazole-1-carboxamide N-(4-trifluoromethylphenyl)-3-(4-chlorophenyl)-4-phenyl-4-allyl-4,5-dihydro-1H-pyrazole-1-carboxamide N-(4-trifluoromethylphenyl)-3-(4-chlorophenyl)-4-phenyl-4-benzyl-4,5-dihydro-1H-pyrazole-1-carboxamide N-(4-trifluoromethylphenyl)-3-(4-chlorophenyl)-4-phenyl-4-carbomethoxy-4,5-dihydro-1H-pyrazole-1-carboxamide N-(4-trifluoromethylphenyl)-3-(4-chlorophenyl)-4-phenyl-4-ethyl-4,5-dihydro-1H-pyrazole-1-carboxamide N-(4-trifluoromethylphenyl)-3-(4-chlorophenyl)-4-phenyl-4-methallyl-4,5-dihydro-1H-pyrazole-1-carboxamide N-(4-trifluoromethylphenyl)-3-(4-chlorophenyl-4-phenyl-4-methoxymethyl-4,5-dihydro-1H-pyrazole-1-carboxamide N-(4-trifluoromethylphenyl)-3-(4-chlorophenyl)-4-phenyl-4-methyl-4,5-dihydro-1H-pyrazole-1-carboxamide N-(4-trifluoromethylphenyl)-3-(4-chlorophenyl)-4-phenyl-4-methyl-N-(2-methoxyethylsulfenyl)-4,5-dihydro-1H-pyrazole-1-carboxamide N-(4-trifluoromethylphenyl)-3-(4-chlorophenyl)-4-phenyl-4-methyl-N-(2-nitrophenylsulfenyl)-4,5-dihydro-1H-pyrazole-1-carboxamide N-(4-trifluoromethylphenyl)-3-(4-chlorophenyl)-4-phenyl-4-methyl-N-acetyl-4,5-dihydro-1H-pyrazole-1-carboxamide N-(4-trifluoromethylphenyl)-3-(4-chlorophenyl)-4-phenyl-4-methyl-N-carboethoxy-4,5-dihydro-1H-pyrazole-1-carboxamide N-(4-trifluoromethylphenyl)-3-(4-chlorophenyl)-4-phenyl-4-methyl-N-carbomethoxy-4,5-dihydro-1H-pyrazole-1-carboxamide N-(4-trifluoromethylphenyl)-3-(4-chlorophenyl)-4-phenyl-4-methyl-N-carbomethoxycarbonyl-4,5-dihydro-1H-pyrazole-1-carboxamide N-(4-trifluoromethylphenyl)-3-(4-chlorophenyl)-4-phenyl-4-methyl-N-carbomethoxysulfenyl-4,5-dihydro-1H-pyrazole-1-carboxamide N-(4-trifluoromethylphenyl)-3-(4-chlorophenyl)-4-phenyl-4-methyl-N-dimethylcarbamoyl-4,5-dihydro-1H-pyrazole-1-carboxamide N-(4-trifluoromethylphenyl)-3-(4-chlorophenyl)-4-phenyl-4-methyl-N-formyl-4,5-dihydro-1H-pyrazole-1-carboxamide N-(4-trifluoromethylphenyl)-3-(4-chlorophenyl)-4-phenyl-4-methyl-N-methoxymethyl-4,5-dihydro-1H-pyrazole-1-carboxamide N-(4-trifluoromethylphenyl)-3-(4-chlorophenyl)-4-phenyl-4-methyl-N-methyl-4,5-dihydro-1H-pyrazole-1-carboxamide N-(4-trifluoromethylphenyl)-3-(4-chlorophenyl)-4-phenyl-4-methyl-N-methylsulfenyl-4,5-dihydro-1H-pyrazole-1-carboxamide N-(4-trifluoromethylphenyl)-3-(4-chlorophenyl)-4-phenyl-4-methyl-N-trifluoroacetyl-4,5-dihydro-1H-pyrazole-1-carboxamide N-(4-trifluoromethylphenyl)-3-(4-chlorophenyl)-4-phenyl-4-methylthiomethyl-4,5-dihydro-1H-pyrazole-1-carboxamide N-(4-trifluoromethylphenyl)-3-phenyl-4-carboethoxy-4,5-dihydro-1H-pyrazole-1-carboxamide N-(4-trifluoromethylphenyl)-3-phenyl-4-carbomethoxy-4-methyl-4,5-dihydro-1H-pyrazole-1-carboxamide N-(4-trifluoromethylphenyl)-3-phenyl-4-dimethylcarbamoyl-4,5-dihydro-1H-pyrazole-1-carboxamide N-phenyl-3-(3-chloro-4-trifluoromethylphenyl)-4-(3-methylthiopropyl)-4-methyl-4,5-dihydro-1H-pyrazole-1-carboxamide N-phenyl-3-(3-chloro-4-trifluoromethylphenyl)-4-carboethoxy-4-methyl-4,5-dihydro-1H-pyrazole-1-carboxamide N-phenyl-3-(3-chloro-4-trifluoromethylphenyl)-4-phenyl-4-methyl-4,5-dihydro-1H-pyrazole-1-carboxamide N-phenyl-3-(4-chlorophenyl)-4-(3-methylthiopropyl)-4-methyl-4,5-dihydro-1H-pyrazole-1-carboxamide N-phenyl-3-(4-chlorophenyl)-4-carboethoxy-4-methyl-4,5-dihydro-1H-pyrazole-1-carboxamide N-phenyl-3-(4-chlorophenyl)-4-carbomethoxy-4-methyl-4,5-dihydro-1H-pyrazole-1-carboxamide N-phenyl-3-(4-chlorophenyl)-4-phenyl-4-methyl-4,5-dihydro-1H-pyrazole-1-carboxamide

GROUP B

N-(3,4-dichlorophenyl)-3-(4-chlorophenyl)-4-carbomethoxy-4-methyl-4,5-dihydro-1H-pyrazole N-(3,4-dichlorophenyl)-3-phenyl-4-carbomethoxy-4-methyl-4,5-dihydro-1H-pyrazole-1-carboxamide N,3-bis-(4-bromophenyl)-4-carbomethoxy-4-methyl-4,5-dihydro-1H-pyrazole-1-carboxamide N,3-bis-(4-chlorophenyl)-4-(4-chlorobenzoyl)-4-methyl-4,5-dihydro-1H-pyrazole-1-carboxamide N,3-bis-(4-chlorophenyl)-4-acetyl-4-methyl-4,5-dihydro-1H-pyrazole-1-carboxamide N,3-bis-(4-chlorophenyl)-4-acetyl-4-phenyl-4,5-dihydro-1H-pyrazole-1-carboxamide N,3-bis-(4-chlorophenyl)-4-benzoyl-4-methyl-4,5-dihydro-1H-pyrazole-1-carboxamide N,3-bis-(4-chlorophenyl)-4-carbo(2-dimethylaminoethoxy)-4-methyl-4,5-dihydro-1H-pyrazole-1-carboxamide N,3-bis-(4-chlorophenyl)-4-carbo(2-dimethylaminoethoxy)-4-methyl-4,5-dihydro-1H-pyrazole-1-carboxamide hydrochloride salt N,3-bis-(4-chlorophenyl)-4-carbo(2-methylsulfonylethoxy)-4-methyl-4,5-dihydro-1H-pyrazole-1-carboxamide N,3-bis-(4-chlorophenyl)-4-carbo(2-methylthioethoxy)-4-methyl-4,5-dihydro-1H-pyrazole-1-carboxamide N,3-bis-(4-chlorophenyl)-4-carbobutoxy-4-methyl-4,5-dihydro-1H-pyrazole-1-carboxamide N,3-bis-(4-chlorophenyl)-4-carboethoxy-4,5-dihydro-1H-pyrazole-1-carboxamide N,3-bis-(4-chlorophenyl)-4-carboethoxy-4-methyl-4,5-dihydro-1H-pyrazole-1-carboxamide N,3-bis-(4-chlorophenyl)-4-carboisopropoxy-4-methyl-4,5-dihydro-1H-pyrazole-1-carboxamide N,3-bis-(4-chlorophenyl)-4-carbomethyloxy-4-methyl-4,5-dihydro-1H-pyrazole-1-carboxamide N,3-bis-(4-chlorophenyl)-4-carbomethoxy-4,5-dihydro-1H-pyrazole-1-carboxamide N,3-bis-(4-chlorophenyl)-4-carbomethoxy-4-ethyl-4,5-dihydro-1H-pyrazole-1-carboxamide N,3-bis-(4-chlorophenyl)-4-carbomethoxy-4-methyl-4,5-dihydro-1H-pyrazole-1-carboxamide N,3-bis-(4-chlorophenyl)-4-carbomethoxy-4-methyl-4,5-dihydro-1H-pyrazole-1-carboxthioamide N,3-bis-(4-chlorophenyl)-4-carbomethoxy-4-methyl-N-acetyl-4,5-dihydro-1H-pyrazole-1-carboxamide N,3-bis-(4-chlorophenyl)-4-carbomethoxy-4-phenyl-4,5-dihydro-1H-pyrazole-1-carboxamide N,3-bis-(4-chlorophenyl)-4-carbomethoxy-N,4-dimethyl-4,5-dihydro-1H-pyrazole-1-carboxamide N,3-bis-(4-chlorophenyl)-4-carbomethoxy-N-(1-carbomethoxy-prop-2-yl-thio)-4-methyl-4,5-dihydro-1H-pyrazole-1-carboxamide N,3-bis-(4-chlorophenyl)-4-carbomethoxy-N-(2-nitrophenylsulfenyl)-4-methyl-4,5-dihydro-1H-pyrazole-1-carboxamide N,3-bis-(4-chlorophenyl)-4-carbomethoxy-N-(3-cyanopropylthio)-4-methyl-4,5-dihydro-1H-pyrazole-1-carboxamide N,3-bis-(4-chlorophenyl)-4-carbomethoxy-N-acetyl-4-methyl-4,5-dihydro-1H-pyrazole-1-carboxthioamide N,3-bis-(4-chlorophenyl)-4-carbomethoxy-N-carboethoxy-4-methyl-4,5-dihydro-1H-pyrazole-1-carboxamide N,3-bis-(4-chlorophenyl)-4-carbomethoxy-N-carbomethoxythio-4-methyl-4,5-dihydro-1H-pyrazole-1-carboxamide N,3-bis-(4-chlorophenyl)-4-carbomethoxy-N-carbophenoxy-4-methyl-4,5-dihydro-1H-pyrazole-1-carboxamide N,3-bis-(4-chlorophenyl)-4-carbomethoxy-N-carbovinyloxy-4-methyl-4,5-dihydro-1H-pyrazole-1-carboxamide N,3-bis-(4-chlorophenyl)-4-carbomethoxy-N-dimethylcarbamoyl-4-methyl-4,5-dihydro-1H-pyrazole-1-carboxamide N,3-bis-(4-chlorophenyl)-4-carbomethoxy-N-formyl-4-methyl-4,5-dihydro-1H-pyrazole-1-carboxamide N,3-bis-(4-chlorophenyl)-4-carbomethoxy-N-methoxymethyl-4-methyl-4,5-dihydro-1H-pyrazole-1-carboxamide N,3-bis-(4-chlorophenyl)-4-carbomethoxy-N-methyloxallyl-4-methyl-4,5-dihydro-1H-pyrazole-1-carboxamide N,3-bis-(4-chlorophenyl)-4-carbomethoxy-N-methylthio-4-methyl-4,5-dihydro-1H-pyrazole-1-carboxamide N,3-bis-(4-chlorophenyl)-4-carbomethoxy-N-phenylthio-4-methyl-4,5-dihydro-1H-pyrazole-1-carboxamide N,3-bis-(4-chlorophenyl)-4-carbomethoxy-N-propylthio-4-methyl-4,5-dihydro-1H-pyrazole-1-carboxamide N,3-bis-(4-chlorophenyl)-4-carbomethoxy-N-trifluoroacetyl-4-methyl-4,5-dihydro-1H-pyrazole-1-carboxamide N,3-bis-(4-chlorophenyl)-4-carbomethylthiomethoxy-4-methyl-4,5-dihydro-1H-pyrazole-1-carboxamide N,3-bis-(4-chlorophenyl)-4-carbopropoxy-4-methyl-4,5-dihydro-1H-pyrazole-1-carboxamide N,3-bis-(4-chlorophenyl)-4-carboxy-4,5-dihydro-1H-pyrazole-1-carboxamide N,3-bis-(4-chlorophenyl)-4-carboxy-4-methyl-4,5-dihydro-1H-pyrazole-1-carboxamide N,3-bis-(4-chlorophenyl)-4-carboxy-4-methyl-4,5-dihydro-1H-pyrazole-1-carboxamide sodium salt N,3-bis-(4-chlorophenyl)-4-carboxy-4-phenyl-4,5-dihydro-1H-pyrazole-1-carboxamide N,3-bis-(4-chlorophenyl)-4-diethylcarboxamido-4-methyl-4,5-dihydro-1H-pyrazole-1-carboxamide N,3-bis-(4-chlorophenyl)-4-dimethylcarbamoyl-4,5-dihydro-1H-pyrazole-1-carboxamide N,3-bis-(4-chlorophenyl)-4-dimethylcarboxamido-4-methyl-4,5-dihydro-1H-pyrazole-1-carboxamide N,3-bis-(4-chlorophenyl)-4-dimethylthiocarbamoyl-4-methyl-4,5-dihydro-1H-pyrazole-1-carboxamide N,3-bis-(4-chlorophenyl)-4-isobutyryl-4,5-dihydro-1H-pyrazole-1-carboxamide N,3-bis-(4-chlorophenyl)-4-methylthiothiocarbonyl-4-methyl-4,5-dihydro-1H-pyrazole-1-carboxamide N,3-bis-(4-chlorophenyl)-4-pivaloyl-4-methyl-4,5-dihydro-1H-pyrazole-1-carboxamide N,3-bis-(4-chlorophenyl)-4-propionyl-4-methyl-4,5-dihydro-1H-pyrazole-1-carboxamide N,3-bis-(4-trifluoromethylphenyl)-4-carbomethoxy-4-methyl-4,5-dihydro-1H-pyrazole-1-carboxamide N-(1-naphthyl)-3-(4-chlorophenyl)-4-carbomethoxy-4,5-dihydro-1H-pyrazole-1-carboxamide N-(2,4-dinitrophenyl)-3-(4-chlorophenyl)-4-carbomethoxy-4,5-dihydro-1H-pyrazole-1-carboxamide N-(2-fluoro-4-trifluoromethylphenyl)-3-(3-chloro-4-trifluoromethylphenyl)-4-carboethoxy-4-methyl-4,5-dihydro-1H-pyrazole-1-carboxamide N-(2-fluoro-4-trifluoromethylphenyl)-3-(4-chlorophenyl)-4-carboethoxy-4-methyl-4,5-dihydro-1H-pyrazole-1-carboxamide N-(2-methyl-4-trifluoromethylphenyl)-3-(3-chloro-4-trifluoromethylphenyl)-4-carboethoxy-4-methyl-4,5-dihydro-1H-pyrazole-1-carboxamide N-(2-methyl-4-trifluoromethylphenyl)-3-(4-chlorophenyl)-4-carboethoxy-4-methyl-4,5-dihydro-1H-pyrazole-1-carboxamide N-(3-bromo-4-trifluoromethylphenyl)-3-(3-chloro-4-trifluoromethylphenyl)-4-carboethoxy-4-methyl-4,5-dihydro-1H-pyrazole-1-carboxamide N-(3-bromo-4-trifluoromethylphenyl)-3-(4-chlorophenyl)-4-carboethoxy-4-methyl-4,5-dihydro-1H-pyrazole-1-carboxamide N-(3-bromophenyl)-3-(3-chloro-4-trifluoromethylphenyl)-4-carboethoxy-4-methyl-4,5-dihydro-1H-pyrazole-1-carboxamide N-(3-bromophenyl)-3-(4-chlorophenyl)-4-carboethoxy-4-methyl-4,5-dihydro-1H-pyrazole-1-carboxamide N-(3-carboethoxyphenyl)-3-(3-chloro-4-trifluoromethylphenyl)-4-carboethoxy-4-methyl-4,5-dihydro-1H-pyrazole-1-carboxamide N-(3-carboethoxyphenyl)-3-(4-chlorophenyl)-4-carboethoxy-4-methyl-4,5-dihydro-1H-pyrazole-1-carboxamide N-(3-carboisopropoxyphenyl)-3-(3-chloro-4-trifluoromethylphenyl)-4-carboethoxy-4-methyl-4,5-dihydro-1H-pyrazole-1-carboxamide N-(3-carboisopropoxyphenyl)-3-(4-chlorophenyl)-4-carboethoxy-4-methyl-4,5-dihydro-1H-pyrazole-1-carboxamide N-(3-carbomethoxyphenyl)-3-(3-chloro-4-trifluoromethylphenyl)-4-carboethoxy-4-methyl-4,5-dihydro-1H-pyrazole-1-carboxamide N-(3-carbomethoxyphenyl)-3-(4-chlorophenyl)-4-carboethoxy-4-methyl-4,5-dihydro-1H-pyrazole-1-carboxamide N-(3-chloro-4-trifluoromethylphenyl)-3-(3-chloro-4-trifluoromethylphenyl)-4-carboethoxy-4-methyl-4,5-dihydro-1H-pyrazole-1-carboxamide N-(3-chloro-4-trifluoromethylphenyl)-3-(4-chlorophenyl)-4-carboethoxy-4-methyl-4,5-dihydro-1H-pyrazole-1-carboxamide N-(3-chlorophenyl)-3-(4-chlorophenyl)-4-carbomethoxy-4-methyl-4,5-dihydro-1H-pyrazole-1-carboxamide N-(3-cyano-4-trifluoromethylphenyl)-3-(3-chloro-4-trifluoromethylphenyl)-4-carboethoxy-4-methyl-4-methyl-4,5-dihydro-1H-pyrazole-1-carboxamide N-(3-cyano-4-trifluoromethylphenyl)-3-(4-chlorophenyl)-4-carboethoxy-4-methyl-4,5-dihydro-1H-pyrazole-1-carboxamide N-(3-difluoromethoxy-4-trifluoromethylphenyl)-3-(3-chloro-4-trifluoromethylphenyl)-4-carboethoxy-4-methyl-4,5-dihydro-1H-pyrazole-1-carboxamide N-(3-difluoromethoxy-4-trifluoromethylphenyl)-3-(4-chlorophenyl)-4-carboethoxy-4-methyl-4,5-dihydro-1H-pyrazole-1-carboxamide N-(3-difluoromethoxyphenyl)-3-(3-chloro-4-trifluoromethylphenyl)-4-carboethoxy-4-methyl-4,5-dihydro-1H-pyrazole-1-carboxamide N-(3-difluoromethoxyphenyl)-3-(4-chlorophenyl)-4-carboethoxy-4-methyl-4,5-dihydro-1H-pyrazole-1-carboxamide N-(3-dimethylsulfonamidophenyl)-3-(3-chloro-4-trifluoromethylphenyl)-4-carboethoxy-4-methyl-4,5-dihydro-1H-pyrazole-1-carboxamide N-(3-dimethylsulfonamidophenyl)-3-(4-chlorophenyl)-4-carboethoxy-4-methyl-4,5-dihydro-1H-pyrazole-1-carboxamide N-(3-fluoro-4-trifluoromethylphenyl)-3-(3-chloro-4-trifluoromethylphenyl)-4-carboethoxy-4-methyl-4,5-dihydro-1H-pyrazole-1-carboxamide N-(3-fluoro-4-trifluoromethylphenyl)-3-(4-chlorophenyl)-4-carboethoxy-4-methyl-4,5-dihydro-1H-pyrazole-1-carboxamide N-(3-methoxy-4-trifluoromethylphenyl)-3-(3-chloro-4-trifluoromethylphenyl)-4-carboethoxy-4-methyl-4,5-dihydro-1H-pyrazole-1-carboxamide N-(3-methoxy-4-trifluoromethylphenyl)-3-(4-chlorophenyl)-4-carboethoxy-4-methyl-4,5-dihydro-1H-pyrazole-1-carboxamide N-(3-methyl-4-trifluoromethylphenyl)-3-(3-chloro-4-trifluoromethylphenyl)-4-carboethoxy-4-methyl-4,5-dihydro-1H-pyrazole-1-carboxamide N-(3-methyl-4-trifluoromethylphenyl)-3-(4-chlorophenyl)-4-carboethoxy-4-methyl-4,5-dihydro-1H-pyrazole-1-carboxamide N-(3-methylthiophenyl)-3-(4-chlorophenyl)-4-carbomethoxy-4-methyl-4,5-dihydro-1H-pyrazole-1-carboxamide N-(3-methylsulfonyl-4-trifluoromethylphenyl)-3-(3-chloro-4-trifluoromethylphenyl)-4-carboethoxy-4-methyl-4,5-dihydro-1H-pyrazole-1-carboxamide N-(3-methylsulfonyl-4-trifluoromethylphenyl)-3-(4-chlorophenyl)-4-carboethoxy-4-methyl-4,5-dihydro-1H-pyrazole-1-carboxamide N-(3-methylsulfonylphenyl)-3-(3-chloro-4-trifluoromethylphenyl)-4-carboethoxy-4-methyl-4,5-dihydro-1H-pyrazole-1-carboxamide N-(3-methylsulfonylphenyl)-3-(4-chlorophenyl)-4-carboethoxy-4-methyl-4,5-dihydro-1H-pyrazole-1-carboxamide N-(3-methylsulfonylphenyl)-3-(4-chlorophenyl)-4-carbomethoxy-4-methyl-4,5-dihydro-1H-pyrazole-1-carboxamide N-(3-methylthio-4-trifluoromethylphenyl)-3-(3-chloro-4-trifluoromethylphenyl)-4-carboethoxy-4-methyl-4,5-dihydro-1H-pyrazole-1-carboxamide N-(3-methylthio-4-trifluoromethylphenyl)-3-(4-chlorophenyl)-4-carboethoxy-4-methyl-4,5-dihydro-1H-pyrazole-1-carboxamide N-(3-methylthiophenyl)-3-(3-chloro-4-trifluoromethylphenyl)-4-carboethoxy-4-methyl-4,5-dihydro-1H-pyrazole-1-carboxamide N-(3-methylthiophenyl)-3-(4-chlorophenyl)-4-carboethoxy-4-methyl-4,5-dihydro-1H-pyrazole-1-carboxamide N-(3-nitro-4-trifluoromethylphenyl)-3-(3-chloro-4-trifluoromethylphenyl)-4-carboethoxy-4-methyl-4,5-dihydro-1H-pyrazole-1-carboxamide N-(3-nitro-4-trifluoromethylphenyl)-3-(4-chlorophenyl)-4-carboethoxy-4-methyl-4,5-dihydro-1H-pyrazole-1-carboxamide N-(3-trifluoromethoxy-4-trifluoromethylphenyl)-3-(3-chloro-4-trifluoromethylphenyl)-4-carboethoxy-4-methyl-4,5-dihydro-1H-pyrazole-1-carboxamide N-(3-trifluoromethoxy-4-trifluoromethylphenyl)-3-(4-chlorophenyl)-4-carboethoxy-4-methyl-4,5-dihydro-1H-pyrazole-1-carboxamide N-(3-trifluoromethoxyphenyl)-3-(3-chloro-4-trifluoromethylphenyl)-4-carboethoxy-4-methyl-4,5-dihydro-1H-pyrazole-1-carboxamide N-(3-trifluoromethoxyphenyl)-3-(4-chlorophenyl)-4-carboethoxy-4-methyl-4,5-dihydro-1H-pyrazole-1-carboxamide N-(3-trifluoromethylphenyl)-3-(3-chloro-4-trifluoromethylphenyl)-4-carboethoxy-4-methyl-4,5-dihydro-1H-pyrazole-1-carboxamide N-(3-trifluoromethylphenyl)-3-(4-chlorophenyl)-4-carboethoxy-4-methyl-4,5-dihydro-1H-pyrazole-1-carboxamide N-(3-trifluoromethylphenyl)-3-(4-chlorophenyl)-4-carbomethoxy-4-methyl-4,5-dihydro-1H-pyrazole-1-carboxamide N-(4-bromo-3-methylphenyl)-3-(4-chlorophenyl)-4-carbomethoxy-4-methyl-4,5-dihydro-1H-pyrazole-1-carboxamide N-(4-bromophenyl)-3-(3-chloro-4-trifluoromethylphenyl)-4-(3-methylthiopropyl)-4-acetyl-4,5-dihydro-1H-pyrazole-1-carboxamide N-(4-bromophenyl)-3-(3-chloro-4-trifluoromethylphenyl)-4-(3-methylthiopropyl)-4-carbomethoxy-4,5-dihydro-1H-pyrazole-1-carboxamide N-(4-bromophenyl)-3-(3-chloro-4-trifluoromethylphenyl)-4-carboethoxy-4-(2-chloroallyl)-4,5-dihydro-1H-pyrazole-1-carboxamide N-(4-bromophenyl)-3-(3-chloro-4-trifluoromethylphenyl)-4-carboethoxy-4-(2-methylthioethyl)-4,5-dihydro-1H-pyrazole-1-carboxamide N-(4-bromophenyl)-3-(3-chloro-4-trifluoromethylphenyl)-4-carboethoxy-4-(3-cyanopropyl)-4,5-dihydro-1H-pyrazole-1-carboxamide N-(4-bromophenyl)-3-(3-chloro-4-trifluoromethylphenyl)-4-carboethoxy-4-(4-chlorophenyl)-4,5-dihydro-1H-pyrazole-1-carboxamide N-(4-bromophenyl)-3-(3-chloro-4-trifluoromethylphenyl)-4-carboethoxy-4-(4-dichloromethoxyphenyl)-4,5-dihydro-1H-pyrazole-1-carboxamide N-(4-bromophenyl)-3-(3-chloro-4-trifluoromethylphenyl)-4-carboethoxy-4-(4-trifluoromethoxyphenyl)-4,5-dihydro-1H-pyrazole-1-carboxamide N-(4-bromophenyl)-3-(3-chloro-4-trifluoromethylphenyl)-4-carboethoxy-4-(4-trifluoromethylphenyl)-4,5-dihydro-1H-pyrazole-1-carboxamide N-(4-bromophenyl)-3-(3-chloro-4-trifluoromethylphenyl)-4-carboethoxy-4-acetyl-4,5-dihydro-1H-pyrazole-1-carboxamide N-(4-bromophenyl)-3-(3-chloro-4-trifluoromethylphenyl)-4-carboethoxy-4-allyl-4,5-dihydro-1H-pyrazole-1-carboxamide N-(4-bromophenyl)-3-(3-chloro-4-trifluoromethylphenyl)-4-carboethoxy-4-benzyl-4,5-dihydro-1H-pyrazole-1-carboxamide N-(4-bromophenyl)-3-(3-chloro-4-trifluoromethylphenyl)-4-carboethoxy-4-carbomethoxy-4,5-dihydro-1H-pyrazole-1-carboxamide N-(4-bromophenyl)-3-(3-chloro-4-trifluoromethylphenyl)-4-carboethoxy-4-ethyl-4,5-dihydro-1H-pyrazole-1-carboxamide N-(4-bromophenyl)-3-(3-chloro-4-trifluoromethylphenyl)-4-carboethoxy-4-methallyl-4,5-dihydro-1H-pyrazole-1-carboxamide N-(4-bromophenyl)-3-(3-chloro-4-trifluoromethylphenyl)-4-carboethoxy-4-methoxymethyl-4,5-dihydro-1H-pyrazole-1-carboxamide N-(4-bromophenyl)-3-(3-chloro-4-trifluoromethylphenyl)-4-carboethoxy-4-methyl-4,5-dihydro-1H-pyrazole-1-carboxamide N-(4-bromophenyl)-3-(3-chloro-4-trifluoromethylphenyl)-4-carboethoxy-4-methyl-N-(2-methoxyethylsulfenyl)-4,5-dihydro-1H-pyrazole-1-carboxamide N-(4-bromophenyl)-3-(3-chloro-4-trifluoromethylphenyl)-4-carboethoxy-4-methyl-N-(2-nitrophenylsulfenyl)-4,5-dihydro-1H-pyrazole-1-carboxamide N-(4-bromophenyl)-3-(3-chloro-4-trifluoromethylphenyl)-4-carboethoxy-4-methyl-N-acetyl-4,5-dihydro-1H-pyrazole-1-carboxamide N-(4-bromophenyl)-3-(3-chloro-4-trifluoromethylphenyl)-4-carboethoxy-4-methyl-N-carboethoxy-4,5-dihydro-1H-pyrazole-1-carboxamide N-(4-bromophenyl)-3-(3-chloro-4-trifluoromethylphenyl)-4-carboethoxy-4-methyl-N-carbomethoxy-4,5-dihydro-1H-pyrazole-1-carboxamide N-(4-bromophenyl)-3-(3-chloro-4-trifluoromethylphenyl)-4-carboethoxy-4-methyl-N-carbomethoxycarbonyl-4,5-dihydro-1H-pyrazole-1-carboxamide N-(4-bromophenyl)-3-(3-chloro-4-trifluoromethylphenyl)-4-carboethoxy-4-methyl-N-carbomethoxysulfenyl-4,5-dihydro-1H-pyrazole-1-carboxamide N-(4-bromophenyl)-3-(3-chloro-4-trifluoromethylphenyl)-4-carboethoxy-4-methyl-N-dimethylcarbamoyl-4,5-dihydro-1H-pyrazole-1-carboxamide N-(4-bromophenyl)-3-(3-chloro-4-trifluoromethylphenyl)-4-carboethoxy-4-methyl-N-formyl-4,5-dihydro-1H-pyrazole-1-carboxamide N-(4-bromophenyl)-3-(3-chloro-4-trifluoromethylphenyl)-4-carboethoxy-4-methyl-N-methoxymethyl-4,5-dihydro-1H-pyrazole-1-carboxamide N-(4-bromophenyl)-3-(3-chloro-4-trifluoromethylphenyl)-4-carboethoxy-4-methyl-N-methyl-4,5-dihydro-1H-pyrazole-1-carboxamide N-(4-bromophenyl)-3-(3-chloro-4-trifluoromethylphenyl)-4-carboethoxy-4-methyl-N-methylsulfenyl-4,5-dihydro-1H-pyrazole-1-carboxamide N-(4-bromophenyl)-3-(3-chloro-4-trifluoromethylphenyl)-4-carboethoxy-4-methyl-N-trifluoroacetyl-4,5-dihydro-1H-pyrazole-1-carboxamide N-(4-bromophenyl)-3-(3-chloro-4-trifluoromethylphenyl)-4-carboethoxy-4-methylthiomethyl-4,5-dihydro-1H-pyrazole-1-carboxamide N-(4-bromophenyl)-3-(3-chloro-4-trifluoromethylphenyl)-4-carboethoxy-4-phenyl-4,5-dihydro-1H-pyrazole-1-carboxamide N-(4-bromophenyl)-3-(3-chloro-4-trifluoromethylphenyl)-4-methyl-4-acetyl-4,5-dihydro-1H-pyrazole-1-carboxamide N-(4-bromophenyl)-3-(3-chloro-4-trifluoromethylphenyl)-4-methyl-4-carbomethoxy-4,5-dihydro-1H-pyrazole-1-carboxamide N-(4-bromophenyl)-3-(3-chloro-4-trifluoromethylphenyl)-4-phenyl-4-acetyl-4,5-dihydro-1H-pyrazole-1-carboxamide N-(4-bromophenyl)-3-(3-chloro-4-trifluoromethylphenyl)-4-phenyl-4-carbomethoxy-4,5-dihydro-1H-pyrazole-1-carboxamide N-(4-bromophenyl)-3-(4-chlorophenyl)-4-(3-methylthiopropyl)-4-acetyl-4,5-dihydro-1H-pyrazole-1-carboxamide N-(4-bromophenyl)-3-(4-chlorophenyl)-4-(3-methylthiopropyl)-4-carbomethoxy-4,5-dihydro-1H-pyrazole-1-carboxamide N-(4-bromophenyl)-3-(4-chlorophenyl)-4-carboethoxy-4-(2-chloroallyl)-4,5-dihydro-1H-pyrazole-1-carboxamide N-(4-bromophenyl)-3-(4-chlorophenyl)-4-carboethoxy-4-(2-methylthioethyl)-4,5-dihydro-1H-pyrazole-1-carboxamide N-(4-bromophenyl)-3-(4-chlorophenyl)-4-carboethoxy-4-(3-cyanopropyl)-4,5-dihydro-1H-pyrazole-1-carboxamide N-(4-bromophenyl)-3-(4-chlorophenyl)-4-carboethoxy-4-(4-chlorophenyl)-4,5-dihydro-1H-pyrazole-1-carboxamide N-(4-bromophenyl)-3-(4-chlorophenyl)-4-carboethoxy-4-(4-difluoromethoxyphenyl)-4,5-dihydro-1H-pyrazole-1-carboxamide N-(4-bromophenyl)-3-(4-chlorophenyl)-4-carboethoxy-4-(4-trifluoromethoxyphenyl)-4,5-dihydro-1H-pyrazole-1-carboxamide N-(4-bromophenyl)-3-(4-chlorophenyl)-4-carboethoxy-4-(4-trifluoromethylphenyl)-4,5-dihydro-1H-pyrazole-1-carboxamide N-(4-bromophenyl)-3-(4-chlorophenyl)-4-carboethoxy-4-acetyl-4,5-dihydro-1H-pyrazole-1-carboxamide N-(4-bromophenyl)-3-(4-chlorophenyl)-4-carboethoxy-4-allyl-4,5-dihydro-1H-pyrazole-1-carboxamide N-(4-bromophenyl)-3-(4-chlorophenyl)-4-carboethoxy-4-benzyl-4,5-dihydro-1H-pyrazole-1-carboxamide N-(4-bromophenyl)-3-(4-chlorophenyl)-4-carboethoxy-4-carbomethoxy-4,5-dihydro-1H-pyrazole-1-carboxamide N-(4-bromophenyl)-3-(4-chlorophenyl)-4-carboethoxy-4-ethyl-4,5-dihydro-1H-pyrazole-1-carboxamide N-(4-bromophenyl)-3-(4-chlorophenyl)-4-carboethoxy-4-methallyl-4,5-dihydro-1H-pyrazole-1-carboxamide N-(4-bromophenyl)-3-(4-chlorophenyl)-4-carboethoxy-4-methoxymethyl-4,5-dihydro-1H-pyrazole-1-carboxamide N-(4-bromophenyl)-3-(4-chlorophenyl)-4-carboethoxy-4-methyl-4,5-dihydro-1H-pyrazole-1-carboxamide N-(4-bromophenyl)-3-(4-chlorophenyl)-4-carboethoxy-4-methyl-N-(2-methoxyethylsulfenyl)-4,5-dihydro-1H-pyrazole-1-carboxamide N-(4-bromophenyl)-3-(4-chlorophenyl)-4-carboethoxy-4-methyl-N-(2-nitrophenylsulfenyl)-4,5-dihydro-1H-pyrazole-1-carboxamide N-(4-bromophenyl)-3-(4-chlorophenyl)-4-carboethoxy-4-methyl-N-acetyl-4,5-dihydro-1H-pyrazole-1-carboxamide N-(4-bromophenyl)-3-(4-chlorophenyl)-4-carboethoxy-4-methyl-N-carboethoxy-4,5-dihydro-1H-pyrazole-1-carboxamide N-(4-bromophenyl)-3-(4-chlorophenyl)-4-carboethoxy-4-methyl-N-carbomethoxy-4,5-dihydro-1H-pyrazole-1-carboxamide N-(4-bromophenyl)-3-(4-chlorophenyl)-4-carboethoxy-4-methyl-N-carbomethoxycarbonyl-4,5-dihydro-1H-pyrazole-1-carboxamide N-(4-bromophenyl)-3-(4-chlorophenyl)-4-carboethoxy-4-methyl-N-carbomethoxysulfenyl-4,5-dihydro-1H-pyrazole-1-carboxamide N-(4-bromophenyl)-3-(4-chlorophenyl)-4-carboethoxy-4-methyl-N-dimethylcarbamoyl-4,5-dihydro-1H-pyrazole-1-carboxamide N-(4-bromophenyl)-3-(4-chlorophenyl)-4-carboethoxy-4-methyl-N-formyl-4,5-dihydro-1H-pyrazole-1-carboxamide N-(4-bromophenyl)-3-(4-chlorophenyl)-4-carboethoxy-4-methyl-N-methoxymethyl-4,5-dihydro-1H-pyrazole-1-carboxamide N-(4-bromophenyl)-3-(4-chlorophenyl)-4-carboethoxy-4-methyl-N-methyl-4,5-dihydro-1H-pyrazole-1-carboxamide N-(4-bromophenyl)-3-(4-chlorophenyl)-4-carboethoxy-4-methyl-N-methylsulfenyl-4,5-dihydro-1H-pyrazole-1-carboxamide N-(4-bromophenyl)-3-(4-chlorophenyl)-4-carboethoxy-4-methyl-N-trifluoroacetyl-4,5-dihydro-1H-pyrazole-1-carboxamide N-(4-bromophenyl)-3-(4-chlorophenyl)-4-carboethoxy-4-methylthiomethyl-4,5-dihydro-1H-pyrazole-1-carboxamide N-(4-bromophenyl)-3-(4-chlorophenyl)-4-carboethoxy-4-phenyl-4,5-dihydro-1H-pyrazole-1-carboxamide N-(4-bromophenyl)-3-(4-chlorophenyl)-4-carbomethoxy-4-methyl-4,5-dihydro-1H-pyrazole-1-carboxamide N-(4-bromophenyl)-3-(4-chlorophenyl)-4-methyl-4-acetyl-4,5-dihydro-1H-pyrazole-1-carboxamide N-(4-bromophenyl)-3-(4-chlorophenyl)-4-methyl-4-carbomethoxy-4,5-dihydro-1H-pyrazole-1-carboxamide N-(4-bromophenyl)-3-(4-chlorophenyl)-4-phenyl-4-acetyl-4,5-dihydro-1H-pyrazole-1-carboxamide N-(4-bromophenyl)-3-(4-chlorophenyl)-4-phenyl-4-carbomethoxy-4,5-dihydro-1H-pyrazole-1-carboxamide N-(4-bromophenyl)-3-(4-fluorophenyl)-4-carbomethoxy-4-methyl-4,5-dihydro-1H-pyrazole-1-carboxamide N-(4-bromophenyl)-3-phenyl-4-carbomethoxy-4-methyl-4,5-dihydro-1H-pyrazole-1-carboxamide N-(4-carboethoxyphenyl)-3-(3-chloro-4-trifluoromethylphenyl)-4-carboethoxy-4-methyl-4,5-dihydro-1H-pyrazole-1-carboxamide N-(4-carboethoxyphenyl)-3-(4-chlorophenyl)-4-carboethoxy-4-methyl-4,5-dihydro-1H-pyrazole-1-carboxamide N-(4-carboethoxyphenyl)-3-(4-chlorophenyl)-4-carbomethoxy-4,5-dihydro-1H-pyrazole-1-carboxamide N-(4-carboisopropoxyphenyl)-3-(3-chloro-4-trifluoromethylphenyl)-4-(3-methylthiopropyl)-4-methyl-4,5-dihydro-1H-pyrazole-1-carboxamide N-(4-carboisopropoxyphenyl)-3-(3-chloro-4-trifluoromethylphenyl)-4-carboethoxy-4-methyl-4,5-dihydro-1H-pyrazole-1-carboxamide N-(4-carboisopropoxyphenyl)-3-(3-chloro-4-trifluoromethylphenyl)-4-phenyl-4-methyl-4,5-dihydro-1H-pyrazole-1-carboxamide N-(4-carboisopropoxyphenyl)-3-(4-chlorophenyl)-4-(3-methylthiopropyl)-4-methyl-4,5-dihydro-1H-pyrazole-1-carboxamide N-(4-carboisopropoxyphenyl)-3-(4-chlorophenyl)-4-carboethoxy-4-methyl-4,5-dihydro-1H-pyrazole-1-carboxamide N-(4-carboisopropoxyphenyl)-3-(4-chlorophenyl)-4-phenyl-4-methyl-4,5-dihydro-1H-pyrazole-1-carboxamide N-(4-carbomethoxyphenyl)-3-(3-chloro-4-trifluoromethylphenyl)-4-(3-methylthiopropyl)-4-methyl-4,5-dihydro-1H-pyrazole-1-carboxamide N-(4-carbomethoxyphenyl)-3-(3-chloro-4-trifluoromethylphenyl)-4-carboethoxy-4-methyl-4,5-dihydro-1H-pyrazole-1-carboxamide N-(4-carbomethoxyphenyl)-3-(3-chloro-4-trifluoromethylphenyl)-4-phenyl-4-methyl-4,5-dihydro-1H-pyrazole-1-carboxamide N-(4-carbomethoxyphenyl)-3-(4-chlorophenyl)-4-(3-methylthiopropyl)-4-methyl-4,5-dihydro-1H-pyrazole-1-carboxamide N-(4-carbomethoxyphenyl)-3-(4-chlorophenyl)-4-carboethoxy-4-methyl-4,5-dihydro-1H-pyrazole-1-carboxamide N-(4-carbomethoxyphenyl)-3-(4-chlorophenyl)-4-carbomethoxy-4,5-dihydro-1H-pyrazole-1-carboxamide N-(4-carbomethoxyphenyl)-3-(4-chlorophenyl)-4-phenyl-4-methyl-4,5-dihydro-1H-pyrazole-1-carboxamide N-(4-chloro-3-trifluoromethylphenyl)-3-(4-chlorophenyl)-4-carbomethoxy-4-methyl-4,5-dihydro-1H-pyrazole-1-carboxamide N-(4-chlorophenyl)-3-(4-bromophenyl)-4-carbomethoxy-4-methyl-4,5-dihydro-1H-pyrazole-1-carboxamide N-(4-chlorophenyl)-3-(4-fluorophenyl)-4-carbomethoxy-4-methyl-4,5-dihydro-1H-pyrazole-1-carboxamide N-(4-chlorophenyl)-3-(4-methoxyphenyl)-4-carbomethoxy-4-methyl-4,5-dihydro-1H-pyrazole-1-carboxamide N-(4-chlorophenyl)-3-(4-methylphenyl)-4-carbomethoxy-4-methyl-4,5-dihydro-1H-pyrazole-1-carboxamide N-(4-chlorophenyl)-3-(4-methylsulfonylphenyl)-4-carbomethoxy-4-methyl-4,5-dihydro-1H-pyrazole-1-carboxamide N-(4-chlorophenyl)-3-(4-methylthiophenyl)-4-carbomethoxy-4-methyl-4,5-dihydro-1H-pyrazole-1-carboxamide N-(4-chlorophenyl)-3-(4-trifluoromethylphenyl)-4-carbomethoxy-4-methyl-4,5-dihydro-1H-pyrazole-1-carboxamide N-(4-chlorophenyl)-3-phenyl-4-carboethoxy-4-methyl-4,5-dihydro-1H-pyrazole-1-carboxamide N-(4-chlorophenyl)-3-phenyl-4-carbomethoxy-4-methyl-4,5-dihydro-1H-pyrazole-1-carboxamide N-(4-chlorophenyl)-3-phenyl-4-dimethylcarboxamido-4-methyl-4,5-dihydro-1H-pyrazole-1-carboxamide N-(4-chlorophenyl)-3-phenyl-N,4-bis-carbomethoxy-4-methyl-4,5-dihydro-1H-pyrazole-1-carboxamide N-(4-difluoromethoxyphenyl)-3-(3-chloro-4-trifluoromethylphenyl)-4-carboethoxy-4-methyl-4,5-dihydro-1H-pyrazole-1-carboxamide N-(4-difluoromethoxyphenyl)-3-(4-chlorophenyl)-4-carboethoxy-4-methyl-4,5-dihydro-1H-pyrazole-1-carboxamide N-(4-dimethylaminoxyphenyl)-3-(4-chlorophenyl)-4-carbomethoxy-4-methyl-4,5-dihydro-1H-pyrazole-1-carboxamide N-(4-dimethylsulfonamidophenyl)-3-(3-chloro-4-trifluoromethylphenyl)-4-carboethoxy-4-methyl-4,5-dihydro-1H-pyrazole-1-carboxamide N-(4-dimethylsulfonamidophenyl)-3-(4-chlorophenyl)-4-carboethoxy-4-methyl-4,5-dihydro-1H-pyrazole-1-carboxamide N-(4-fluorophenyl)-3-(4-chlorophenyl)-4-carbomethoxy-4-methyl-4,5-dihydro-1H-pyrazole-1-carboxamide N-(4-fluorophenyl)-3-(4-bromophenyl)-4-carbomethoxy-4-methyl-4,5-dihydro-1H-pyrazole-1-carboxamide N-(4-fluorophenyl)-3-(4-fluorophenyl)-4-carbomethoxy-4-methyl-4,5-dihydro-1H-pyrazole-1-carboxamide N-(4-fluorophenyl)-3-phenyl-4-carbomethoxy-4-methyl-4,5-dihydro-1H-pyrazole-1-carboxamide N-(4-iodophenyl)-3-(4-chlorophenyl)-4-carbomethoxy-4-methyl-4,5-dihydro-1H-pyrazole-1-carboxamide N-(4-methoxyphenyl)-3-(4-chlorophenyl)-4-carbomethoxy-4-methyl-4,5-dihydro-1H-pyrazole-1-carboxamide N-(4-methylphenyl)-3-(4-chlorophenyl)-4-carbomethoxy-4-methyl-4,5-dihydro-1H-pyrazole-1-carboxamide N-(4-methylsulfonylphenyl)-3-(3-chloro-4-trifluoromethylphenyl)-4-carboethoxy-4-methyl-4,5-dihydro-1H-pyrazole-1-carboxamide N-(4-methylsulfonylphenyl)-3-(4-chlorophenyl)-4-carboethoxy-4-methyl-4,5-dihydro-1H-pyrazole-1-carboxamide N-(4-methylsulfonylphenyl)-3-(4-chlorophenyl)-4-carbomethoxy-4-methyl-4,5-dihydro-1H-pyrazole-1-carboxamide N-(4-methylsulfoxylphenyl)-3-(4-chlorophenyl)-4-carbomethoxy-4-methyl-4,5-dihydro-1H-pyrazole-1-carboxamide N-(4-methylthiophenyl)-3-(3-chloro-4-trifluoromethylphenyl)-4-carboethoxy-4-methyl-4,5-dihydro-1H-pyrazole-1-carboxamide N-(4-methylthiophenyl)-3-(4-chlorophenyl)-4-carboethoxy-4-methyl-4,5-dihydro-1H-pyrazole-1-carboxamide N-(4-methylthiophenyl)-3-(4-chlorophenyl)-4-carbomethoxy-4-methyl-4,5-dihydro-1H-pyrazole-1-carboxamide N-(4-nitrophenyl)-3-(3-chloro-4-trifluoromethylphenyl)-4-carboethoxy-4-methyl-4,5-dihydro-1H-pyrazole-1-carboxamide N-(4-nitrophenyl)-3-(4-chlorophenyl)-4-carboethoxy-4-methyl-4,5-dihydro-1H-pyrazole-1-carboxamide N-(4-nitrophenyl)-3-(4-chlorophenyl)-4-carbomethoxy-4,5-dihydro-1H-pyrazole-1-carboxamide N-(4-trifluoromethoxyphenyl)-3-(3-chloro-4-trifluoromethylphenyl)-4-carboethoxy-4-methyl-4,5-dihydro-1H-pyrazole-1-carboxamide N-(4-trifluoromethoxyphenyl)-3-(4-chlorophenyl)-4-carboethoxy-4-methyl-4,5-dihydro-1H-pyrazole-1-carboxamide N-(4-trimethylammoniumphenyl)-3-(4-chlorophenyl)-4-carbomethoxy-4-methyl-4,5-dihydro-1H-pyrazole-1-carboxamide iodide N-(4-trifluoromethylphenyl)-3-(4-chlorophenyl)-4-dimethylcarbamoyl-4-methyl-4,5-dihydro-1H-pyrazole-1-carboxamide N-(4-trifluoromethoxyphenyl)-3-(4-chlorophenyl)-4-carbomethoxy-4-methyl-4,5-dihydro-1H-pyrazole-1-carboxamide N-(4-trifluoromethylphenyl)-3-(3-chloro-4-trifluoromethylphenyl)-4-(3-methylthiopropyl)-4-acetyl-4,5-dihydro-1H-pyrazole-1-carboxamide N-(4-trifluoromethylphenyl)-3-(3-chloro-4-trifluoromethylphenyl)-4-(3-methylthiopropyl)-4-carbomethoxy-4,5-dihydro-1H-pyrazole-1-carboxamide N-(4-trifluoromethylphenyl)-3-(3-chloro-4-trifluoromethylphenyl)-4-carboethoxy-4-(2-chloroallyl)-4,5-dihydro-1H-pyrazole-1-carboxamide N-(4-trifluoromethylphenyl)-3-(3-chloro-4-trifluoromethylphenyl)-4-carboethoxy-4-(2-methylthioethyl)-4,5-dihydro-1H-pyrazole-1-carboxamide N-(4-trifluoromethylphenyl)-3-(3-chloro-4-trifluoromethylphenyl)-4-carboethoxy-4-(3-cyanopropyl)-4,5-dihydro-1H-pyrazole-1-carboxamide N-(4-trifluoromethylphenyl)-3-(3-chloro-4-trifluoromethylphenyl)-4-carboethoxy-4-(4-chlorophenyl)-4,5-dihydro-1H-pyrazole-1-carboxamide N-(4-trifluoromethylphenyl)-3-(3-chloro-4-trifluoromethylphenyl)-4-carboethoxy-4-(4-difluoromethoxyphenyl)-4,5-dihydro-1H-pyrazole-1-carboxamide N-(4-trifluoromethylphenyl)-3-(3-chloro-4-trifluoromethylphenyl)-4-carboethoxy-4-(4-trifluoromethoxyphenyl)-4,5-dihydro-1H-pyrazole-1-carboxamide N-(4-trifluoromethylphenyl)-3-(3-chloro-4-trifluoromethylphenyl)-4-carboethoxy-4-(4-trifluoromethylphenyl)-4,5-dihydro-1H-pyrazole-1-carboxamide N-(4-trifluoromethylphenyl)-3-(3-chloro-4-trifluoromethylphenyl)-4-carboethoxy-4-acetyl-4,5-dihydro-1H-pyrazole-1-carboxamide N-(4-trifluoromethylphenyl)-3-(3-chloro-4-trifluoromethylphenyl)-4-carboethoxy-4-allyl-4,5-dihydro-1H-pyrazole-1-carboxamide N-(4-trifluoromethylphenyl)-3-(3-chloro-4-trifluoromethylphenyl)-4-carboethoxy-4-benzyl-4,5-dihydro-1H-pyrazole-1-carboxamide N-(4-trifluoromethylphenyl)-3-(3-chloro-4-trifluoromethylphenyl)-4-carboethoxy-4-carbomethoxy-4,5-dihydro-1H-pyrazole-1-carboxamide N-(4-trifluoromethylphenyl)-3-(3-chloro-4-trifluoromethylphenyl)-4-carboethoxy-4-ethyl-4,5-dihydro-1H-pyrazole-1-carboxamide N-(4-trifluoromethylphenyl)-3-(3-chloro-4-trifluoromethylphenyl)-4-carboethoxy-4-methallyl-4,5-dihydro-1H-pyrazole-1-carboxamide N-(4-trifluoromethylphenyl)-3-(3-chloro-4-trifluoromethylphenyl)-4-carboethoxy-4-methoxymethyl-4,5-dihydro-1H-pyrazole-1-carboxamide N-(4-trifluoromethylphenyl)-3-(3-chloro-4-trifluoromethylphenyl)-4-carboethoxy-4-methyl-4,5-dihydro-1H-pyrazole-1-carboxamide N-(4-trifluoromethylphenyl)-3-(3-chloro-4-trifluoromethylphenyl)-4-carboethoxy-4-methyl-N-(2-methoxyethylsulfenyl)-4,5-dihydro-1H-pyrazole-1-carboxamide N-(4-trifluoromethylphenyl)-3-(3-chloro-4-trifluoromethylphenyl)-4-carboethoxy-4-methyl-N-(2-nitrophenylsulfenyl)-4,5-dihydro-1H-pyrazole-1-carboxamide (N-(4-trifluoromethylphenyl)-3-(3-chloro-4-trifluoromethylphenyl)-4-carboethoxy-4-methyl-N-acetyl-4,5-dihydro-1H-pyrazole-1-carboxamide N-(4-trifluoromethylphenyl)-3-(3-chloro-4-trifluoromethylphenyl)-4-carboethoxy-4-methyl-N-carboethoxy-4,5-dihydro-1H-pyrazole-1-carboxamide N-(4-trifluoromethylphenyl)-3-(3-chloro-4-trifluoromethylphenyl)-4-carboethoxy-4-methyl-N-carbomethoxy-4,5-dihydro-1H-pyrazole-1-carboxamide N-(4-trifluoromethylphenyl)-3-(3-chloro-4-trifluoromethylphenyl)-4-carboethoxy-4-methyl-N-carbomethoxycarbonyl-4,5-dihydro-1H-pyrazole-1-carboxamide N-(4-trifluoromethylphenyl)-3-(3-chloro-4-trifluoromethylphenyl)-4-carboethoxy-4-methyl-N-carbomethoxysulfenyl-4,5-dihydro-1H-pyrazole-1-carboxamide N-(4-trifluoromethylphenyl)-3-(3-chloro-4-trifluoromethylphenyl)-4-carboethoxy-4-methyl-N-dimethylcarbamoyl-4,5-dihydro-1H-pyrazole-1-carboxamide N-(4-trifluoromethylphenyl)-3-(3-chloro-4-trifluoromethylphenyl)-4-carboethoxy-4-methyl-N-formyl-4,5-dihydro-1H-pyrazole-1-carboxamide N-(4-trifluoromethylphenyl)-3-(3-chloro-4-trifluoromethylphenyl)-4-carboethoxy-4-methyl-N-methoxymethyl-4,5-dihydro-1H-pyrazole-1-carboxamide N-(4-trifluoromethylphenyl)-3-(3-chloro-4-trifluoromethylphenyl)-4-carboethoxy-4-methyl-N-methyl-4,5-dihydro-1H-pyrazole-1-carboxamide N-(4-trifluoromethylphenyl)-3-(3-chloro-4-trifluoromethylphenyl)-4-carboethoxy-4-methyl-N-methylsulfenyl-4,5-dihydro-1H-pyrazole-1-carboxamide N-(4-trifluoromethylphenyl)-3-(3-chloro-4-trifluoromethylphenyl)-4-carboethoxy-4-methyl-N-trifluoroacetyl-4,5-dihydro-1H-pyrazole-1-carboxamide N-(4-trifluoromethylphenyl)-3-(3-chloro-4-trifluoromethylphenyl)-4-carboethoxy-4-methylthiomethyl-4,5-dihydro-1H-pyrazole-1-carboxamide N-(4-trifluoromethylphenyl)-3-(3-chloro-4-trifluoromethylphenyl)-4-carboethoxy-4-phenyl-4,5-dihydro-1H-pyrazole-1-carboxamide N-(4-trifluoromethylphenyl)-3-(3-chloro-4-trifluoromethylphenyl)-4-methyl-4-acetyl-4,5-dihydro-1H-pyrazole-1-carboxamide N-(4-trifluoromethylphenyl)-3-(3-chloro-4-trifluoromethylphenyl)-4-methyl-4-carbomethoxy-4,5-dihydro-1H-pyrazole-1-carboxamide N-(4-trifluoromethylphenyl)-3-(3-chloro-4-trifluoromethylphenyl)-4-phenyl-4-acetyl-4,5-dihydro-1H-pyrazole-1-carboxamide N-(4-trifluoromethylphenyl)-3-(3-chloro-4-trifluoromethylphenyl)-4-phenyl-4-carbomethoxy-4,5-dihydro-1H-pyrazole-1-carboxamide N-(4-trifluoromethylphenyl)-3-(4-chlorophenyl)-4-(3-methylthiopropyl)-4-acetyl-4,5-dihydro-1H-pyrazole-1-carboxamide N-(4-trifluoromethylphenyl)-3-(4-chlorophenyl)-4-(3-methylthiopropyl)-4-carbomethoxy-4,5-dihydro-1H-pyrazole-1-carboxamide N-(4-trifluoromethylphenyl)-3-(4-chlorophenyl)-4-carboethoxy-4-(2-chloroallyl)-4,5-dihydro-1H-pyrazole-1-carboxamide N-(4-trifluoromethylphenyl)-3-(4-chlorophenyl)-4-carboethoxy-4-(2-methylthioethyl)-4,5-dihydro-1H-pyrazole-1-carboxamide N-(4-trifluoromethylphenyl)-3-(4-chlorophenyl)-4-carboethoxy-4-(3-cyanopropyl)-4,5-dihydro-1H-pyrazole-1-carboxamide N-(4-trifluoromethylphenyl)-3-(4-chlorophenyl)-4-carboethoxy-4-(4-chlorophenyl)-4,5-dihydro-1H-pyrazole-1-carboxamide N-(4-trifluoromethylphenyl)-3-(4-chlorophenyl)-4-carboethoxy-4-(4-difluoromethoxyphenyl)-4,5-dihydro-1H-pyrazole-1-carboxamide N-(4-trifluoromethylphenyl)-3-(4-chlorophenyl)-4-carboethoxy-4-(4-trifluoromethoxyphenyl)-4,5-dihydro-1H-pyrazole-1-carboxamide N-(4-trifluoromethylphenyl)-3-(4-chlorophenyl)-4-carboethoxy-4-(4-trifluoromethylphenyl)-4,5-dihydro-1H-pyrazole-1-carboxamide N-(4-trifluoromethylphenyl)-3-(4-chlorophenyl)-4-carboethoxy-4-acetyl-4,5-dihydro-1H-pyrazole-1-carboxamide N-(4-trifluoromethylphenyl)-3-(4-chlorophenyl)-4-carboethoxy-4-allyl-4,5-dihydro-1H-pyrazole-1-carboxamide N-(4-trifluoromethylphenyl)-3-(4-chlorophenyl)-4-carboethoxy-4-benzyl-4,5-dihydro-1H-pyrazole-1-carboxamide N-(4-trifluoromethylphenyl)-3-(4-chlorophenyl)-4-carboethoxy-4-carbomethoxy-4,5-dihydro-1H-pyrazole-1-carboxamide N-(4-trifluoromethylphenyl)-3-(4-chlorophenyl)-4-carboethoxy-4-ethyl-4,5-dihydro-1H-pyrazole-1-carboxamide N-(4-trifluoromethylphenyl)-3-(4-chlorophenyl)-4-carboethoxy-4-methallyl-4,5-dihydro-1H-pyrazole-1-carboxamide N-(4-trifluoromethylpheny)-3-(B 4-chlorophenyl)-4-carboethoxy-4-methoxymethyl-4,5-dihydro-1H-pyrazole-1-carboxamide N-(4-trifluoromethylphenyl)-3-(4-chlorophenyl)-4-carboethoxy-4-methyl-B 4,5-dihydro-1H-pyrazole-1-carboxamide N-(4-trifluoromethylpheny)-3-(4-chlorophenyl)-4-carboethoxy-4-methyl-N-(2-methoxyethylsulfenyl)-4,5-dihydro-1H-pyrazole-1-carboxamide N-(4-trifluoromethylphenyl)-3-(4-chlorophenyl)-4-carboethoxy-4-methyl-N-(2-nitrophenylsulfenyl)-4,5-dihydro-1H-pyrazole-1-carboxamide N-(4-trifluoromethylphenyl)-3-(4-chlorophenyl)-4-carboethoxy-4-methyl-N-acetyl-4,5-dihydro-1H-pyrazole-1-carboxamide N-(4-trifluoromethylphenyl)-3-(4-chlorophenyl)-4-carboethoxy-4-methyl-N-carboethoxy-4,5-dihydro-1H-pyrazole-1-carboxamide N-(4-trifluoromethylphenyl)-3-(4-chlorophenyl)-4-carboethoxy-4-methyl-4-carbomethoxy-4,5-dihydro-1H-pyrazole-1-carboxamide N-(4-trifluoromethylphenyl)-3-(4-chlorophenyl)-4-carboethoxy-4-methyl-N-carbomethoxycarbonyl-4,5-dihydro-1H-pyrazole-1-carboxamide N-(4-trifluoromethylphenyl)-3-(4-chlorophenyl)-4-carboethoxy-4-methyl-N-carbomethoxysulfenyl-4,5-dihydro-1H-pyrazole-1-carboxamide N-(4-trifluoromethylphenyl)-3-(4-chlorophenyl)-4-carboethoxy-4-methyl-N-dimethylcarbamoyl-4,5-dihydro-1H-pyrazole-1-carboxamide N-(4-trifuoromethylphenyl)-3-(4-chlorophenyl)-4-carboethoxy-4-methyl-N-formyl-4,5-dihydro-1H-pyrazole-1-carboxamide N-(4-trifluoromethylphenyl)-3-(4-chlorophenyl)-4-carboethoxy-4-methyl-N-methoxymethyl-4,5-dihydro-1H-pyrazole-1-carboxamide N-(4-trifluoromethylphenyl)-3-(4-chlorophenyl)-4-carboethoxy-4-methyl-N-methyl-4,5-dihydro-1H-pyrazole-1-carboxamide N-(4-trifluoromethylphenyl)-3-(4-chlorophenyl)-4-carboethoxy-4-methyl-N-methylsulfenyl-4,5-dihydro-1H-pyrazole-1-carboxamide N-(4-trifluoromethylphenyl)-3-(4-chlorophenyl)-4-carboethoxy-4-methyl-N-trifluoroacetyl-4,5-dihydro-1H-pyrazole-1-carboxamide N-(4-trifluoromethylphenyl)-3-(4-chlorophenyl)-4-carboethoxy-4-methylthiomethyl-4,5-dihydro-1H-pyrazole-1-carboxamide N-(4-trifluoromethylphenyl)-3-(4-chlorophenyl)-4-carboethoxy-4-phenyl-4,5-dihydro-1H-pyrazole-1-carboxamide N-(4-trifluoromethylphenyl)-3-(4-chlorophenyl)-4-carbomethoxy-4-methyl-4,5-dihydro-1H-pyrazole-1-carboxamide N-(4-trifluoromethylphenyl)-3-(4-chlorophenyl)-4-methyl-4-acetyl-4,5-dihydro-1H-pyrazole-1-carboxamide N-(4-trifluoromethylphenyl)-3-(4-chlorophenyl)-4-methyl-4-carbomethoxy-4,5-dihydro-1H-pyrazole-1-carboxamide N-(4-trifluoromethylphenyl)-3-(4-chlorophenyl)-4-phenyl-4-acetyl-4,5-dihydro-1H-pyrazole-1-carboxamide N-(4-trifluoromethylphenyl)-3-(4-chlorophenyl)-4-phenyl-4-carbomethoxy-4,5-dihydro-1H-pyrazole-1-carboxamide N-(4-trifluoromethylphenyl)-3-phenyl-4-carboethoxy-4,5-dihydro-1H-pyrazole-1-carboxamide N-(4-trifluoromethylphenyl)-3-phenyl-4-carbomethoxy-4-methyl-4,5-dihydro-1H-pyrazole-1carboxamide N-(4-trifluoromethylphenyl)-3-phenyl-4-dimethylcarbamoyl-4,5-dihydro-1H-pyrazole-1-carboxamide N-phenyl-3-(3-chloro-4-trifluoromethylphenyl)-4-carboethoxy-4-methyl-4,5-dihydro-1H-pyrazole-1-carboxamide N-phenyl-3-(4-chlorophenyl)-4-carboethoxy-4-methyl-4,5-dihydro-1H-pyrazole-1-carboxamide N-phenyl-3-(4-chlorophenyl)-4-carbomethoxy-4-methyl-4,5-dihydro-1H-pyrazole-1-carboxamide The present invention includes unique processes for preparing 1-substituted-4-substituted-4,5-dihydro-1H-pyrazoles. One of these processes comprises dissolving a 1-substituted-4,5-dihydro-1H-pyrazole in an aprotic solvent, mixing a strong base with the resultant solution, allowing deprotonation to take place at the 4 position of the pyrazole ring, and then adding an alkylating or acylating agent, wherein the 1-substituted-4,5-dihydro-1H-pyrazole dissolved in the aprotic solvent must be a 1-substituted-4-monosubstituted-4,5-dihydro-1H-pyrazole when the desired end product is a 1-substituted-4,4-disubstituted-4,5-dihydro-1-pyrazole. Processes for making 1-substituted-4-monosubstituted-4,5-dihydro-1-H-pyrazole and 1-substituted-4-unsubstituted-4,5-dihydro-1H-pyrazole are known to those skilled in the art (See, e.g., U.S. Pat. No. 4,156,007) and are described in Examples A through J.

In carrying out the process, the 1-substituted-4,5-dihydro-1H-pyrazole which is dissolved in the aprotic solvent may be added to the base or the base may be added to the 1-substituted-4,5-dihydro-1H-pyrazole which has been dissolved in the aprotic solvent. Any 1-substituted-4,5-dihydro-1H-pyrazole may be dissolved in the aprotic solvent. Examples of 1-substituted-4,5-dihydro-1H-pyrazoles which may be employed in the process of this invention include, but are not limited to:

N,3,4-tris-(4-chlorophenyl)-4,5-dihydro-1H-pyrazole-1-carboxamide
N,3-bis-(3,4-dichlorophenyl)-4-phenyl-4,5-dihydro-1H-pyrazole-1-carboxamide
N,3-bis-(4-chlorophenyl)-4-methyl-4,5-dihydro-1H-pyrazole-1-carboxamide
N,3-bis-(4-chlorophenyl)-4-phenyl-4,5-dihydro-1H-pyrazole-1-carboxamide
N,3-bis-(4-chlorophenyl)-4-(2-methylethyl)-4,5-dihydro-1H-pyrazole-1-carboxamide
N,3-bis-(4-chlorophenyl)-4-(2-methylpropyl)-4,5-dihydro-1H-pyrazole-1-carboxamide
N,3-bis-(4-chlorophenyl)-4-(4-chlorobutyl)-4,5-dihydro-1H-pyrazole-1-carboxamide
N,3-bis-(4-chlorophenyl)-4-cyclohexyl-4,5-dihydro-1H-pyrazole-1-carboxamide
N,3-bis-(4-chlorophenyl)-4-ethyl-4,5-dihydro-1H-pyrazole-1-carboxamide
N,3-bis-(4-chloropheny)-4-phenyl-4,5-dihydro-1H-pyrazole-1-thiocarboxamide
N,(3-chlorophenyl)-3-(4-chlorophenyl)-4-phenyl-4,5-dihydro-1H-pyrazole-1-carboxamide
N-(4-bromophenyl)-3-(4-fluorophenyl)-4-methyl-4,5-dihydro-1H-pyrazole-1-carboxamide
N-(4-carboethoxypheny)-3-(4-chlorophenyl)-4-phenyl-4,5-dihydro-1H-pyrazole-1-carboxamide
N-(4-carboisopropoxyphenyl)-3-(4-chlorophenyl)-4-phenyl-4,5-dihydro-1H-pyrazole-1-carboxamide
N-(2,4-dichlorophenyl)-3-(4-chlorophenyl)-4-phenyl-4,5-dihydro-1H-pyrazole-1-carboxamide
N-(2-pyridyl)-3-(4-chlorophenyl)-4-phenyl-4,5-dihydro-1H-pyrazole-1-carboxamide
N-(3,4-dichlorophenyl)-3,4-bis-(4-chlorophenyl)-4,5-dihydro-1H-pyrazole-1-carboxamide
N-(3,4-dichlorophenyl)-3-(4-difluoromethoxyphenyl)-4-phenyl-4,5-dihydro-1H-pyrazole-1-carboxamide
N-(3,5-dichlorophenyl)-3-(4-chlorophenyl)-4-phenyl-4,5-dihydro-1H-pyrazole-1-carboxamide
N-(3-chlorophenyl)-3-(4-chlorophenyl)-4-phenyl-4,5-dihydro-1H-pyrazole-1-carboxamide
N-(3-cyanophenyl)-3-(4-chlorophenyl)-4-phenyl-4,5-dihydro-1H-pyrazole-1-carboxamide
N-(3-phenoxyphenyl)-3-(4-chlorophenyl)-4-phenyl-4,5-dihydro-1H-pyrazole-1-carboxamide
N-(3-pyridyl)-3-(4-chlorophenyl)-4-phenyl-4,5-dihydro-1H-pyrazole-1-carboxamide
N-(3-trifluoromethylphenyl)-3-(4-chlorophenyl)-4-phenyl-4,5-dihydro-1H-pyrazole-1-carboxamide
N-(4-trifluoromethylphenyl)-3-(4-chlorophenyl)-4-phenyl-4,5-dihydro-1H-pyrazole-1-carboxamide
N,3-bis-(4-trifluoromethylphenyl)-4-phenyl-4,5-dihydro-1H-pyrazole-1-carboxamide
N-(4-trifluoromethylphenyl)-3-(4-chlorophenyl)-4-methyl-4,5-dihydro-1H-pyrazole-1-carboxamide
N,3-bis-(4-trifluoromethylphenyl)-4-methyl-4,5-dihydro-1H-pyrazole-1-carboxamide
N-(4-bromophenyl)-3-(4-chlorophenyl)-4-methyl-4,5-dihydro-1H-pyrazole-1-carboxamide
N-(4-bromophenyl)-3-(4-chlorophenyl)-4-phenyl-4,5-dihydro-1H-pyrazole-1-carboxamide
N-(4-carboethoxyphenyl)-3,4-diphenyl-4,5-dihydro-1H-pyrazole-1-carboxamide
N-(4-carboethoxyphenyl)-3-(4-chlorophenyl)-4-phenyl-4,5-dihydro-1H-pyrazole-1-carboxamide
N-(4-carboisopropoxyphenyl)-3,4-diphenyl-4,5-dihydro-1H-pyrazole-1-carboxamide
N-(4-carboisopropoxyphenyl)-3-(4-chlorophenyl)-4-phenyl-4,5-dihydro-1H-pyrazole-1-carboxamide
N-(4-carbomethoxyphenyl)-3-(4-chlorophenyl)-4-phenyl-4,5-dihydro-1H-pyrazole-1-carboxamide
N-(4-chlorophenyl)-3,4-diphenyl-4,5-dihydro-1H-pyrazole-1-carboxamide
N-(4-chlorophenyl)-3-(3,4-dichlorophenyl)-4-phenyl-4,5-dihydro-1H-pyrazole-1-carboxamide
N-(4-chlorophenyl)-3-(4-bromophenyl)-4-methyl-4,5-dihydro-1H-pyrazole-1-carboxamide
N-(4-chlorophenyl)-3-(4-difluoromethoxyphenyl)-4-phenyl-4,5-dihydro-1H-pyrazole-1-carboxamide
N-(4-chlorophenyl)-3-(4-fluorophenyl)-4-methyl-4,5-dihydro-1H-pyrazole-1-carboxamide
N-(4-chlorophenyl)-3-phenyl-4-methyl-4,5-dihydro-1H-pyrazole-1-carboxamide
N-(4-difluoromethoxyphenyl)-3-(4-chlorophenyl)-4-phenyl-4,5-dihydro-1H-pyrazole-1-carboxamide
N-(4-fluorophenyl)-3-(4-chlorophenyl)-4-phenyl-4,5-dihydro-1H-pyrazole-1-carboxamide
N-(4-nitrophenyl)-3-(4-chlorophenyl)-4-phenyl-4,5-dihydro-1H-pyrazole-1-carboxamide
N-(4-phenoxyphenyl)-3-(4-chlorophenyl)-4-phenyl-4,5-dihydro-1H-pyrazole-1-carboxamide
N-(4-phenyl)-3-(4-chlorophenyl)-4-phenyl-4,5-dihydro-1H-pyrazole-1-carboxamide
N-(4-pyridyl)-3-(4-chlorophenyl)-4-phenyl-4,5-dihydro-1H-pyrazole-1-carboxamide Preferably, the base used is a strong base; that is, a base having sufficient strength to deprotonate the 4,5-dihydro-1H-pyrazole at the 4-position of the pyrazole ring. Therefore, a base, the conjugate acid of which has a pKa of at least about 10, is required.

Suitable bases for use in this process include, but are not limited to, alkali metal hydroxides, alkaline earth hydroxides, alkali metal alkoxides, alkaline earth alkoxides, alkali metal hydrides, alkaline earth hydrides, alkali metal oxides, alkaline earth oxides, alkali metal amides, alkaline earth amides, alkyl lithiums, aryl lithiums or such other strong bases as are known to those skilled in the art. The preferred bases are alkali metal amides. The most preferred base is lithium diisopropylamide.

The reaction must be carried out in the presence of an aprotic solvent. Suitable aprotic solvents are those not significantly deprotonated under reaction conditions.

Aprotic solvents that are useful in carrying out the invention include, but are not limited to, dialkyl ethers, tetrahydrofuran, aliphatic hydrocarbons, aromatic hydrocarbons, aliphatic alcohols, amines, ammonia, dialkyl amides, dialkyl sulfoxides, dialkyl sulfones, polyalkyl phosphoric amides, and such other solvents that are known by those skilled in the art. Preferred solvents are dialkyl·ethers, ammonia, tetrahydrofuran, and amines. The most preferred solvent is tetrahydrofuran.

Alkylating and/or acylating agents that are useful in carrying out the process of this invention vary with the particular compound being synthesized. For example, to effect a methylation, appropriate alkylating agents would include, but are not limited to, methyl chloride, methyl bromide, methyl iodide, methyl arylsulfonates, methyl alkylsulfonates, methyl sulfate, trimethyl oxonium salts, methyl halosulfonates, and such other methylating agents as are known to those skilled in the art. Preferred methylating agents are methyl chloride, methyl bromide, methyl iodide, and methyl sulfate. The most preferred methylating agent is methyl iodide. Examples of acylating agents include but are not limited to: alkanoyl chlorides, aroyl chlorides, alkyl chloroformates, aryl chloroformates, alkyl carbonates, aryl carbonates, alkyl isocyanates, aryl isocyanates, alkyl isothiocyanates, aryl isothiocyanates, dialkyl carbamoyl chlorides, alkyl chlorothioformates, aryl chlorothioformates, dialkyl carbodiimides, alkyl aryl carbodiimides, diaryl carbodiimides, carbon dioxide, and carbon disulfide. Those skilled in the art will be able to choose other appropriate alkylating and/or acylating agents to introduce other Y groups.

The reaction temperature can be varied within a substantial range. In general, the reaction is carried out at from about $-120°$ C. to about $200°$ C., preferable at from about $-78°$ C. to about $100°$ C. The reaction is allowed to take place under normal pressure. The most preferred temperature is $-10°$ C. Yields may be improved by carrying out the reaction at temperatures from $-80°$ C. to $-30°$ C. when using acylating agents.

To carry out the process, the materials are preferably employed in stoichiometric amounts. An excess of one or the other component produces no significant advantages. After completion of the reaction, acetic acid is added to neutralize the reaction.

A second process for preparing compounds of the present invention where Y is a group having the formula $$\begin{matrix} & X \\ & \| \\ & -C-G \end{matrix}$$

(Group B) comprises treating a beta-dicarbonyl compound of the Formula II $$\underset{A-C-CH_2-C-G}{\overset{O \quad\quad X}{\|\quad\quad\|}} \quad\quad II$$

where A, X and G are as defined above for Formula I with a mixture of hydrazine and formaldehyde to produce a 3-aryl-4-monosubstituted-4,5-dihydropyrazole having the formula $$\begin{matrix} A & & X \\ \diagdown & & \| \\ C & \text{---} & C-G \\ \| & & | \\ N & CH \\ \diagdown & & | \\ & N & CH_2 \\ & | \\ & H \end{matrix} \quad III$$

Where A, X, and G are as defined above for Formula I. Treatment of the dihydropyrazole of Formula III with an aryl isocyanate gives the N-aryl-3-aryl-4-monosubstituted-4,5-dihydropyrazole-1-carboxamides of this invention.

Further treatment of this 1-substituted-4-mono-substituted-4,5-dihydropyrazole-1-carboxamide with a base, followed by an alkylating agent or acylating agent will yield the N-aryl-3-aryl-4,4-disubstituted-4,5-dihydropyrazole-1-carboxamides of this invention.

In carrying out the process, to produce a 3-aryl-4-monosubstituted-4,5-dihydropyrazole having the Formula III, any beta-dicarbonyl compound of Formula II may be used. Examples of beta-dicarbonyl compounds which may be employed in this process of the invention include, but are not limited to:

2-endo-norbornyl 3-(3-chloro-4-difluoromethylphenyl)-3-oxo-propanoate;
2-endo-norbornyl-3-(4-chlorophenyl)-3-oxo-propanoate;
2-methylthioethyl-3-(3-methyl-4-trifluoromethylphenyl)-3-oxo-propanoate;
2-methylthioethyl 3-(4-chlorophenyl)-3-oxo-propanoate;
3'-trifluoromethylbenzyl 3-(3-chloro-4-difluoromethoxyphenyl)-3-oxo-propanoate;
3'-trifluoromethylbenzyl 3-(4-chloropheny)-3-oxo-propanoate;
3-(3-methyl-4-trifluoromethylphenyl)-3-oxo-propanamide;
N,N-diethyl 3-(3-fluoro-4-trifluoromethylphenyl)-3-oxo-propanamide;
N,N-dimethyl 3-(3-chloro-4-trifluoromethylphenyl)-3-oxo-propanamide;
N-cyclopentyl-3-(4-chloro-3-trifluoromethylphenyl)-3-oxo-propanamide;
N-ethyl-N-methyl 3-(3-chloro-4-difluoromethylphenyl)-3-oxo-propanamide;
N-methyl-N-phenyl 3-(3-chloro-4-trifluoromethoxyphenyl)-3-oxo-propanamide;
N-phenyl 3-(2-chloro-4-trifluoromethylphenyl)-3-oxo-propanamide;
N-propyl 3-(3-bromo-4-trifluoromethylphenyl)-3-oxo-propanamide;
allyl 3-(3-chloro-4-trifluoromethylphenyl)-3-oxo-propanoate;
allyl 3-(4-chlorophenyl)-3-oxo-propanoate;
cyclopentyl 3-(4-chloro-3-trifluoromethylphenyl)-3-oxo-propanoate;
cyclopentyl 3-(4-chlorophenyl)-3-oxo-propanoate;
ethyl 3-(3-fluoro-4-trifluoromethylphenyl)-3-oxo-dithiopropanoate;
ethyl 3-(3-fluoro-4-trifluoromethylphenyl)-3-oxo-propanoate;
ethyl 3-(4-chlorophenyl)-3-oxo-propanoate;
methyl 3-(3-chloro-4-trifluoromethylphenyl)-3-oxo-dithiopropanoate;

methyl 3-(3-chloro-4-trifluoromethylphenyl)-3-oxo-propanoate;
methyl 3-(4-chlorophenyl)-3-oxo-propanoate;
phenyl 3-(2-chloro-4-trifluoromethylphenyl)-3-oxo-dithiopropanoate;
phenyl 3-(2-chloro-4-trifluoromethylphenyl)-3-oxo-propanoate;
phenyl 3-(4-chlorophenyl)-3-oxo-propanoate;
propyl 3-(3-bromo-4-trifluoromethylphenyl)-3-oxo-dithiopropanoate;
propyl 3-(3-bromo-4-trifluoromethylphenyl)-3-oxo-propanoate;
propyl 3-(4-chlorophenyl)-3-oxo-propanoate;
t-butyl 3-(3-chloro-4-trifluoromethoxyphenyl)-3-oxo-propanoate; or
t-butyl 3-(4-chlorophenyl)-3-oxo-propanoate.

Preferably, a substantially equimolar mixture of hydrazine and formaldehyde is used.

The reaction may be carried out in the presence or absence of a solvent. Suitable solvents are those that afford some solubility to the components of the reaction mixture. Suitable solvents that are useful in carrying out the invention include, but are not limited to, water, dialkyl ethers, tetrahydrofuran, aliphatic hydrocarbons, aromatic hydrocarbons, aliphatic alcohols, tertiary amines, dialkyl amides, dialkyl sulfoxides, dialkyl sulfones, polyalkyl phosphoric amides, and such other solvents that are known by those skilled in the art. Preferred solvents are aliphatic alcohols, tetrahydrofuran, and tertiary amines. The most preferred solvent is methanol.

Because of the basic nature of hydrazine, the reaction can be carried out in the presence or absence of additional base. Suitable additional bases for use in this process include, but are not limited to, alkali metal hydroxide, alkaline earth hydroxide, alkali metal alkoxide, alkaline earth alkoxide, alkali metal oxide, alkaline earth oxide, tertiary amines, amidines, guanidines, and such other bases that are known to those skilled in the art.

The reaction temperature can be varied within a substantial range. In general, the reaction is carried out at from about −120° C. to about 200° C., preferably at from about −78° C. to about 100° C. The reaction is allowed to take place under normal pressure. The most preferred temperature is about 20° C.

Treatment of the dihydropyrazole of Formula III with an aryl isocyanate gives the N-aryl-3-aryl-4-monosubstituted-4,5-dihydropyrazole-1-carboxamides of this invention.

In carrying out the process, to produce a 3-aryl-4-monosubstituted-4,5-dihydropyrazole-1-carboxamide of this invention, any aryl isocyanate of the formula

B—N=C=O    IV where B is as defined in Formula I may be used. Examples of aryl isocyanates which may be employed in this process of this invention include, but are not limited to:
3,4-dichlorophenyl isocyanate;
3-bromo-4-dimethylaminophenyl isocyanate;
3-bromo-4-methylphenyl isocyanate;
3-bromo-4-methylphenyl isothiocyanate;
3-bromo-4-trifluoromethylphenyl isocyanate;
3-bromodifluoromethoxyphenyl isocyanate;
3-bromodifluorothiomethoxyphenyl isocyanate;
3-bromophenyl isocyanate;
3-carboethoxyphenyl isocyanate;
3-carboisopropoxyphenyl isocyanate;
3-carbomethoxyphenyl isocyanate;
3-chloro-4-bromodifluoromethoxyphenyl isocyanate;
3-chloro-4-bromodifluorothiomethoxyphenyl isocyanate;
3-chloro-4-bromophenyl isocyanate;
3-chloro-4-carboethoxyphenyl isocyanate;
3-chloro-4-carboisopropoxyphenyl isocyanate;
3-chloro-4-carbomethoxyphenyl isocyanate;
3-chloro-4-cyanophenyl isocyanate;
3-chloro-4-difluoromethoxyphenyl isocyanate;
3-chloro-4-dimethylaminophenyl isocyanate;
3-chloro-4-fluorophenyl isocyanate;
3-chloro-4-iodophenyl isocyanate;
3-chloro-4-methylphenyl isocyanate;
3-chloro-4-methylsulfinylphenyl isocyanate;
3-chloro-4-methylsulfonylphenyl isocyanate;
3-chloro-4-methylthiophenyl isocyanate;
3-chloro-4-nitrophenyl isocyanate;
3-chloro-4-trifluoromethoxyphenyl isocyanate;
3-chloro-4-trifluoromethylphenyl isocyanate;
3-chlorophenyl isocyanate;
3-cyano-4-carbomethoxyphenyl isocyanate;
3-cyano-4-carbomethoxyphenyl isothiocyanate;
3-cyanophenyl isocyanate;
3-difluoromethoxy-4-methylthiophenyl isocyanate;
3-difluoromethoxyphenyl isocyanate;
3-dimethylaminophenyl isocyanate;
3-fluoro-4-bromophenyl isocyanate;
3-fluoro-4-carboethoxyphenyl isocyanate;
3-fluoro-4-carboethoxyphenyl isothiocyanate;
3-fluoro-4-cyanophenyl isocyanate;
3-fluoro-4-cyanophenyl isothiocyanate;
3-fluorophenyl isocyanate;
3-iodo-4-difluoromethoxyphenyl isocyanate;
3-iodo-4-fluorophenyl isocyanate;
3-iodophenyl isocyanate;
3-methyl-4-trifluoromethoxyphenyl isocyanate;
3-methylphenyl isocyanate;
3-methylsulfinylphenyl isocyanate;
3-methylsulfonylphenyl isocyanate;
3-methylthio-4-methylsulfinylphenyl isocyanate;
3-methylthiophenyl isocyanate;
3-methylthio-4-bromodifluoromethoxyphenyl isocyanate;
3-nitro-4-bromodifluorothiomethoxyphenyl isocyanate;
3-nitro-4-bromodifluorothiomethoxyphenyl isothiocyanate;
3-nitrophenyl isocyanate;
3-trifluoromethoxy-4-methylsulfonylphenyl isocyanate;
3-trifluoromethoxy-4-nitrophenyl isocyanate;
3-trifluoromethoxy-4-nitrophenyl isothiocyanate;
3-trifluoromethoxyphenyl isocyanate;
3-trifluoromethyl-4-carboisopropoxyphenyl isocyanate;
3-trifluoromethyl-4-carboisothiopropoxyphenyl isothiocyanate;
3-trifluoromethyl-4-iodophenyl isocyanatel;
3-trifluoromethylphenyl isocyanate;
4-bromodifluoromethoxyphenyl isocyanate;
4-bromodifluorothiomethoxyphenyl isocyanate;
4-bromophenyl isocyanate;
4-bromophenyl isothiocyanate;
4-carboethoxyphenyl isocyanate;
4-carboisopropoxyphenyl isocyanate;
4-carbomethoxyphenyl isocyanate;
4-chlorophenyl isocyanate;
4-chlorophenyl isothiocyanate;
4-cyanophenyl isocyanate;
4-difluoromethoxyphenyl isocyanate;

4-difluoromethoxyphenyl isothiocyanate;
4-dimethylaminophenyl isocyanate;
4-fluorophenyl isocyanate;
4-iodophenyl isocyanate;
4-methylphenyl isocyanate;
4-methylsulfinylphenyl isocyanate;
4-methylsulfonylphenyl isocyanate;
4-methylthiophenyl isocyanate;
4-nitrophenyl isocyanate;
4-pentafluorosulfuranylphenyl isocyanate;
4-trifluoromethoxyphenyl isocyanate;
4-trifluoromethoxyphenyl isothiocyanate;
4-trifluoromethylphenyl isocyanate;
4-trifluoromethylphenyl isothiocyanate; or phenyl isocyanate.

The reaction may be carried out in the presence or absence of a solvent. Suitable solvents are those that afford some solubility to the components of the reaction mixture, and do not react with the aryl isocyanate at an appreciable rate. Suitable solvents that are useful in carrying out the invention include, but are not limited to, dialkyl ethers, chlorinated hydrocarbons, tetrahydrofuran, aliphatic hydrocarbons, aromatic hydrocarbons, aliphatic alcohols, tertiary amines, dialkyl amides, dialkyl sulfoxides, dialkyl sulfones, polyalkyl phosphoric amides, and such other solvents that are known by those skilled in the art. Preferred solvents are chlorinated hydrocarbons, tetrahydrofuran, and tertiary amines. The most preferred solvent is methylene chloride.

The reaction temperature can be varied within a substantial range. In general, the reaction is carried out at from about −120° C. to about 200° C., preferably at from about −78° C. to about 100° C. The reaction is allowed to take place under normal pressure. The most preferred temperature is about 45° C.

Further treatment of this 1-substituted-4-monosubstituted-4,5-dihydropyrazole-1-carboxamide with a base, followed by alkylating agent or acylating agent will yield the N-aryl-3-aryl-4,4-disubstituted-4,5-dihydropyrazole-1-carboxamides of this invention.

The methods for effecting this reaction have been described above and are exemplified below in Example 77, Method C.

After preparing compounds embraced by Formula I by either of the above processes, the salts of the invention can be prepared by any convenient art-recognized method, such as by reacting a metal hydroxide, a metal hydride or an amine or ammonium salt, such as a halide, hydroxide or alkoxide with the free acid, or reacting a quaternary ammonium salt, such as chloride, a bromide, nitrate or the like with a metal salt of the invention in a suitable solvent. When metal hydroxides are used as reagents, useful solvents include water, glyme, dioxane, tetrahydrofuran, methanol, ethanol, isopropanol and the like. When metal hydrides are used as reagents, useful solvents include nonhydroxylic solvents such as dioxane, glyme, tetrahydrofuran, diethyl ether, hydrocarbons such as toluene, xylene, hexane, pentane, heptane, and octane, dimethylformamide, and the like. When amines are used as reagents, useful solvents include alcohols, such as methanol or ethanol, hydrocarbons, such as toluene, xylene, hexane and the like, tetrahydrofuran, glyme, dioxane, or water. When ammonium salts are used as reagents, useful solvents include water, alcohols, such as methanol or ethanol, glyme, tetrahydrofuran, or the like. When the ammonium salt is other than a hydroxide or alkoxide, an additional base, such as potassium or sodium hydroxide, hydride, or alkoxide is generally used. The particular choice of solvent will depend on the relative solubilities of the starting materials and the resultant salts, and slurries rather than solutions of certain reagents may be used to obtain the salts. Generally, equivalent amounts of the starting reagents are used and the salt-forming reaction is carried out at about 0° C. to about 100° C., preferably at about room temperature.

The acid addition salts of the present invention can be prepared by any convenient art-recognized method such as by reacting hydrochloric, hydrobromic, sulfuric, nitric, phosphoric, acetic, propionic, benzoic or other suitable acid with a compound of the present invention having a basic functionality in a suitable solvent. Useful solvents include water, alcohols, ethers, esters, ketones, haloalkanes and the like. The particular choice of solvent will depent on the relative solubilities of the starting materials and the resulting salts, and slurries rather than solutions of certain reagents may be used to obtain the salts. Generally, equivalent molar amounts of starting materials are used and the salt-forming reaction is carried out at from about −100° C. to about 100° C., preferably at about room temperature.

The following examples will further illustrate this invention but are not intended to limit it in any way. In Table I, typical 1-substituted-4-substituted-4,5-dihydro-1H-pyrazoles of the present invention are listed. Structures were confirmed by NMR and in some cases by IR and/or elemental analysis. After Table I, preparation of representative precursors or intermediates are described as Examples A through J. Following Examples A through J, specific illustrative preparations of compounds of Examples 2, 5, 34, 51, 61, 74 (see Method C, Example 77), 77, 92, 95, 98, 115, 130, 138, 145, 147, 150 and 160 are described. It will be appreciated by those skilled in the art that except for those compounds where Z is hydrogen, the Y and Z substituents can be interchanged without departing from the spirit or scope of the present invention.

TABLE I

| Example No. | A | B | Y | Z | V | U | Melting Point °C. |
|---|---|---|---|---|---|---|---|
| 1 | —C₆H₄Cl—4 | —C₆H₄Cl—4 | —CO₂CH₂CH₂SCH₃ | CH₃ | H | O | Solid |
| 2 | —C₆H₄Cl—4 | —C₆H₄Cl—4 | C₆H₅ | CH₃ | H | O | 151–153 |
| 3 | —C₆H₄Cl—4 | —C₆H₄Cl—4 | —CH₂CH(CH₃) | CH₃ | H | O | 128–130 |
| 4 | —C₆H₄Cl—4 | —C₆H₄Cl—4 | —CH₂CH₃ | CH₃ | H | O | 134–136 |
| 5 | —C₆H₄Cl—4 | —C₆H₄Cl—4 | CH₃ | —CH₂C₆H₅ | H | O | Oil |
| 6 | —C₆H₄Cl—4 | —C₆H₄Cl—4 | —CH₂CH₃ | C₆H₅ | H | O | Solid |
| 7 | —C₆H₄Cl—4 | —C₆H₄Cl—4 | —CH₂CH₂CH₃ | C₆H₅ | H | O | Solid |
| 8 | —C₆H₄Cl—4 | —C₆H₄Cl—4 | —CH(CH₃)₂ | C₆H₅ | H | O | Solid |
| 9 | —C₆H₄Cl—4 | —C₆H₄Cl—4 | —CH₂CH(CH₃)₂ | C₆H₅ | H | O | Solid |
| 10 | —C₆H₄Cl—4 | —C₆H₄Cl—4 | C₆H₅ | —CH₂C₆H₅ | H | O | Foam |
| 11 | —C₆H₄Cl—4 | —C₆H₄Cl—4 | —CH(CH₃)CH₂CH₃ | C₆H₅ | H | O | Solid |
| 12 | —C₆H₄Cl—4 | —C₆H₄Cl—4 | C₆H₅ | —CH₂CH₂CH₂CH₂Cl | H | O | Solid |
| 13 | —C₆H₄Cl—4 | —C₆H₄Cl—4 | —CH₂CH₂CH₂CH₃ | C₆H₅ | H | O | Solid |
| 14 | —C₆H₄Cl—4 | —C₆H₄Cl—4 | —CH₂CH₂CH₃ | CH₃ | H | O | Foam |
| 15 | —C₆H₄Cl—4 | —C₆H₄Cl—4 | —CH(CH₃)₂ | CH₃ | H | O | 89–92 |
| 16 | —C₆H₄Cl—4 | —C₆H₄Cl—4 | —CH₂CH₂CH₃ | CH₃ | H | O | Oil |
| 17 | —C₆H₄Cl—4 | —C₆H₄Cl—4 | —CH(CH₃)CH₂CH₃ | CH₃ | H | O | Oil |
| 18 | —C₆H₄Cl—4 | —C₆H₄Cl—4 | —CH₂CH₂CH₂Cl | CH₃ | H | O | Oil |
| 19 | —C₆H₄Cl—4 | —C₆H₄Cl—4 | C₆H₅ | —CH₂CH=CH₂ | H | O | 161–165 |
| 20 | —C₆H₄Cl—4 | —C₆H₄Cl—4 | C₆H₅ | —CH₂CO₂CH₂CH₃ | H | O | 138–142 |
| 21 | —C₆H₄Cl—4 | —C₆H₄Cl—4 | C₆H₅ | —CH₂CN | H | O | 156–158 |
| 22 | —C₆H₄Cl—4 | —C₆H₄Cl—4 | C₆H₅ | —CH₂SCH₃ | H | O | 69–71 |
| 23 | —C₆H₄Cl—4 | —C₆H₄Cl—4 | C₆H₅ | —CH₂OCH₃ | H | O | 88–93 |
| 24 | —C₆H₄Cl—4 | —C₆H₄Cl—4 | —CH(CH₂CH₃)₂ | CH₃ | H | O | 130–135 |
| 25 | —C₆H₄Br—4 | —C₆H₄Cl—4 | —CH₂CH₂CH₂CH₃ | CH₃ | —CH(CH₃)₂ | O | Oil |
| 26 | —C₆H₄Cl—4 | —C₆H₄Cl—4 | —CH₂CH₂CH₂CH₃ | CH₃ | H | O | Oil |
| 27 | —C₆H₄Cl—4 | —C₆H₄Cl—4 | —CH₂CH₂CH₂CH₂CH₃ | CH₃ | H | O | Semisolid |
| 28 | —C₆H₄F—4 | —C₆H₄Cl—4 | —CH₂CH₂CH₂CH₃ | CH₃ | H | O | Oil |
| 29 | —C₆H₄F—4 | —C₆H₄Cl—4 | CH₃ | —CH₂CH=CH₂ | H | O | Solid |
| 30 | —C₆H₄Cl—4 | —C₆H₄Cl—4 | —CH(CH₂CH₃)₂ | CH₃ | H | O | Oil |
| 31 | —C₆H₄Cl—4 | —C₆H₄Cl—4 | —CH₂SCH₃ | CH₃ | H | O | Foam |
| 32 | —C₆H₄Cl—4 | —C₆H₄Cl—4 | —CH₂OCH₃ | CH₃ | H | O | Oil |
| 33 | —C₆H₄Cl—4 | —C₆H₄Cl—4 | —CH₂CH₂CH₂CH₃ | CH₃ | H | O | Oil |
| 34 | —C₆H₄Cl—4 | —C₆H₄Cl—4 | —CH₂CH₂CH₂CH₃ | CH₃ | H | O | Oil |
| 35 | —C₆H₄Cl—4 | —C₆H₄Cl—4 | CH₃ | —CH₂CH₂OCH₃ | H | O | Solid |
| 36 | —C₆H₄Cl—4 | —C₆H₄Cl—4 | —CH₂CH₂CH₂OCH₃ | CH₃ | H | O | Solid |
| 37 | —C₆H₄Cl—4 | —C₆H₄Cl—4 | —CH₂CH₂CH₂CN | CH₃ | H | O | Oil |
| 38 | —C₆H₄Cl—4 | —C₆H₄Cl—4 | CH₃ | —CH₂CH=CH₂ | H | O | Oil |
| 39 | —C₆H₄Cl—4 | —C₆H₄Cl—4 | —CH₂OCH₂OCH₃ | CH₃ | H | O | Solid |
| 40 | —C₆H₄Cl—4 | —C₆H₄Cl—4 | —CH₂OCH₂OCH₃ | CH₃ | H | O | 60–65 |
| 41 | —C₆H₄Cl—4 | —C₆H₄Cl—4 | CH₃ | —CH₂CH₂CH₂CH=CH₂ | H | O | Solid |
| 42 | —C₆H₄Cl—4 | —C₆H₄Cl—4 | CH₃ | —CH₂CH₂SC₆H₅ | H | O | 125–128 |
| 43 | —C₆H₄Cl—4 | —C₆H₄Cl—4 | CH₃ | CH₃ | H | O | Solid |
| 44 | —C₆H₄Cl—4 | —C₆H₄Cl—4 | —COCH₃ | CH₃ | H | O | Solid |

TABLE I-continued $$Y-\overset{Z}{\underset{A=N}{C}}-CH_2 \overset{B}{\underset{N=C}{N}}-N\overset{U}{\underset{V}{N}}$$

| Example No. | A | B | Y | Z | V | U | Melting Point °C. |
|---|---|---|---|---|---|---|---|
| 45 | —C₆H₄Cl—4 | —C₆H₄Cl—4 | CH₃ | —CH(OH)CH₃ | H | O | — |
| 46 | —C₆H₄Cl—4 | —C₆H₄Cl—4 | —C₆H₄Cl—4 | CH₃ | H | O | Solid |
| 47 | —C₆H₄Cl—4 | —C₆H₄Cl—4 | —CH₂CH₂CH₃ | —C₆H₄Cl—4 | H | O | Solid |
| 48 | —C₆H₄Cl—4 | —C₆H₃Cl₂—2,4 | C₆H₅ | CH₃ | H | O | 179-181 |
| 49 | —C₆H₃Cl₂—3,4 | —C₆H₄Cl—4 | C₆H₅ | CH₃ | H | O | 110-114 |
| 50 | —C₆H₄Cl—4 | —C₆H₄Cl—4 | CH₃ | C₆H₁₁ | H | O | 162-164 |
| 51 | —C₆H₄Cl—4 | —C₆H₄Cl—4 | C₆H₅ | —CH(OH)CH₃ | H | O | 132-135 |
| 52 | —C₆H₄Cl—4 | —C₆H₄Cl—4 | —COCH₃ | CH₃ | CH₃ | O | Foam |
| 53 | —C₆H₄Cl—4 | —C₆H₄Cl—4 | —CH₂CH(CH₃)₂ | C₆H₅ | H | O | Foam |
| 54 | —C₆H₄Cl—4 | —C₆H₄Cl—4 | C₆H₅ | CH₃ | CH₃ | O | Oil |
| 55 | —C₆H₄Cl—4 | —C₆H₃Cl₂—3,4 | C₆H₅ | CH₃ | H | O | Solid |
| 56 | —C₆H₄Cl—4 | —C₆H₃Cl₂—3,5 | C₆H₅ | CH₃ | H | O | Solid |
| 57 | —C₆H₄Cl—4 | —C₆H₄Cl—3 | C₆H₅ | CH₃ | CH₃ | O | Solid |
| 58 | —C₆H₄Cl—4 | —C₆H₄Cl—4 | —C₆H₄Cl—4 | CH₃ | H | O | Solid |
| 59 | —C₆H₄Cl—4 | —C₆H₃Cl₂—3,5 | —C₆H₄Cl—4 | CH₃ | CH₃ | O | Solid |
| 60 | —C₆H₃Cl₂—3,4 | —C₆H₃Cl₂—3,5 | CH₃ | C₆H₅ | H | O | Solid |
| 61 | —C₆H₃Cl₂—3,4 | —C₆H₃Cl₂—3,5 | C₆H₅ | CH₃ | H | O | Solid |
| 62 | —C₆H₄Cl—4 | —C₆H₃Cl₂—3,5 | C₆H₅ | CH₃ | CH₃ | O | Oil |
| 63 | —C₆H₄Cl—4 | —C₆H₄Cl—4 | —CH₂OH | CH₃ | H | O | 140-147 |
| 64 | —C₆H₄Cl—4 | —C₆H₄Cl—4 | —CH₂OCOCH₃ | C₆H₅ | H | O | 146-150 |
| 65 | —C₆H₄Cl—4 | —C₆H₄Cl—4 | —CH₂CH₂CH₃ | CH₃ | H | O | Solid |
| 66 | —C₆H₄Cl—4 | —C₆H₄Cl—4 | —CH₂CH₂CH₂Cl | C₆H₅ | H | O | Solid |
| 67 | —C₆H₄Cl—4 | —C₆H₄Cl—4 | —CO₂H | CH₃ | H | O | Solid |
| 68 | —C₆H₄Cl—4 | —C₆H₄Cl—4 | —CO₂H | CH₃ | H | O | Oil |
| 69 | —C₆H₄Cl—4 | —C₆H₄Cl—4 | —CO₂Na | CH₃ | H | O | Oil |
| 70 | —C₆H₄Cl—4 | —C₆H₄Cl—4 | —CH₂CH₂SCH₃ | —CH₂CH₂CH₂CH₃ | H | O | Solid |
| 71 | —C₆H₄Cl—4 | —C₆H₄Cl—4 | —CH₂CH₂SCH₂CH₃ | C₆H₅ | H | O | Oil |
| 72 | —C₆H₄Cl—4 | —C₆H₄Cl—4 | CH₃ | —CH₂CH(OH)CH₃ | H | O | Oil |
| 73 | —C₆H₄Cl—4 | —C₆H₄Cl—4 | CH₃ | —CH₂CH₂N₃ | H | O | Oil |
| 74 | —C₆H₄Cl—4 | —C₆H₄Cl—4 | —CO₂CH₃ | H | H | O | 138-150 |
| 75 | —C₆H₄Cl—4 | —C₆H₄Cl—4 | —CO₂H | H | H | O | Solid |
| 76 | —C₆H₄Cl—4 | —C₆H₄Cl—4 | C₆H₅ | —CH₂CO₂CH₃ | H | O | Solid |
| 77 | —C₆H₄Cl—4 | —C₆H₄Cl—4 | —CO₂CH₃ | CH₃ | H | O | 125.5-126.5 |
| 78 | —C₆H₄Cl—4 | —C₆H₄Cl—4 | —CO₂CH₃ | C₆H₅ | H | O | Solid |
| 79 | —C₆H₄Cl—4 | —C₆H₄Cl—4 | —CH₂CO₂H | C₆H₅ | H | O | Solid |
| 80 | —C₆H₄Cl—4 | —C₆H₄Cl—4 | C₆H₅ | CH₃ | —CN | O | Solid |
| 81 | —C₆H₄Cl—4 | —C₆H₄Cl—4 | —CH₂CH₃ | —CH₂CH₂SO₂CH₃ | H | O | Solid |
| 82 | —C₆H₄Cl—4 | —C₆H₄Cl—4 | —CH₂SOCH₃ | —CH₂CH₃ | H | O | Solid |
| 83 | —C₆H₄Cl—4 | —C₆H₄Cl—4 | —CO₂CH₂CH₃ | CH₃ | H | O | Solid |
| 84 | —C₆H₄Cl—4 | —C₆H₄Cl—4 | —CO₂CH₂CH₃ | CH₃ | H | O | — |
| 85 | C₆H₅ | —C₆H₄Cl—4 | C₆H₅ | CH₃ | H | O | 175-176 |
| 86 | —C₆H₄Cl—4 | —C₆H₄Cl—4 | —CH₂CH₂CH₃ | CH₃ | H | O | Oil |
| 87 | —C₆H₄Cl—4 | —C₆H₄Cl—4 | C₆H₅ | CH₃ | —COCH₃ | O | Foam |
| 88 | —C₆H₄Cl—4 | —C₆H₄Cl—4 | CH₃ | —SCH₃ | H | O | Oil |

TABLE I-continued $$Y-C-CH_2 \overset{Z}{\underset{N-C=N}{\overset{U}{\underset{A}{\vert}}}} \overset{B}{\underset{V}{\vert}}$$

| Example No. | A | B | Y | Z | V | U | Melting Point °C. |
|---|---|---|---|---|---|---|---|
| 89 | —C₆H₄Cl—4 | —C₆H₄Cl—4 | —CO₂CH₂SCH₃ | CH₃ | H | O | Oil |
| 90 | —C₆H₄Cl—4 | —C₆H₄Cl—4 | —COCH₂CH₃ | CH₃ | H | O | Solid |
| 91 | —C₆H₄Cl—4 | —C₆H₄(CO₂CH₂CH₃)—4 | C₆H₅ | CH₃ | H | O | 81–83 |
| 92 | —C₆H₄Cl—4 | —C₆H₄Cl—4 | —CON(CH₃)₂ | CH₃ | H | O | 194–197 |
| 93 | —C₆H₄Cl—4 | —C₆H₄Cl—4 | CH₃ | —CN | H | O | — |
| 94 | —C₆H₄Cl—4 | —C₆H₄Cl—4 | —CH₂CH₂OH | CH₃ | H | O | Solid |
| 95 | —C₆H₄Cl—4 | —C₆H₄Cl—4 | —CO₂CH₂CH₃ | H | H | O | Solid |
| 96 | —C₆H₄Cl—4 | —C₆H₄Cl—4 | C₆H₅ | CH₃ | —CH₂OCH₃ | O | Oil |
| 97 | —C₆H₄Cl—4 | —C₆H₄Cl—4 | —CO₂CH₃ | CH₃ | CH₃ | O | 117–120 |
| 98 | —C₆H₄Cl—4 | —C₆H₄Cl—4 | —CS₂CH₃ | CH₃ | H | O | Solid |
| 99 | —C₆H₄Cl—4 | —C₆H₄(CO₂CH(CH₃)₂)—4 | C₆H₅ | CH₃ | H | O | Foam |
| 100 | —C₆H₄Cl—4 | —C₆H₄Cl—4 | —CO₂CH₂CH₂CH₃ | CH₃ | H | O | Solid |
| 101 | —C₆H₄Cl—4 | —C₆H₄Cl—4 | —CO₂CH₂CH₂CH₃ | CH₃ | H | O | Solid |
| 102 | —C₆H₄Cl—4 | —C₆H₄Cl—4 | —CO₂CH(CH₃)₂ | CH₃ | H | O | Solid |
| 103 | —C₆H₄Cl—4 | —C₆H₄Cl—4 | —CO₂CH₂CH₂N(CH₃)₂ | CH₃ | H | O | Solid |
| 104 | —C₆H₄Cl—4 | —C₆H₄Cl—4 | —CO₂CH₂CH₂N(CH₃)HCl | CH₃ | H | O | 100–103 |
| 105 | —C₆H₄Cl—4 | —C₆H₄Cl—4 | —CO₂CH₃ | CH | —CO₂CH₃ | O | Solid |
| 106 | —C₆H₄Cl—4 | —C₆H₄Cl—4 | —CH₂CHBrCH₂Br | CH₃ | H | O | Oil |
| 107 | C₆H₅ | —C₆H₄Cl—4 | —CO₂CH₃ | CH₃ | H | O | Foam |
| 108 | —C₆H₄Cl—4 | —C₆H₄Cl—4 | —CO₂CH₂CH₂SO₂CH₃ | CH₃ | H | O | Foam |
| 109 | —C₆H₄Cl—4 | —C₆H₄Cl—4 | —COC₆H₄Cl—4 | CH₃ | H | O | Solid |
| 110 | —C₆H₄Cl—4 | —C₆H₄Cl—4 | CH₃ | —CH₂CHClCH₂Cl | H | O | Solid |
| 111 | —C₆H₄Cl—4 | —C₆H₄Cl—4 | —COCH₂CH₂CH₃ | CH₃ | H | O | Foam |
| 112 | —C₆H₄Cl—4 | —C₆H₄Cl—4 | —COC₆H₅ | CH₃ | H | O | Solid |
| 113 | —C₆H₄Cl—4 | —C₆H₄Cl—4 | —CON(CH₂CH₃)₂ | CH₃ | H | O | 147–149 |
| 114 | —C₆H₄Cl—4 | —C₆H₄Cl—4 | —CO₂CH₃ | CH₃ | —COCH₃ | O | Oil |
| 115 | —C₆H₄Cl—4 | —C₆H₄Cl—4 | —CON(CH₃)₂ | CH₃ | —COCH₃ | O | Oil |
| 116 | C₆H₅ | —C₆H₄Cl—4 | —CON(CH₂CH₃) | CH₃ | H | O | Solid |
| 117 | C₆H₅ | —C₆H₄Cl—4 | —CON(CH₃)₂ | CH₃ | H | O | Solid |
| 118 | —C₆H₄Cl—4 | —C₆H₄Cl—4 | C₆H₅ | CH₃ | —COCH₂CH₃ | O | Solid |
| 119 | —C₆H₄Cl—4 | —C₆H₄Cl—4 | C₆H₅ | CH₃ | —COC(CH₃)₃ | O | Solid |
| 120 | —C₆H₄Cl—4 | —C₆H₄Cl—4 | —CON(CH₃)₂ | CH₃ | —CO₂CH₃ | O | Solid |
| 121 | —C₆H₄Cl—4 | —C₆H₄Cl—4 | C₆H₅ | H | H | O | Solid |
| 122 | —C₆H₄Cl—4 | —C₆H₄Cl—4 | —CO₂CH₃ | CH₃ | —COC₆H₅ | O | Oil |
| 123 | —C₆H₄Cl—4 | —C₆H₄Cl—4 | —CO₂CH₃ | CH₃ | —COCF₃ | O | — |
| 124 | —C₆H₄Cl—4 | —C₆H₄Cl—4 | —CO₂CH₃ | CH₃ | —CHO | O | Solid |
| 125 | —C₆H₄Cl—4 | —C₆H₄Cl—4 | —CO₂CH₃ | CH₃ | —CH₂OCH₃ | O | Solid |
| 126 | —C₆H₄Cl—4 | —C₆H₄Cl—4 | —CO₂CH₃ | CH₃ | —CO₂CH₂CH₃ | O | Solid |
| 127 | —C₆H₄Cl—4 | —C₆H₄Cl—4 | —CO₂CH₃ | CH₃ | —CO₂CH=CH₂ | O | Solid |
| 128 | —C₆H₄Cl—4 | —C₆H₄Cl—4 | —CO₂CH₃ | CH₃ | —CO₂C₆H₅ | O | Solid |
| 129 | —C₆H₄Cl—4 | —C₆H₄Cl—4 | —CSN(CH₃)₂ | CH₃ | H | O | — |
| 130 | —C₆H₄Cl—4 | —C₆H₄Cl—4 | —CO₂CH₃ | CH₃ | H | S | 69–78 |
| 131 | —C₆H₄Cl—4 | —C₆H₄Cl—4 | —CO₂CH₃ | CH₃ | —COCH₃ | S | 138–141 |
| 132 | C₆H₅ | —C₆H₄F—4 | —CO₂CH₃ | CH₃ | H | O | 115–119 |

TABLE I-continued $$Y-\overset{Z}{\underset{A-C\equiv N}{C}}-CH_2-N-\overset{U}{\underset{\|}{C}}-N\overset{B}{\underset{V}{\diagdown}}$$

| Example No. | A | B | Y | Z | V | U | Melting Point °C. |
|---|---|---|---|---|---|---|---|
| 133 | C$_6$H$_5$ | —C$_6$H$_4$Br—4 | —CO$_2$CH$_3$ | CH$_3$ | H | O | 130–136 |
| 134 | —C$_6$H$_4$F—4 | —C$_6$H$_4$Br—4 | —CO$_2$CH$_3$ | CH$_3$ | H | O | 168–173 |
| 135 | —C$_6$H$_4$F—4 | —C$_6$H$_4$Br—4 | —CO$_2$CH$_3$ | CH$_3$ | H | O | 154–158 |
| 136 | —C$_6$H$_4$F—4 | —C$_6$H$_4$F—4 | —CO$_2$CH$_3$ | CH$_3$ | H | O | 143–145 |
| 137 | —C$_6$H$_4$Cl—4 | —C$_6$H$_4$Cl—4 | —CO$_2$CH$_3$ | CH$_3$ | —CO$_2$CH$_3$ | O | 100–103 |
| 138 | —C$_6$H$_4$Cl—4 | —C$_6$H$_4$Cl—4 | —CO$_2$CH$_3$ | CH$_3$ | —CON(CH$_3$)$_2$ | O | Solid |
| 139 | C$_6$H$_5$ | —C$_6$H$_4$Cl—4 | —CO$_2$CH$_3$ | CH$_3$ | —CO$_2$CH$_3$ | O | Solid |
| 140 | —C$_6$H$_4$Br—4 | —C$_6$H$_4$F—4 | —CO$_2$CH$_3$ | CH$_3$ | H | O | Oil |
| 141 | —C$_6$H$_4$Cl—4 | —C$_6$H$_4$Cl—4 | —CO$_2$CH$_3$ | CH$_3$ | —COCO$_2$CH$_3$ | O | 78–87 |
| 142 | —C$_6$H$_4$Cl—4 | —C$_6$H$_4$F—4 | —CO$_2$CH$_3$ | CH$_3$ | H | O | 148–151 |
| 143 | —C$_6$H$_4$Cl—4 | —C$_6$H$_4$F—4 | —CO$_2$CH$_3$ | CH$_3$ | H | O | 105–110 |
| 144 | —C$_6$H$_4$Cl—4 | —C$_6$H$_4$Cl—4 | C$_6$H$_5$ | CH$_3$ | —SCO$_2$CH$_3$ | O | Foam |
| 145 | —C$_6$H$_4$Cl—4 | —C$_6$H$_4$Cl—4 | —CO$_2$CH$_3$ | CH$_3$ | —SCO$_2$CH$_3$ | O | Foam |
| 146 | —C$_6$H$_4$Cl—4 | —C$_6$H$_4$Cl—4 | —CO$_2$CH$_3$ | CH$_3$ | H | O | Oil |
| 147 | —C$_6$H$_4$Br—4 | —C$_6$H$_4$Br—4 | —CO$_2$CH$_3$ | CH$_3$ | H | O | 114–117 |
| 148 | —C$_6$H$_4$CF$_3$—4 | —C$_6$H$_4$Cl—4 | —CO$_2$CH$_3$ | CH$_3$ | H | O | 145–149 |
| 149 | —C$_6$H$_4$Cl—4 | —C$_6$H$_4$CF$_3$—4 | —CO$_2$CH$_3$ | CH$_3$ | H | O | 143–146 |
| 150 | —C$_6$H$_4$Cl—4 | —C$_6$H$_4$Cl—4 | —CO$_2$CH$_3$ | CH$_3$ | —SC$_6$H$_4$NO$_2$—2 | O | — |
| 151 | —C$_6$H$_4$Cl—4 | —C$_6$H$_4$Cl—4 | —CO$_2$CH$_3$ | CH$_3$ | —SCH$_2$CH$_2$CH$_3$ | O | Oil |
| 152 | —C$_6$H$_4$CF$_3$—4 | —C$_6$H$_4$Cl—4 | —CO$_2$CH$_3$ | CH$_3$ | H | O | 165–167 |
| 153 | —C$_6$H$_4$Cl—4 | —C$_6$H$_4$CH(CH$_3$)$_2$—4 | —CO$_2$CH$_3$ | CH$_3$ | H | O | 58–60 |
| 154 | —C$_6$H$_4$Cl—4 | —C$_6$H$_4$OCH$_3$—4 | —CO$_2$CH$_3$ | CH$_3$ | H | O | 120–122 |
| 155 | —C$_6$H$_4$Cl—4 | —C$_6$H$_4$SCH$_3$—4 | —CO$_2$CH$_3$ | CH$_3$ | H | O | 114–116 |
| 156 | —C$_6$H$_4$Cl—4 | —C$_6$H$_4$SO$_2$CH$_3$—4 | —CO$_2$CH$_3$ | CH$_3$ | H | O | 179–182 |
| 157 | —C$_6$H$_4$Cl—4 | —C$_6$H$_4$CH$_3$—4 | —CO$_2$CH$_3$ | CH$_3$ | H | O | 122–125 |
| 158 | —C$_6$H$_4$Cl—4 | —C$_6$H$_4$Cl—4 | —CO$_2$CH$_3$ | CH$_3$ | —SC$_6$H$_5$ | O | Solid |
| 159 | —C$_6$H$_4$Cl—4 | —C$_6$H$_4$Cl—4 | —CO$_2$CH$_3$ | CH$_3$ | —SCH$_2$CH$_2$CH$_2$CN | O | Oil |
| 160 | —C$_6$H$_4$Cl—4 | —C$_6$H$_4$Cl—4 | —CO$_2$CH$_3$ | CH$_3$ | —SCH$\overset{CH_3}{\underset{CH_2CO_2CH_3}{\diagup}}$ | O | — |
| 161 | —C$_6$H$_4$Cl—4 | —C$_6$H$_4$Cl—4 | —CO$_2$CH$_3$ | CH$_3$ | —SCH$_3$ | O | — |
| 162 | —C$_6$H$_4$Cl—4 | —C$_6$H$_4$SOCH$_3$—4 | —CO$_2$CH$_3$ | CH$_3$ | H | O | — |
| 163 | —C$_6$H$_4$Cl—4 | —C$_6$H$_4$I—4 | —CO$_2$CH$_3$ | CH$_3$ | H | O | Oil |
| 164 | —C$_6$H$_4$Cl—4 | —C$_6$H$_4$N(CH$_3$)$_2$—4 | —CO$_2$CH$_3$ | CH$_3$ | H | O | 120–123 |
| 165 | —C$_6$H$_4$Cl—4 | —C$_6$H$_4$Cl—4 | —COCH(CH$_3$)$_2$ | CH$_3$ | H | O | 145–146 |
| 166 | —C$_6$H$_4$Cl—4 | —C$_6$H$_4$Cl—4 | —COC(CH$_3$)$_3$ | CH$_3$ | H | O | 73–75 |
| 167 | —C$_6$H$_4$Cl—4 | —C$_6$H$_4$N(CH$_3$)$_3^+$I$^-$)—4 | —CO$_2$CH$_3$ | CH$_3$ | H | O | 211–212 |
| 168 | —C$_6$H$_4$Cl—4 | —C$_6$H$_4$N(CH$_3$)$_2$O)—4 | —CO$_2$CH$_3$ | CH$_3$ | H | O | Oil |
| 169 | —C$_6$H$_4$Cl—4 | —C$_6$H$_4$CF$_3$—3 | —CO$_2$CH$_3$ | CH$_3$ | H | O | Solid |
| 170 | —C$_6$H$_4$Cl—4 | —C$_6$H$_4$Cl—3 | —CO$_2$CH$_3$ | CH$_3$ | H | O | — |
| 171 | —C$_6$H$_4$Cl—4 | —C$_6$H$_4$SCH$_3$—3 | —CO$_2$CH$_3$ | CH$_3$ | H | O | Solid |

TABLE I-continued $$Y-C-CH_2-N-C-N \begin{matrix} B \\ V \end{matrix}$$
$$Z \qquad U$$
$$A-C=N$$

| Example No. | A | B | Y | Z | U | V | Melting Point °C. |
|---|---|---|---|---|---|---|---|
| 172 | —C₆H₄Cl—4 | —C₆H₄SO₂CH₃—3 | —CO₂CH₃ | CH₃ | O | H | Foam |
| 173 | —C₆H₄Cl—4 | —C₆H₄Cl—4 | CH₃ | —CHOHC₆H₄F—4 | O | H | 186–187 |
| 174 | —C₆H₄CH₃—4 | —C₆H₄Cl—4 | —CO₂CH₃ | CH₃ | O | H | 127–128 |
| 175 | —C₆H₄OCH₃—4 | —C₆H₄Cl—4 | —CO₂CH₃ | CH₃ | O | H | 148–149 |
| 176 | —C₆H₄Cl—4 | —C₆H₄Cl—4 | —CO₂CH₃ | —CH₂CH₃ | O | H | 141–143 |
| 177 | —C₆H₄Cl—4 | —C₆H₄CF₃—4 | —CON(CH₃)₂ | CH₃ | O | H | 152–155 |
| 178 | —C₆H₄Cl—4 | —C₆H₄Cl—4 | —CO₂CH₃ | CH₃ | O | H | 131–133 |
| 179 | —C₆H₄SCH₃—4 | —C₆H₄Cl—4 | —CO₂CH₃ | CH₃ | O | H | 133–135 |
| 180 | C₆H₅ | —C₆H₃Cl₂—3,4 | —CO₂CH₃ | CH₃ | O | H | 127–130 |
| 181 | C₆H₅ | —C₆H₄Cl—4 | —CO₂CH₃ | CH₃ | O | H | 205–207 |
| 182 | —C₆H₄SO₂CH₃—4 | C₆H₅ | —CO₂CH₃ | CH₃ | O | H | 116–119 |
| 183 | —C₆H₄Cl—4 | —C₆H₃Cl₂—3,4 | —CO₂CH₃ | CH₃ | O | H | 132–134 |
| 184 | —C₆H₄Cl—4 | —C₆H₄Cl—4 | —CO₂-[cyclohexyl with CH₃, CH(CH₃)₂] | CH₃ | O | H | 176–178 |
| 185 | —C₆H₄Cl—4 | —C₆H₄CF₃—4 | —CO₂CH₂CH₃ | CH₃ | O | H | 122–124 |
| 186 | —C₆H₄Cl—4 | —C₆H₄OCF₃—4 | —CO₂CH₃ | CH₃ | O | H | 47–49 |
| 187 | —C₆H₄Cl—4 | —C₆H₃CF₃—3,Cl—4 | —CO₂CH₃ | CH₃ | O | H | 154–155 |
| 188 | —C₆H₄Cl—4 | —C₆H₃CH₃—3,Br—4 | —CO₂CH₃ | H | O | H | 122–130 |
| 189 | —C₆H₄Cl—4 | —C₆H₄CO₂CH₂CH₃—4 | —CO₂CH₃ | H | O | H | 138–140 |
| 190 | —C₆H₄Cl—4 | —C₆H₄CO₂CH₃—4 | —CO₂CH₃ | CH₃ | O | H | 138–141 |
| 191 | —C₆H₄Cl—4 | naphthyl | —CO₂CH₃ | CH₃ | O | H | 188–190 |
| 192 | C₆H₅ | —C₆H₄CF₃—4 | —CO₂CH₂CH₃ | CH₃ | O | H | 149–150 |
| 193 | —C₆H₄Cl—4 | —C₆H₃(NO₂)₂—2,4 | —CO₂CH₃ | CH₃ | O | H | 196–198 |
| 194 | —C₆H₄Cl—4 | —C₆H₄NO₂—4 | —CO₂CH₃ | CH₃ | O | H | 135–140 |
| 195 | C₆H₅ | —C₆H₄CF₃—4 | —CON(CH₃)₂ | CH₃ | O | H | 186–188 |
| 196 | —C₆H₄Cl—4 | —C₆H₄Cl—4 | CH₃ | —COH(CH₃)₂ | O | H | Oil |

EXAMPLE A

Preparation of 4-chlorophenyl benzyl ketone

To a 2 liter 4 necked flask equipped with a mechanical stirrer thermometer, and reflux condensor was added 155 g (1.0 mole) of phenyl acetyl chloride and 500 ml (4.9 mole) of chlorobenzene. A total of 145 g (1.08 mole) of anhydrous aluminum chloride was added portionwise over 10 minutes. The mixture self warmed to 55° C. and evolved HCl gas over the course of the next 30 minutes. The mixture was stirred at about 50° C. for an additional 30 minutes and then poured onto about 500 g of ice and 110 ml of concentrated aqueous HCl. The organic layer (lower) was separated and the aqueous layer was washed with ethyl ether. The combined organic layers were washed with water, dilute aqueous NaOH, and water and then concentrated in vacuo. The resulting crude solid was recrystallized from 2200 ml of hexane yielding 132 g of 4-chlorophenyl benzyl ketone, mp 85°-90° C.

EXAMPLE B

Preparation of 2-phenyl 4'-chlorophenyl acrylophenone

In a 1000 ml round bottomed flask equipped with a reflux condensor was placed 100 g 4-chlorophenyl benzyl ketone (0.43 mole), 400 ml of methanol, 50 ml of 37% formalin (0.67 mole), 5 g of piperidine, and 5 g of acetic acid. The resulting mixture was refluxed for 2 hours, concentrated in vacuo, partitioned between ethyl ether and water, washed with water, dried over anhydrous magnesium sulfate and concentrated in vacuo to yield 98 g of 2-phenyl 4'-chlorophenyl acrylophenone, an oil.

EXAMPLE C

Preparation of 3-(4-chlorophenyl)-4-phenyl-4,5-dihydro-1H-pyrazole

In a 500 ml round bottomed flask equipped with a reflux condensor was mixed 98 g of 2-phenyl 4'-chlorophenyl acrylophenone (0.40 mole), 200 ml n-propanol, and 50 ml hydrazine monohydrate (1.0 mole). The mixture was refluxed for 1 hour, cooled slightly and 100 ml of methanol added. The resulting solution was cooled in an ice bath and the resulting solid filtered and washed twice with cold ethyl ether yielding 55 g of a white solid. mp 156°-162° C.

EXAMPLE D

Preparation of N,3-bis-(4-chlorophenyl)-4-phenyl-4,5-dihydro-1H-pyrazole-1-carboxamide In a 500 ml round bottomed flask was suspended 55 g of 3-(4-chlorophenyl)-4-phenyl-4,5-dihydro-1H-pyrazole in 250 ml of diethyl ether. The suspension was warmed to reflux and 33 g of 4-chlorophenyl isocyanate was added at a rate to maintain reflux. After cooling and standing overnight the precipitated product was filtered yielding 78 g of white solid. mp 173°-175° C.

EXAMPLE E

Preparation of 3-dimethylamino-2-methyl-4'-chloropropiophenone

In a 500 ml round bottomed flask equipped with a reflux condensor was mixed 84 g of 4-chloropropiophenone (0.50 mole), 50 g of dimethylamine hydrochloride (0.61 mole), 20 g of paraformaldehyde (0.67 mole), 50 ml of ethanol, and 10 ml of concentrated aqueous hydrochloric acid. The mixture was refluxed for 18 hours, cooled and partitioned between ethyl ether and water. The ether layer was discarded and the aqueous layer was basified with sodium hydroxide and the resulting mixture extracted twice with fresh ethyl ether. The combined organic layers were washed with brine, dried over magnesium sulfate and concentrated in vacuo to yield 105 g of 3-dimethylamino-2-methyl-4'-chloropropiophenone, an oil.

EXAMPLE F

Preparation of 3-(4-chlorophenyl)-4-methyl-4,5-dihydro-1H-pyrazole

In a 500 ml round bottomed flask equipped with a reflux condensor was placed 100 g of 3-dimethylamino-2-methyl-4'-chloropropiophenone (0.47 mole), 200 ml of n-propanol, 48 g of hydrazine monohydrate (0.96 mole), and 5 g of 50% aqueous sodium hydroxide. The mixture was refluxed for 2 hours. The solvent was removed in vacuo and the product was partitioned between methylene chloride and water. The organic layer was washed 3 times with water and dried over anhydrous magnesium sulfate. The organic layer contains 82 g (0.42 mole) of 3-(4-chlorophenyl)-4-methyl-4,5-dihydro-1H-pyrazole an air sensitive solid.

EXAMPLE G

Preparation of N,3-bis-(4-chlorophenyl)-4-methyl-4,5-dihydro-1H-pyrazole-1-carboxamide In a 500 ml round bottomed flask was placed 82 g (0.42 mole) of 3-(4-chlorophenyl)-4-methyl-4,5-dihydro-1H-pyrazole dissolved in 300 ml of methylene chloride and the solution was brought to boiling. A solution of 64.5 g of 4-chlorophenyl isocyanate (0.42 mole) in 100 ml of methylene chloride was added at a rate to maintain reflux. After stirring for an additional 30 minutes the solvent was removed in vacuo and the resulting oil was crystallized from ethyl ether yielded 140 g of N,3-bis-(4-chlorophenyl)-4-methyl-4,5-dihydro-1H-pyrazole-1-carboxamide. mp 139°-140° C.

EXAMPLE H

Preparation of 3,4-dichlorophenyl benzyl carbinol

Into a 1000 ml three necked flask equiped with a reflux condenser and an addition funnel was placed 8.8 g of magnesium turnings (0.36 mole) and 400 ml of diethyl ether. After activation of the magnesium with 0.02 g of iodine, the mixture was heated to reflux and a solution of 44 g (0.35 mole) of benzyl chloride in ethyl ether was added at a rate to maintain the reflux. When the reaction had subsided, a solution of 50 g (0.29 mole) of 3,4-dichlorobenzaldehyde in 75 ml of diethyl ether was added at a rate to maintain reflux. After 15 minutes, the reaction was quenched with water and acidified with dilute hydrochloric acid. The organic layer was washed with brine, dried, and concentrated in vacuo yielding 75 g of 3,4-dichlorophenyl benzyl carbinol which was used without further purification.

EXAMPLE I

Preparation of 3,4-dichlorophenyl benzyl ketone

In a 500 ml round bottomed flask was placed 75 g of crude 3,4-dichlorophenyl benzyl carbinol and 300 ml of acetone. The reaction mixture was cooled to 0° C. and a solution of 20 g of chromic anhydride and 17.25 ml of concentrated sulfuric acid in 60 ml of water was added at a rate to keep the internal temperature below 5° C. After stirring an additional 15 minutes, the reaction was quenched with 10 ml of isopropanol and partitioned between ethyl ether and water. The organic layer was washed with brine, dried, and concentrated. The resulting crude ketone was crystallized from hexane yielding 51 g of 3,4-dichlorophenyl benzyl ketone.

EXAMPLE J

Preparation of Methyl 3-(4-chlorophenyl)-3-keto-propanoate

Into a 1000 ml three necked flask equipped with an addition funnel, and condenser was added 15.4 g of 60% sodium hydride (0.63 mole). The sodium hydride was washed twice with hexane and then suspended in 300 ml of tetrahydrofuran and 29 g of dimethyl carbonate (0.32 mole). The reaction mixture was brought to reflux and a solution of 50 g (0.32 mole) of 4-chloroacetophenone in 50 ml of tetrahydrofuran was added over 30 minutes. After hydrogen evolution had ceased the reaction was cooled and poured onto ice. The aqueous layer was acidified with hydrochloric acid and extracted with ethyl ether. The organic layer was dried, concentrated, and distilled at 15 torr bp 180°-205° C. to give 40 g of methyl 3-(4-chlorophenyl)-3-keto-propanoate.

EXAMPLE 2

Preparation of N,3-bis-(4-chlorophenyl)-4-methyl-4-phenyl-4,5-dihydro-1H-carboxamide To 2.1 g of diisopropylamine dissolved in 15 ml of tetrahydrofuran and cooled in an ice salt bath was added 8.0 ml of a 2.7 molar solution of n-butyllithium in hexane. After stirring for 5 minutes a solution of 4.2 g of N,3-bis-(4-chlorophenyl)-4-phenyl-4,5-dihydro-1H-pyrazole-1-carboxamide (Example D) in 15 ml of tetrahydrofuran was added and the resulting solution stirred for 15 minutes. To this solution was added 1.0 ml of iodomethane and, after 15 minutes 1.0 ml of acetic acid was added. The reaction mixture was partitioned between diethyl ether and water and the organic layer was dried over anhydrous magnesium sulfate. The resulting solution was filtered evaporated in vacuo to give 4.3 g of N,3-bis-(4-chlorophenyl)-4-phenyl-4-methyl-4,5-dihydro-1H-pyrazole-1-carboxamide, melting point 151°-158° C. NMR and IR data were consistent with the structure.

EXAMPLE 5

Preparation of N,3-bis-(4-chlorophenyl)-4-benzyl-4-methyl-4,5-dihydro-1H-pyrazole-1-carboxamide To 2.1 g of diisopropylamine dissolved in 15 ml of tetrahydrofuran and cooled in an ice salt bath was added 8.0 ml of a 2.7 molar solution of n-butyllithium in hexane. After stirring for 5 minutes a solution of 3.4 g of N,3-bis-(4-chlorophenyl)-4-methyl-4,5-dihydro-1H-pyrazole-1-carboxamide (Example G) in 15 ml of tetrahydrofuran was added and the resulting solution stirred for 15 minutes. To this solution was added 1.5 ml of benzyl bromide and, after 5 minutes 1.5 ml of acetic acid was added. The reaction mixture was partitioned between diethyl ether and water and the organic layer was dried over anhydrous magnesium sulfate. The resulting solution was filtered evaporated in vacuo to give 3.90 g of N,3-bis-(4-chlorophenyl)-4-benzyl-4-methyl-4,5-dihydro-1H-pyrazole-1-carboxamide, an oil. NMR and IR data were consistent with the structure.

EXAMPLE 34

Preparation of N-(4-bromophenyl)-3-(4-fluorophenyl)-4-butyl-4-methyl-4,5-dihydro-1H-pyrazole-1-carboxamide To 2.1 g of diisopropylamine dissolved in 15 ml of tetrahydrofuran and cooled in an ice salt bath was added 8.0 ml of a 2.7 molar solution of n-butyllithium in hexane. After stirring for 5 minutes a solution of 3.7 g of N-(4-bromophenyl)-3-(4-fluorophenyl)-4-methyl-4,5-dihydro-1H-pyrazole-1-carboxamide (prepared from 4-fluoropropiophenone and 4-bromophenyl isocyanate by a method analogous to that described above in Examples E, F, and G) in 15 ml of tetrahydrofuran was added and the resulting solution stirred for 15 minutes. To this solution was added 1.5 ml of 1-iodobutane and, after 15 minutes 1.5 ml of acetic acid was added. The reaction mixture was partitioned between diethyl ether and water and the organic layer was dried over anhydrous magnesium sulfate. The resulting solution was filtered evaporated in vacuo and chromatographed to give 2.9 g of N-(4-bromophenyl)-3-(4-fluorophenyl)-4-butyl-4-methyl-4,5-dihydro-1H-pyrazole-1-carboxamide an oil that solidifed on long standing. NMR and IR data were consistent with the structure.

EXAMPLE 51

Preparation of N,3-bis-(4-chlorophenyl)-N,4-dimethyl-4-phenyl-4,5-dihydro-1H-pyrazole-1-carboxamide To a 100 ml round bottomed flask was added 0.40 g (0.01 mole) of 60% sodium hydride. The sodium hydride was washed twice with hexane and 10 ml of dimethylformamide was added. Then, 2.1 g (0.05 mole) N,3-bis-(4-chlorophenyl)-4-methyl-4-phenyl-4,5-dihydro-1H-pyrazole-1-carboxamide (Example 2) was added portionwise. After hydrogen evolution ceased 1 ml of iodomethane was added and the mixture was stirred for 1 hour. The reaction mixture was partitioned between ether and water and the organic layer dried, filtered, concentrated, and chromatographed yielding 1.5 g of N,3-bis-(4-chlorophenyl)-N,4-dimethyl-4-phenyl-4,5-dihydro-1H-pyrazole-1-carboxamide. Mp 132°-135° C. NMR and IR data were consistent with the structure.

EXAMPLE 61

Preparation of N,3-bis-(3,4-dichlorophenyl)-4-methyl-4-phenyl-4,5-dihydro-1H-pyrazole-1-carboxamide 3,4-dichlorophenyl benzyl ketone was used, by substantially following the procedures given in Examples B, C, and D, to prepare N,3-bis-(3,4-dichlorophenyl)-4-phenyl-4,5-dihydro-1H-pyrazole-1-carboxamide, which was used, by substantially following the procedures given in Example 2, prepare N,3-bis-(3,4-dichlorophenyl)-4-methyl-4-phenyl-4,5-dihydro-1H-pyrazole-1-carboxamide, an oil that solidified on long standing. NMR and IR data were consistent with the structure.

EXAMPLE 77

Preparation of
N,3-bis-4-(4-chlorophenyl)-4-carbomethoxy-4-methyl-4,5-dihydro-1H-pyrazole-1-carboxamide

Method A

To 2.1 ml of diisopropylamine dissolved in 15 ml of tetrahydrofuran and cooled in an ice salt bath was added 8.0 ml of a 2.7 molar solution of n-butyllithium in hexane. After stirring for 5 minutes a solution of 3.4 g of N,3-bis-(4-chlorophenyl)-4-methyl-4,5-dihydro-1H-pyrazole-1-carboxamide in 7 ml of tetrahydrofuran was added and the resulting solution stirred for 15 minutes. To this solution was added 1.5 ml of dimethylcarbonate and, after 15 minutes 1.5 ml of acetic acid was added. The reaction mixture was partitioned between diethyl ether and water and the organic layer was dried over anhydrous magnesium sulfate. The resulting solution was filtered evaporated in vacuo to give 3.0 g of N,3-bis(4-chlorophenyl)-4-carbomethoxy-4-methyl-4,5-dihydro-1H-pyrazole-1-carboxamide, mp 122° C. NMR and IR data were consistent with the structure.

Method B

To 3.4 g of N,3-bis-(4-chlorophenyl)-4-methyl-4,5-dihydro-1H-pyrazole-1-carboxamide and 1.1 g of diisopropylamine dissolved in 20 ml of tetrahydrofuran and cooled in an acetone bath maintained at −20° C., was added 8.0 ml of a 2.7 molar solution of butyllithium in hexane. The resulting solution was stirred for 20 minutes and then cooled to −70° C. To this solution was added 0.9 ml of methyl chloroformate. The reaction was allowed to stir for 10 minutes and then allowed to warm to room temperature over 10 minutes. The reaction was quenched with 1.0 ml of acetic acid and the reaction mixture was partitioned between diethyl ether and water and the organic layer was dried over anhydrous magnesium sulfate. The resulting solution was filtered evaporated in vacuo to give 2.9 g of N,3-bis-(4-chlorophenyl)-4-carbomethoxy-4-methyl-4,5-dihydro-1H-pyrazole-1-carboxamide. NMR and IR data were consistent with the structure.

Method C

To 20.0 g of methyl 3-(4-chlorophenyl)-3-ketopropanoate in 100 ml of methanol was added a mixture of 4.7 g of hydrazine monohydrate and 7.6 g of 37% formalin in 50 ml of methanol. The reaction was stirred at room temperature for 18 hrs. The methanol was then removed in vacuo and the product was dissolved in 400 ml of methylene chloride and washed 5 times with 100 ml portions of water. The methylene chloride layer was dried over anhydrous magnesium sulfate and evaporated in vacuo to yield 22 g of 3-(4-chlorophenyl)-4-carbomethoxy-4,5-dihydro-1H-pyrazole-1-carboxamide which was used without further purification in the next reaction.

To 22 g of 3-(4-chlorophenyl)-4-carbomethoxy-4,5-dihydro-1H-pyrazole obtained from the previous reaction was added 200 ml of methylene chloride and the resulting solution was brought to reflux, whereupon 14.5 g of 4-chlorophenyl isocyanate in 25 ml of methylene chloride was added at a rate to maintain a controlled reflux. After refluxing a further 15 minutes the mixture was cooled, filtered and evaporated in vacuo yielding 14 g of N,3-bis-(4-chlorophenyl)-4-carbomethoxy-4,5-dihydro-1H-pyrazole-1-carboxamide (Example 74) which was purified by column chromatography. NMR and IR data were consistent with the structure.

To 0.9 ml of diisopropylamine in 10 ml of tetrahydrofuran under a nitrogen atmosphere and cooled to −30° C. was added 2.4 ml of a 2.6 molar solution of n-butyllithium in hexane. To this reaction mixture was added 1.0 g of 3-(4-chlorophenyl)-4-carbomethoxy-4,5-dihydro-1H-pyrazole in 5 ml of tetrahydrofuran. After stirring for 15 minutes, 0.6 ml of iodomethane was added and the mixture was warmed to room temperature and stirred for 1 hr. Quenching with 1.4 ml of 10% aqueous acetic acid and 5 ml of water and standard ether water workup gave 1.1 g of N,3-bis-(4-chlorophenyl)-4-carbomethoxy-4-methyl-4,5-dihydro-1H-pyrazole-1-carboxamide, melting point 138°–150° C. NMR and IR data were consistent with the structure.

EXAMPLE 92

Preparation of
N,3-bis-(4-chlorophenyl)-4-dimethylcarbamoyl-4-methyl-4,5-dihydro-1H-pyrazole-1-carboxamide Into a 3000 ml three necked flask equipped with a mechanical stirrer, thermometer, and addition funnel was placed 65 ml of diisopropylamine (0.47 mole), 155 g (0.45 mole) of N,3-bis-(4-chlorophenyl)-4-methyl-4,5-dihydro-1H-pyrazole-1-carboxamide and 1000 ml of tetrahydrofuran. The atmosphere was exchanged for nitrogen and the mixture was cooled to −20° C. internal. Then 375 ml of 2.6M n-butyllithium in hexane (0.97 mole) was added at a rate to maintain the internal temperature below −10° C. The mixture was stirred for an additional 30 minutes at −20° C. and then cooled to −60° C. whereon 45 ml of dimethylcarbamoyl chloride (0.49 mole) was added in one portion. After stirring for 15 minutes the reaction was quenched with 35 ml of acetic acid and 100 ml of water. After warming to room temperature, the organic layer was separated, dried over magnesium sulfate and concentrated in vacuo. Crystallization from ethyl ether gave 125 g of N,3-bis-(4-chlorophenyl)-4-dimethylcarbamoyl-4-methyl-4,5-dihydro-1H-pyrazole-1-carboxamide. Mp 194°–197° C. NMR and IR data were consistent with the structure.

EXAMPLE 95

Preparation of
N,3-bis-4-(4-chlorophenyl)-4-carboethoxy-4,5-dihydro-1H-pyrazole-1-carboxamide To 3.2 g of N,3-bis-(4-chlorophenyl)-4,5-dihydro-1H-pyrazole-1-carboxamide dissolved in 20 ml of tetrahydrofuran and cooled in an acetone bath maintained at −20° C., was added 1.5 ml of diisopropyl amine and 8.0 ml of a 2.7 molar solution of butyllithium in hexane. The resulting solution was stirred for 20 minutes and then cooled to −70° C. To this solution was added 0.5 ml of ethyl chloroformate. The reaction was allowed to stir for 10 minutes and then allowed to warm to room temperature over 10 minutes. The reaction was quenched with 1.0 ml of acetic acid and the reaction mixture was partitioned between diethyl ether and water and the organic layer was dried over anhydrous magnesium sulfate. The resulting solution was filtered evaporated in vacuo to give 3.3 g of N,3-bis-(4-chlorophenyl)-4-carboethoxy-4,5-dihydro-1H-pyrazole-1-carboxamide.
NMR and IR data were consistent with the structure.

EXAMPLE 98

Preparation of
N,3-bis-4-(4-chlorophenyl)-4-dithiocarbomethoxy-4-methyl-4,5-dihydro-1H-pyrazole-1-carboxamide To 2.3 g of diisopropylamine dissolved in 15 ml of tetrahydrofuran and cooled in an ice salt bath was added 8.0 ml of a 2.7 molar solution of n-butyllithium in hexane. After stirring for 5 minutes a solution of 3.4 g of N,3-bis-(4-chlorophenyl)-4-methyl-4,5-dihydro-1H-pyrazole-1-carboxamide in 7 ml of tetrahydrofuran was added and the resulting solution stirred for 15 minutes. To this solution was added 1.5 ml of carbon disulfide and, after 15 minutes, 1.5 ml of methyl iodide was added. Stirring was continued for 1 hour. The reaction mixture was partitioned between diethyl ether and water and the organic layer was dried over anhydrous magnesium sulfate. The resulting solution was filtered and evaporated in vacuo to give 2.7 g of N,3-bis-(4-chlorophenyl)-4-dithiocarbomethoxy-4-methyl-4,5-dihydro-1H-pyrazole-1-carboxamide. NMR and IR data were consistent with the structure.

EXAMPLE 115

Preparation of
N,3-bis-(4-chlorophenyl)-4-dimethylcarbamoyl-4-methyl-N-acetyl-4,5-dihydro-1H-pyrazole-1-carboxamide In a 50 ml round bottomed flask was placed 0.45 g of 60% sodium hydride (0.011 mole). The sodium hydride was washed twice with hexane and suspended in 15 ml of tetrahydrofuran. A solution of 2.0 g (0.005 mole) of N,3-bis-(4-chlorophenyl)-4-dimethylcarbamoyl-4-methyl-4,5-dihydro-1H-pyrazole-1-carboxamide in 5 ml of tetrahydrofuran was added slowly. When hydrogen evolution ceased, 1 ml of acetic anhydride was added and the mixture was stirred for 5 minutes. The reaction was partitioned between ethyl ether and brine, dried, concentrated, and chromatographed yielding 1.6 g of N,3-bis-(4-chlorophenyl)-4-dimethylcarbamoyl-4-methyl-N-acetyl-4,5-dihydro-1H-pyrazole-1-carboxamide, an oil. NMR and IR data were consistent with the structure.

EXAMPLE 130

Preparation of
N,3-bis-(4-chlorophenyl)-4-carbomethoxy-4-methyl-4,5-dihydro-1H-pyrazole-1-thiocarboxamide 4-chlorophenyl isothiocyanate and 3-(4-chlorophenyl)-4-methyl-4,5-dihydro-1H-pyrazole were used, by substantially following the procedures given in Example G, to prepare N,3-bis-(4-chlorophenyl)-4-methyl-4,5-dihydro-1H-pyrazole-1-thiocarboxamide, which was used, by substantially following the procedures given in Example 77 Method A, to prepare N,3-bis-(4-chlorophenyl)-4-carbomethoxy-4-methyl-4,5-dihydro-1H-pyrazole-1-thiocarboxamide, Mp 69°–78° C. NMR and IR data were consistent with the structure.

EXAMPLE 138

Preparation of
N,3-bis-(4-chlorophenyl)-4-carbomethoxy-4-methyl-N-dimethylcarbamoyl-4,5-dihydro-1H-pyrazole-1-carboxamide N,3-bis-(4-chlorophenyl)-4-carbomethoxy-4-methyl-4,5-dihydro-1H-pyrazole-1-carboxamide was treated with dimethylcarbamoyl chloride by substantially following the procedure given in Example 115 yielding N,3-bis-(4-chlorophenyl)-4-carbomethoxy-4-methyl-N-dimethylcarbamoyl-4,5-dihydro-1H-pyrazole-1-carboxamide, an oil which solidified on long standing. NMR and IR data were consistent with the structure.

EXAMPLE 145

Preparation of
N,3-bis-(4-chlorophenyl)-4-carbomethoxy-4-methyl-N-carbomethoxythio-4,5-dihydro-1H-pyrazole-1-carboxamide N,3-bis-(4-chlorophenyl)-4-carbomethoxy-4-methyl-4,5-dihydro-1H-pyrazole-1-carboxamide was treated with carbomethoxysulfenyl chloride by substantially following the procedure given in Example 115 yielding N,3-bis-(4-chlorophenyl)-4-carbomethoxy-4-methyl-N-carbomethoxythio-4,5-dihydro-1H-pyrazole-1-carboxamide, a foam. NMR and IR data were consistent with the structure.

EXAMPLE 149

Preparation of
N-(4-trifluoromethylphenyl)-3-(4-chlorophenyl)-4-carbomethoxy-4-methyl-4,5-dihydro-1H-pyrazole-1-carboxamide 4-trifluoromethylphenyl isocyanate and 3-(4-chlorophenyl)-4-methyl-4,5-dihydro-1H-pyrazole were used, by substantially following the procedures given in Example G, to prepare N-(4-trifluoromethylphenyl)-3-(4-chlorophenyl)-4-methyl-4,5-dihydro-1H-pyrazole-1-carboxamide which was used, by substantially following the procedures given in Example 77 Method A except that methyl chloroformate was used as the acylating agent, to prepare N-(4-trifluoromethylphenyl)-3-(4-chlorophenyl)-4-carbomethoxy-4-methyl-4,5-dihydro-1H-pyrazole-1-carboxamide, Mp 143°–146° C. NMR and IR data were consistent with the structure.

EXAMPLE 150

Preparation of
N,3-bis-(4-chlorophenyl)-4-carboxmethoxy-4-methyl-N-(2-nitrophenylsulfenyl)-4,5-dihydro-1H-pyrazole-1-carboxamide N,3-bis-(4-chlorophenyl)-4-carbomethoxy-4-methyl-4,5-dihydro-1H-pyrazole-1-carboxamide was treated with 2-nitrophenylsulfenyl chloride by substantially following the procedure given in Example 115 yielding N,3-bis-(4-chlorophenyl)-4-carbomethoxy-4-methyl-N-(2-nitrophenylsulfenyl)-4,5-dihydro-1H-pyrazole-1-carboxamide. NMR and IR data were consistent with the structure.

EXAMPLE 160

Preparation of
N,3-bis-(4-chlorophenyl)-4-carbomethoxy-4-methyl-N-(1-carbomethoxy-prop-2-yl-thio)-4,5-dihydro-1H-pyrazole-1-carboxamide N,3-bis-(4-chlorophenyl)-4-carbomethoxy-4-methyl-4,5-dihydro-1H-pyrazole-1-carboxamide was treated with (1-carbomethoxy-prop-2-yl)disulfide by substantially following the procedure given in Example 115 yielding N,3-bis-(4-chlorophenyl)-4-carbomethoxy-4-methyl-N-(1-carbomethoxy-prop-2-yl-thio)-4,5-dihydro-1H-pyrazole-1-carboxamide. NMR and IR data were consistent with the structure.

Surprisingly, many of the compounds of the present invention exhibit better pesticidal activity than the known dihydropyrazoles. Accordingly, compounds of the present invention represent a genuine enrichment of the art.

Certain of the 1-substituted-4-substituted-4,5-dihydro-1H-pyrazoles of the present invention show, for example, activity at a concentration of from about 2 ppm to about 15 ppm against Southern Armyworm; from about 0.1 ppm to about 10 ppm against Mexican Bean Beetle; and from about 1 ppm to about 10 ppm against Boll Weevil.

On the basis of their strong initial pesticidal activity and excellent residual pesticial activity, compounds according to the invention may be used in low dosages in controlling pests. The amount of dosage depends on a variety of factors, for example, the substance used, the kind of pest, the formulation used, the state of the crop infected with the pest and the prevailing weather conditions. In general, for the control of pests in agriculture and horticulture, a dosage corresponding to from about 0.1 grams to about 1000 grams of the active substance per hectare may be used and from about 5 grams to about 200 grams per hectare of the active substance is preferred.

Representative pests which can be controlled by the compounds of the present invention include:
American Cockroach (*Periplanta americana*)
Bean Leaf Beetle (*Cerotoma trifurcata*)
Bean Leaf Roller (*Urbanus proteus*)
Black Carpenter Ant (*Camponotus Pennsylvanicus*)
Black Cutworm (*Agrotis ipsilon*)
Boll Weevil (*Anthronomus grandis grandis*)
Colorado Potato Beetle (*Lepitinotarsa decemlineata*)
Fall Armyworm (*Spodoptera frugiperda*)
German Cockroach (*Blatella germanica*)
Green June Beetle (*Cotinis nitida*)
House Cricket (*Ancheta domesticus*)
Housefly (*Musca domestica*) p0 Mexican Bean Beetle (*Epilachna varivestis*)
Potato Leaf Hopper (*Empoasca fabae*)
Red Harvester Ant (*Pogonomyrmex barbatus*)
Red Imported Fire Ant (*Solenopsis invicta*)
Redlegged Grasshopper (*Melanopus femurrubrum*)
Southern Armyworm (*Spodoptera eridania*)
Southern Corn Rootworm (*Diabrotica undecimpunctata howardi*)
Tobacco Budworm (*Heliothis virescens*)

The compounds of the present invention, for practical applications, can be utilized in the form of compositions or formulations. In these compositions and formulations, the active substance is mixed with conventional inert (i.e., plant compatible and/or pesticidally inert) pesticide diluents or extenders such as solid carrier material or liquid carrier material, of the type usable in conventional pesticide compositions or formulations. If desired, adjuvants such as surfactants, stabilizers, antifoam agent and antidrift agents may also be combined.

Examples of compositions and formulations according to the invention are aqueous solutions and dispersions, oily solutions and oil dispersions, pastes, dusting powders, wettable powders, emulsifiable concentrates, flowables, granules, baits, invert emulsions, aerosol compositions and fumigating candles.

Wettable powders, pastes, flowables and emulsifiable concentrates are concentrated preparations which are diluted with water before or during use.

Baits are preparations generally comprising a food or other substance attractive to insects, that includes at least one lethal or non-lethal toxcant. Lethal toxicants kill insects upon ingesting the bait while non-lethal toxicants change the behavior and physiology of the insect for the purpose of control.

The invert emulsions are mainly used for air application, where large areas are treated with a comparatively small amount of preparation. The invert emulsion may be prepared in the spraying apparatus shortly before, or even during, the spraying operation by emulsifying water in an oil solution or an oil dispersion of the active substance.

Compositions and formulations are prepared in a known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g., dichlorodifluoromethane and trifluorochloromethane, as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, chloroethylenes, etc.), vegetable oils (e.g., soybean oil, cotton seed oil, corn oil, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; solid carriers including ground natural minerals, such as kaolins, clays, talc, chalk, quartz, attapulgite, montmorillonite or diatomaceous earth, and ground synthetic minerals, such as highly-dispersed silicic acid, alumina and silicates; solid carriers for granules include crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. The following may be chiefly considered for use as conventional carrier vehicle assistants: emulsifying agents, such as cationic and/or nonionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

If desired, it is possible to use colorants in compositions and formulations containing compounds of the present invention such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The active compounds of the present invention may be employed alone or in the form of mixtures with one another and/or with such solid and/or liquid dispersible carrier vehicles and/or with other known compatible active agents, especially plant protection agents, such as other arthropodicides, nematicides, fungicides, bactericides, rodenticides, herbicides, fertilizers, growth-regulating agents, synergists, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.001-99% by weight, and preferably between about 0.005-90% by weight, of the mixture. Carrier composition mixtures suitable for direct application or field application generally contemplate those in which the active compound is present in an amount substantially between about 0.00001-95%, preferably 0.00005-90%, by weight of the mixture. Thus the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, (e.g., a surface-active agent, such as an emulsifying agent and/or a dispersing agent), and an amount of the active compound which is effective for the purpose in question.

The active compounds can be applied as insecticide sprays by methods commonly employed, such as conventional high-gallonage hydraulic sprays, low gallonage sprays, ultra-low-volume sprays, airblast spray, aerial sprays, and dusts. If low volume applications are desired, a solution of the compound is usually used. In ultra-low-volume applications, a liquid composition containing the active compound is usually applied as a spray (e.g., mist) by means of atomizing equipment in finely divided form (average particle size of from about 50 to about 100 microns or less) using airplane crop spraying techniques. Typically only a few lines per hectare are needed and often amounts up to about 15 to 1000 g/hectare, preferably about 40 to 600 g/hectare are sufficient. With ultra-low-volume, it is possible to use highly concentrated liquid compositions with said liquid carrier vehicles containing from about 20 to about 95% by weight of the active compound.

Furthermore, the present invention contemplates methods of selectively killing, combating or controlling pests, which comprise applying to at least one of (a) such pests and (b) the corresponding habitat thereof (i.e., the locus to be protected, for example, to a growing crop or to an area where a crop is to be grown) a correspondingly combative or toxic amount (i.e., a pestically effective amount) of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting and the like.

It will be realized, of course, that the concentration of the particular active compound utilized in admixture with the carrier vehicle will depend upon such factors as the type of equipment employed, method of application, area to be treated, types of pests to be controlled and degree of infestation. Therefore, in special cases it is possible to go above or below the aforementioned concentration ranges.

Granular preparations are produced for example, by taking up the active substance in a solvent and by using the resulting solution, as the case may be in the presence of a binder, to impregnate a granular carrier material, such as porous granules (for example pumice and attaclay), or mineral non-porous granules (for example dried coffee grounds and chopped tobacco stems).

A granular preparation (frequently termed a "pellet") may alternatively be produced by compressing the active substance together with powdered minerals in the presence of lubricants and binders and by disintegrating and straining the composite to the desired grain size.

Dusts are obtainable by intimately mixing the active substance with an inert solid carrier material in a concentration of from about 1 to about 50% by weight. Examples of suitable solid carrier materials are talc, kaolin, pipe clay, diatomaceous earth, dolomite, gypsum, chalk, bentonite, attapulgite and colloidal $SiO_2$ or mixtures of these and similar substances. Alternatively organic carrier materials such, for example as ground walnut shells may be used.

Wettable powders and flowables are produced by mixing from about 10 to about 99 parts by weight of a solid inert carrier such, for example, as the aforementioned carrier materials with from about 1 to about 80 parts by weight of the active substance, from about 1 to about 5 parts by weight of a dispersing agent such, for example, as the lignosulfonates or alkylnaphthalene sulfonates known for this purpose and preferably also from about 0.5 to about 5 parts by weight of a wetting agent, such as fatty alcohol sulfates, or alkylarylsulfonates of fatty acid condensation products.

To produce emulsifiable concentrates the active compound is dissolved or finely divided in a suitable solvent which preferably is poorly miscible with water, an emulsifier being added to the resulting solution. Examples of suitable solvents are xylene, toluene, high-boiling aromatic petroleum distillates, for example solvent naphtha, distilled tar oil and mixtures of these liquids. Examples of suitable emulsifiers are alkylphenoxypolyglycol ethers, polyoxyethylene sorbitan esters of fatty acids or polyoxyethylene sorbitol esters of fatty acids. The concentration of the active compound in these emulsifiable concentrates is not restricted within narrow limits and may vary between about 2% and about 50% by weight. A suitable liquid highly concentrated primary composition other than an emulsifiable concentrate is a solution of the active substance in a liquid which is readily miscible with water, for example, acetone, to which solution a dispersant and, as the case may be, a wetting agent are added. When such a primary composition is diluted with water shortly before or during the spraying operation an aqueous dispersion of the active substance is obtained.

An aerosol preparation according to the invention is obtained in the usual manner by incorporating the active substance or a solution thereof in a suitable solvent in a volatile liquid suitable for use as a propellant such, for example, as a mixture of chlorine and fluorine derivatives of methane and ethane.

Fumigating candles or fumigating powders, i.e. preparations which then burning are capable of emitting a pesticidal smoke, are obtained by taking up the active substance in a combustible mixture which may, for example, comprise a sugar or a wood, preferably in the ground form, as a fuel, a substance to sustain combustion such, for example, as ammonium nitrate or potassium chlorate, and furthermore a substance for retarding combustion, for example kaolin, bentonite and/or colloidal silicic acid.

A bait preparation comprises a food or other substance attractive to pests, a carrier, the toxicant and may optionally include other substances commonly used in preparations of this kind, such as, a preservative to inhibit bacterial and fungal growth, a waterproofing agent to prevent disintegration under wet conditions and dyes or colorants as described above.

In addition to the aforementioned ingredients the preparations according to the invention may also contain other substances commonly used in preparations of this kind.

For example, a lubricant, such as calcium stearate or magnesium stearate, may be added to a wettable powder or to a mixture to be granulated. Furthermore there may, for example, be added "adhesives" such as polyvinylalcoholcellulose derivatives or other colloidal materials, such as casein, to improve the adherence of the pesticide to the surface to be protected.

Representative illustrative preparations of compositions and formulations including the compounds of the present invention are set forth below as Examples K through S.

EXAMPLE K

Granular

| Ingredient | %/wt. |
| --- | --- |
| Toxicant | 0.25 |
| Triton ® X-305 (binder) | 0.25 |
| Agsorb ® 24/48 (diluent) | 99.50 |

Preparation: The toxicant and Triton ® X-305 are dissolved into methylene chloride and the mixture is added to the Agsorb ® with continuous mixing. The methylene chloride is then allowed to evaporate.

EXAMPLE L

Dust

| Ingredient | %/wt. |
| --- | --- |
| Toxicant | 1.0 |
| Talc | 99.0 |

Preparation: Toxicant is dissolved in excess acetone and the mixture is impregnated onto the talc. The acetone is then permitted to evaporate.

EXAMPLE M

Wettable Powder

| Ingredient | %/wt. |
| --- | --- |
| Toxicant | 25.0 |
| Toxicant impurities | 6.3 |
| Duponal ® WA Dry (wetter) | 2.0 |
| Reax ® 45A (dispersant) | 5.0 |
| Barden clay (diluent) | 31.7 |
| HiSil ® 233 (diluent) | 30.0 |

Preparation: The toxicant is absorbed onto the Barden clay and HiSil ® carriers. The Duponal ® and Reax ® are then added and the entire dry mixture blended until homogeneous. The composition is then micronized to a fine particle size.

EXAMPLE N

Emulsifiable Concentrate

| Ingredient | %/wt. |
| --- | --- |
| Toxicant | 13.5 |
| Toxicant impurities | 1.5 |
| Sponto ® 232T (emulsifier) | 6.0 |
| Sponto ® 234T (emulsifier) | 4.0 |
| Cyclohexanone (solvent) | 22.5 |
| Tenneco ® 500–100 (solvent) | 52.5 |

Preparation: All ingredients are mixed together with continuous agitation until a homogeneous clear solution is obtained.

EXAMPLE O

Aerosol

| Ingredient | %/wt. |
| --- | --- |
| Toxicant | 0.5 |
| Freon 12 | 99.5 |

Preparation: The components are mixed and packaged under pressure in a suitable container equipped with a release spray valve.

EXAMPLE P

Fumigating Candle or Fumigating Powder

| Ingredient | %/wt. |
| --- | --- |
| Toxicant | 1.0 |
| Wood dust | 96.0 |
| Starch | 3.0 |

Preparation: Toxicant, wood dust, and starch are blended together and then molded into a candle using a small amount of water to activate the starch.

EXAMPLE Q

Bait

Method A

| Ingredient | %/wt. |
| --- | --- |
| Toxicant | 1.00 |
| Wheat Bran (carrier and attractant) | 89.95 |
| Corn Syrup (attractant) | 7.00 |
| Corn Oil (attractant) | 2.00 |

| Ingredient | %/wt. |
|---|---|
| Kathon ® 4200 (preservative) | 0.05 |

Preparation: The corn oil and corn syrup are added to the wheat bran with adequate mixing. The toxicant and Kathon ® are premixed with excess acetone and this solution is added to the wheat bran base with continued mixing. The acetone is then permitted to evaporate.

Method B

| Ingredient | %/wt. |
|---|---|
| Toxicant | 0.06 |
| Granulated Sugar (carrier and attractant) | 99.94 |

EXAMPLE R

Pellet

Same as Example Q, Method A, with this addition: the bait composition is formed into 1/4" diameter by 3/8" long pellets using a suitable die and press apparatus.

EXAMPLE S

Flowable

| Ingredient | %/wt. |
|---|---|
| Toxicant | 25.0 |
| Toxicant impurities | 6.3 |
| Duponal ® WA Dry (wetter) | 2.0 |
| Reax ® 45A (dispersant) | 5.0 |
| HiSil ® 233 (diluent) | 30.0 |
| Kelzan ® (thickener) | 0.5 |
| Water | 31.2 |

Preparation: The toxicant is absorbed onto the HiSil ® carrier. The Duponal ® and Reax ® are then added and the entire dry mixture blended until homogeneous. The composition is then micronized to a fine particle size. The resulting powder is suspended in water and the Kelzan ® added.

Compositions and formulations according to the present invention may also include known pesticidal compounds. This expands the spectrum of activity of the preparation and may give rise to synergism.

The following known insecticidal, fungicidal and acaricidal compounds are suitable for use in such a combined preparation.

Insecticides such as:
1. Chlorinated hydrocarbons, for example, 2,2-bis(p-chlorophenyl)-1,1,1-trichloroethane and hexachloroepoxyoctahydrodimethanonaphthalene;
2. Carbamates, for example N-methyl-1-naphthylcarbamate;
3. Dinitrophenols, for example 2-methyl-4,6-dinitrophenyl and (2-(2-butyl)-4,6-dinitrophenyl-3,3-dimethylacrylate;
4. Organic phosphorus compounds, such as dimethyl-2-methoxy-carbonyl-1-methylvinyl phosphate, O,O-diethyl-O-p-nitrophenylphosphorus thioate; N-monomethylamide of O,O-dimethyldithiophosphorylacetic acid;
5. Diphenylsulfides, for example p-chlorobenzyl or p-chlorophenyl sulfide and 2,4,4'-5-tetrachloridiphenylsulfide;
6. Diphenylsulfonates, for example p-chlorophenylbenzenesulfonate;
7. Methylcabinols, for example, 4,4-dichloro-1-trichloromethylbenzhydrol;
8. Quinoxaline compounds, such as methylquinoxaline dithiocarbonate;
9. Amidines such as N'-(4-chloro-O-tolyl) N,N-dimethylformamidine;
10. Pyrethroids such as Allethrin;
11. Biologicals such as *Bacillus thuringiensis* preparations;
12. Organic tin compounds such as tricyclohexyltin hydroxide;

Fungicides such as:

13. Organic mercury compounds, for example phenylmercuryacetate and methylmercurycyanoguanide;
14. Organic tin compounds, for example triphenyltin hydroxide and triphenyltin acetate;
15. Alkylenebisdithiocarbamates, for example, zinc-ethylenebisthiocarbamate and manganoethylenebisthiocarbamate; and furthermore
16. 2,4-dinitro-6-(2-octyl-phenylcrotonate), 1-bis(dimethylamino)phosphoryl-3-phenyl-5-amino-1,2,4-triazole, 6-methylquinoxaline-2,3-dithiocarbonate, 1,4-dithioanthraquinone-2,3-dicarbonitirle, N-trichloromethylthiophthalimide, N-trichloromethylthiotetrahydrophthalimide, N-(1,1,2,2-tetrachloroethylthio)-tetrahydrophthalimide, N-dichlorofluoromethylthio-N-phenyl-N'-dimethylsulfonyldiamide and tetrachloroisophthalonitrile.

BIOLOGICAL ACTIVITY

It has been found by biological evaluation examination that the compounds according to the invention have pesticidal activity and are capable of controlling larvae and adult forms of pests, especially the Mexican Bean Beetle, Southern Armyworm and Boll Weevils. In addition, compounds of the present invention were found active against pyrethroid resistant pests such as the Colorado Potato Beetle and Housefly.

In evaluating the pesticidal activity of the compounds of this invention, the following test procedures were employed.

Evaluations were made on the following insects:

| Common Name | Latin Name |
|---|---|
| Mexican Bean Beetle | *Epilachna varivestis* |
| Southern Armyworm | *Spodoptera eridania* |
| Boll Weevil | *Anthonomus grandis grandis* |

A test solution containing 600 parts per million (ppm) was made by dissolving the test compound in a solvent (acetone:methanol, 1:1), adding a surfactant and then water to give an acetone:methanol:water system of 10:10:80. A 1:1 mixture of an alkylarylpolyetheralcohol (sold under the trademark Triton ® X-155) and a modified phthalic glycerol alkyl resin (sold under the trademark Triton ® B-1956) was utilized at the equivalent of 1 ounce per 100 gal. of test solution as a surfactant.

Analogous solutions are made be serially diluting the 600 ppm test solution with water and surfactant to give concentrations of 150, 38, 10, 2.5, 0.6, 0.15, and 0.038 ppm. Not all compounds are tested at each of the several concentrations stated above. Particular concentrations of a particular compound tested are predicated upon responses obtained in a less definite range-finding assay. Test concentrations of a compound are selected as those most likely to differentiate dose response of a particular compound toward a particular test insect.

For the Mexican Bean Beetle and Southern Arymworm test, lima bean (*Phaseolus limensis* var. Woods' Prolific) seedlings in 3-inch pots were sprayed to runoff with the test solutions using a DeVilbiss atomizer at 20 psig. When dry, each plant was placed in a plastic box (7.5" long×5.25" wide×3.75" deep). Each box was then infested with 10 third instar larvae of either the Mexican Bean Beetle or the Southern Armyworm. The box was then sealed with a lid equipped with screened ventilation holes.

For the Boll Weevil, cotton (*Gossypium hirsutum* var. Acala) seedlings are treated in like manner. Ten young adult Boll Weevils are placed in each plastic box containing the treated plant that has been allowed to dry. The boxes are then sealed as noted above.

All treatments are maintained under continuous fluorescent light at 80 ±5° F. on open shelves for the course of the exposure period. Plants are watered as needed and replaced with untreated plants if they have been totally consumed as would be the case with ineffective treatments or untreated checks or controls.

Six days after treatment, the percent mortality is determined for each test species and spray conentration. The following table (Table II) gives the mortality data reported as percentage killed at the stated concentration for representative compounds of the present invention.

TABLE II

| | Biological Evaluation | | | | | |
|---|---|---|---|---|---|---|
| | Test Insect | | | | | |
| | Mexican Bean Beetle | | Southern Armyworm | | Boll Weevil | |
| Example No. | 10 ppm | 2.5 ppm | 38 ppm | 10 ppm | 38 ppm | 10 ppm |
| 2 | 100 | 70 | 100 | 100 | 100 | 100 |
| 16 | 60 | 40 | 90 | 0 | 100 | 90 |
| 66 | 100 | 10 | 100 | 100 | 100 | 80 |
| 77 | 100 | 90 | —[a] | 100 | 100 | 100 |
| 84 | 90 | 80 | 100 | 90 | 90 | 20 |
| 92 | — | 100 | 100 | 20 | 100 | 90 |
| 105 | 100 | 100 | 100 | 90 | 100 | 100 |
| 114 | 100 | 100 | 100 | 80 | 100 | 100 |
| 123 | 100 | 80 | — | 70 | 100 | 100 |
| 124 | 100 | 100 | 100[b] | 100[b] | 100 | 100 |
| 141 | — | 100 | 100 | 100 | 100 | 100 |
| 143 | — | 100 | — | 100 | — | 100 |
| 149 | — | 100 | — | 100 | — | —[c] |
| 152 | — | 100 | 100 | 100 | 100 | 100 |
| 186 | — | 100 | — | 100 | 100 | 90 |

[a]Not tested at the stated concentration.
[b]The maximum concentration originally applied was 2.5 ppm and failed to elicit kill. The Southern Armyworm assay was repeated giving the results shown and again gave 0% kill at 2.5 ppm.
[c]The maximum concentration applied was 2.5 ppm and elicited 100% kill.

It should be understood that the instant specification and examples are set forth by way of illustration and not limitation, and that various modifications and changes may be made without departing from the spirit and scope of the present invention as defined by the appended claims.

I claim:

1. A compound of the formula

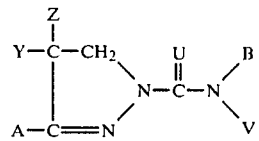

wherein
A is unsubstituted or substituted aryl;
B is unsubstituted or substituted aryl;
U is O, S or N—Q;
V is hydrogen, ($C_3$-$C_6$)cycloalkyl, unsubstituted or substituted aryl or $R^4$—Q;
Y is a group having the formula

where X is O or S;
Z is hydrogen, ($C_3$-$C_6$)cycloalkyl, unsubstituted or substituted aryl or $R^4$—Q;
Q is hydrogen, halogen, cyano, nitro, $OR^1$, $R^4OR^1$, $CO_2R^1$, $OR^4OR^1$, $CR^1R^2R^3$, $CONR^1R^2$, $NR^1R^2$, $NR^1COR^2$, $N(COR^1)COR^2$, $CSR^1$, $SR^1$, $SOR^1$, $SO_2R^1$, $NR^1SOR^2$, $R^4SR^1$, $OR^4SR^1$, $SR^4SR^1$, $SNHR^1$, $SNHSO_2R^1$, $CONHSR^1$, $OCOR^1$, $R^1$, $C(=NR^1)R^2$, $COR^1$, $N_3$, $OSO_2R^1$, $NR^1SO_2R^2$, $NR^1CSR^2$, alkenyl ($CR^1$=$CR^2R^3$), alkynyl ($C\equiv CR^1$), or aryl;
$R^1$, $R^2$ and $R^3$ are, independently, hydrogen, halogen, cyano, nitro, hydroxy, an alkoxy group (OR) having up to four carbon atoms, an amino group ($NH_2$), an alkylamino group (NHR) having up to six carbon atoms, a dialkylamino group ($NR_2$) having, independently, up to six carbon atoms in each alkyl moiety, a carboxy group ($CO_2H$), a carbalkoxy group ($CO_2R$) having up to six carbon atoms, an alkylcarbonyl group (COR) having up to six carbon atoms, an alkanoyloxy group (OCOR) having up to six carbon atoms, a carboxamido group ($CONH_2$), an N-alkylcarboxamido group (CONHR) having up to six carbon atoms in the alkyl moiety, an N,N-dialkylcarboxamido group ($CONR_2$) having, independently, up to six carbon atoms in each alkyl moiety, carbamoyloxy group ($OCONH_2$), an N-alkylcarbamoyloxy group (OCONHR) having up to six carbon atoms in the alkyl moiety, an N,N-dialkylcarbamoyloxy group ($OCONR_2$) having, independently, up to six carbon atoms in each alkyl moiety, a sulfhydril, an alkylsulfinyl group (—SOR) having up to six carbon atoms, an alkylsulfonyl group (—$SO_2R$) having up to six carbon atoms, an alkylsulfonato group (—$OSO_2R$) having up to six carbon atoms, an alkylthio group (SR) having up to six carbon atoms, a sulfonamido ($SO_2NH_2$), an N-alkylsulfonamido group ($SO_2NHR$) having up to six carbon atoms in the alkyl moiety, an N,N-dialkylsulfonamido group ($SO_2NR_2$) having, independently, up to six carbon atoms in each alkyl moiety, an N-alkyl-N-acylamino group (NRCOR) having, independently, up to six carbon atoms in each alkyl moiety, an N-alkyl-N-alkylsulfonylamino group ($NRSO_2R$) having, independently, up to six carbon atoms in each alkyl moiety, an alkylthiocarbonyl group (CSR) having up to six carbon atoms, an N-alkyl-N-thioacylamino group (NRCSR) having, independently, up to six carbon atoms in each alkyl moiety, an N-alkyl-N-alkylsulfinylamino group (NRSOR) having, independently, up to six carbon atoms in each alkyl moiety, an N,N-diacylamino group (N(COR)COR) having, independently, up to six carbon atoms in each alkyl moiety, an unsubstituted or substituted straight or branched chain ($C_1$-$C_6$)alkyl, ($C_3$-$C_6$)cycloalkyl or unsubstituted or substituted aryl where the substituent on the alkyl moiety can be one or more of the same or different hydroxy, halogen, cyano, nitro, alkoxy group (OR) having up to four carbon atoms, an amino group ($NH_2$), an alkylamino group (NHR) having up to six carbon atoms, a dialkylamino group ($NR_2$) having, independently, up to six carbon atoms in each alkyl moiety, a carboxy group ($CO_2H$), a carbalkoxy group ($CO_2R$) having up to six carbon atoms, an alkylcarbonyl group (COR) having up to six carbon atoms, an alkanoyloxy group (OCOR) having up to six carbon atoms, a carboxamido group ($CONH_2$), an N-alkylcarboxamido group (CONHR) having up to six carbon atoms in the alkyl moiety, an N,N-dialkylcarboxamido group ($CONR_2$) having, independently, up to six carbon atoms in each alkyl moiety, a carbamoyloxy group ($OCONH_2$), an N-alkylcarbamoyloxy group (OCONHR) having up to six carbon atoms in the alkyl moiety, an N,N-dialkylcarbamoyloxy group ($OCONR_2$) having, independently, up to six carbon atoms in each alkyl moiety, a sulfhydril, an alkylsulfinyl group (—SOR) having up to six carbon atoms, an alkylsulfonyl group (—$SO_2R$) having up to six carbon atoms, an alkylsulfonato group (—$OSO_2R$) having up to six carbon atoms, an alkylthio group (SR) having up to six carbon atoms, a sulfonamido ($SO_2NH_2$), an N-alkylsulfonamido group ($SO_2NHR$) having up to six carbon atoms in the alkyl moiety, an N,N-dialkylsulfonamido group ($SO_2NR_2$) having, independently, up to six carbon atoms in each alkyl moiety, an N-alkyl-N-acylamido group (NRCOR) having, independently, up to six carbon atoms in each alkyl moiety, an N-alkyl-N-alkylsulfonylamino (NRSO$_2$R), having, independently, up to six carbon atoms in each alkyl moiety, an alkylthiocarbonyl group (CSR) having up to six carbon atoms, an N-alkyl-N-thioacylamino group (NRCSR) having, independently, up to six carbon atoms in each alkyl moiety, an N-alkyl-N-alkylsulfinylamino (NRSOR) having, independently, up to six carbon atoms in each alkyl moiety, an N,N-diacylamino group (N(COR)COR) having, independently, up to six carbon atoms in each alkyl moiety, or an unsubstituted or substituted aryl group, where R is an alkyl group having the stated number of carbon atoms;

$R^4$ is

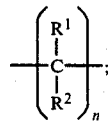

G is ($C_3$-$C_6$)cycloalkyl, unsubstituted or substituted aryl or $R^4$—Q; and n is an integer from 0 to 10; or an agronomically acceptable salt thereof;

wherein unsubstituted or substituted aryl is phenyl, optionally substituted with 1–5 substituents independently chosen from W; naphthyl, optionally substituted with 1–7 substituents independently chosen from W; a pyrryl; furyl; thienyl; imidazolyl; oxazolyl; thiazolyl; pyrazolyl; pyridyl or pyrimidyl optionally substituted with 1–4 substituents independently chosen from W; where W is halogen, cyano, nitro, $R^1$, $CO_2R^1$, $CONR^1R^2$, $CR^1$=$CR^2R^3$, C≡$CR^1$, $SR^1$, $OR^1$, $NR^1R^2$, $SOR^1$, $SO_2R^1$, $OSO_2R^1$, $NR^1COR^2$, $SF_5$, $CF_3$, $OCF_3$, $OCF_2H$, $SCF_3$, $OCF_2Br$, $SCF_2Br$, $SCF_2Cl$, $SCF_2H$, $NR^1SO_2R^2$ or $N(COR^1)COR^2$.

2. The compound according to claim 1 wherein R, $R^1$, $R^2$, $R^3$ and $R^4$, G, Q and n are as defined in claim 1 and A is unsubstituted or substituted phenyl;
B is unsubstituted or substituted phenyl;
U is O or S;
V is hydrogen, ($C_3$-$C_6$)cycloalkyl, unsubstituted or substituted phenyl or $R^4$—Q;
Y is a group having the formula

where X is O or S; and
Z is hydrogen, ($C_3$-$C_6$)cycloalkyl, unsubstituted or substituted phenyl or $R^4$—Q; or
an agronomically acceptable salt thereof and the substituents on the phenyl ring are independently chosen from W; and W is halogen, cyano, nitro, $R^1$, $CO_2R^1$, $CONR^1R^2$, $CR^1$=$CR^2R^3$, C≡$CR^1$, $SR^1$, $OR^1$, $NR^1R^2$, $SOR^1$, $SO_2R^2$, $OSO_2R^2$, $NR^1COR^2$, $SF_5$, $CF_3$, $OCF_3$, $OCF_2H$, $SCF_3$, $OCF_2Br$, $SCF_2Br$, $SCF_2Cl$, $SCF_2H$, $NR^1SO_2R^2$ or $N(COR^1)COR^2$.

3. The compound according to claim 2 wherein A, U, Y, Z, Q, R, $R^1$, $R^2$, $R^3$, $R^4$, G and n are as defined in claim 3 and B is substituted phenyl; and
V is hydrogen, unsubstituted or substituted phenyl or $R^4$—Q; or an agronomically acceptable thereof.

4. The compound according to claim 3 wherein U, Y, Q, R, $R^1$, $R^2$, $R^3$, $R^4$, G and n are as defined in claim 4 and A is unsubstituted or monosubstituted or disubstituted phenyl;
B is monosubstituted or disubstituted phenyl;
V is hydrogen or $R^4$—Q; and
Z is hydrogen, unsubstituted or substituted phenyl, or $R^4$—Q; or an agronomically acceptable salt thereof.

5. The compound according to claim 4 wherein V, Z, Q, R, $R^1$, $R^2$, $R^3$, $R^4$, G and n are as defined in claim 5 and A is monosubstituted phenyl;
B is monosubstituted phenyl;
U is O; and
Y is

or an agronomically acceptable salt thereof.

6. The compound according to claim 5 wherein
A is monosubstituted phenyl where the substituent is fluoro, chloro, bromo, trifluoromethyl, trifluoromethoxy, difluoromethoxy or methyl;
B is monosubstituted phenyl where the substituent is fluoro, chloro, bromo, trifluoromethyl, trifluoromethoxy, difluoromethoxy, carbomethoxy, carboethoxy, carboisopropoxy, methylthio or methylsulfonyl;
U is O;
V is hydrogen, lower ($C_1$–$C_6$) straight or branched chain unsubstituted or substituted alkyl, lower ($C_1$–$C_6$)alkoxy, lower ($C_1$–$C_6$)alkylsulfenyl, unsubstituted or substituted arylsulfenyl,

where X is O or S and $R^1$ is as defined in claim 5, cyano, lower ($C_1$–$C_6$)alkylheteroalkyl, wherein the substituent or the alkyl moiety is lower ($C_1$–$C_4$)alkoxy, lower ($C_1$–$C_4$)alkylsulfenyl, unsubstituted or substituted phenylsulfenyl, lower ($C_1$–$C_4$)carboalkoxy, cyano or lower ($C_1$–$C_4$)alkylheteroalkyl;
Y is

Z is hydrogen, lower ($C_1$–$C_4$)alkyl, or unsubstituted or substituted phenyl; and
G is hydroxy, lower ($C_1$–$C_4$)alkyl, lower ($C_1$–$C_4$)alkoxy, lower ($C_1$–$C_4$)alkylamino, lower dialkylamino having independently one to four carbon atoms in each alkyl moiety, or phenyl.
7. The compound according to claim 6 wherein
A is 4-chlorophenyl, 4-bromophenyl, 4-trifluoromethylphenyl, 4-trifluoromethoxyphenyl or 4-difluoromethoxphenyl;
B is 4-chlorophenyl, 4-bromophenyl, 4-carbomethoxyphenyl, 4-carboethoxyphenyl, 4-carboisopropoxyphenyl, 4-difluoromethoxyphenyl, 4-trifluoromethoxyphenyl, 4-trifluoromethylphenyl, 4-methylthiophenyl or 4-methylsulfonylphenyl;
U is O;
V is hydrogen, methyl, methylsulfenyl, 2-nitrophenylsulfenyl, carbomethoxy, acetyl, trifluoroacetyl, formyl or methoxalyl;
Y is

Z is hydrogen, methyl, phenyl, 4-chlorophenyl, 4-trifluoromethylphenyl, 4-trifluoromethoxyphenyl, 4-trifluorothiomethoxyphenyl, 4-difluoromethoxyphenyl or 4-difluorobromothiomethoxyphenyl; and
G is hydroxy, methyl, ethyl, methoxy, ethoxy, dimethylamino or phenyl.
8. The compound according to claim 7 wherein
A is 4-chlorophenyl;
B is 4-chlorophenyl;
U is O;
V is hydrogen;
Y is

Z is methyl; and
G is methoxy.
9. The compound according to claim 7 wherein
A is 4-chlorophenyl;
B is 4-chlorophenyl;
U is O;
V is hydrogen;
Y is

Z is methyl; and
G is ethoxy.
10. The compound according to claim 7 wherein
A is 4-chlorophenyl;
B is 4-chlorphenyl;
U is O;
V is hydrogen;
Y is

Z is methyl; and
G is dimethylamino.
11. The compound according to claim 7 wherein
A is 4-chlorophenyl;
B is 4-chlorophenyl;
U is O;
V is carbomethoxy;
Y is

Z is methyl; and
G is methoxy.
12. The compound according to claim 7 wherein
A is 4-chlorophenyl;
B is 4-chlorophenyl;
U is O;
V is acetyl;
Y is

Z is methyl; and
G is methoxy.
13. The compound according to claim 7 wherein
A is 4-chlorophenyl;
B is 4-chlorophenyl;
U is O;
V is trifluoroacetyl;
Y is

14. The compound according to claim 7 wherein
A is 4-chlorophenyl;
B is 4-chlorophenyl;
U is O;
V is formyl;
Y is

Z is methyl; and
G is methoxy.
15. The compound according to claim 7 wherein
A is 4-chlorophenyl;
B is 4-chlorophenyl;
U is O;
V is methoxalyl;
Y is

Z is methyl; and
G is methoxy.
16. The compound according to claim 7 wherein
A is 4-chlorophenyl;
B is 4-bromophenyl;
U is O;
V is hydrogen
Y is

Z is methyl; and
G is methoxy.
17. The compound according to claim 7 wherein
A is 4-chlorophenyl;
B is 4-trifluoromethylphenyl;
U is O;
V is hydrogen;
Y is

Z is methyl; and
G is methoxy.
18. The compound according to claim 7 wherein
A is 4-trifluoromethylphenyl;
B is 4-trifluoromethylphenyl;
U is O;
V is hydrogen;
Y is

Z is methyl; and
G is methoxy.
19. The compound according to claim 7 wherein
A is 4-chlorophenyl;
B is 4-trifluoromethoxyphenyl;
U is O;
V is hydrogen;
Y is

Z is methyl; and
G is methoxy.
20. An insecticidal composition comprising an insecticidally effective amount of a compound according to claim 1 and an agronomically acceptable carrier.
21. The composition according to claim 20 wherein said compound is present at from about 0.00001 to about 99% by weight of the composition.
22. The composition according to claim 21 wherein said compound is present at from about 0.00005 to about 90% by weight of the composition.
23. The composition according to claim 20 wherein said compound is N,3-bis-4-(4-chlorophenyl)-4-carbomethoxy-4-methyl-4,5-dihydro-1H-pyrazole-1-carboxamide.
24. The composition according to claim 20 wherein said compound is N,3-bis-(4-chlorophenyl)-4-carboethoxy-4-methyl-4,5-dihydro-1H-pyrazole-1-carboxamide.
25. The composition according to claim 20 wherein said compound is N,3-bis-(4-chlorophenyl)-4-dimethylcarboxamido-4-methyl-4,5-dihydro-1H-pyrazole-1-carboxamide.
26. The composition according to claim 20 wherein said compound is N,3-bis-(4-chlorophenyl)-4-carbomethoxy-4-methyl-N-carbomethoxy-4,5-dihydro-1H-pyrazole-1-carboxamide.
27. The composition according to claim 20 wherein said compound is N,3-bis-(4-chlorophenyl)-4-carbomethoxy-4-methyl-N-acetyl-4,5-dihydro-1H-pyrazole-1-carboxamide.
28. The composition according to claim 20 wherein said compound is N,3-bis-(4-chlorophenyl)-4-carbomethoxy-4-methyl-N-trifluoroacetyl-4,5-dihydro-1H-pyrazole-1-carboxamide.
29. The composition according to claim 20 wherein said compound is N,3-bis-(4-chlorophenyl)-4-carbomethoxy-4-methyl-N-formyl-4,5-dihydro-1H-pyrazole-1-carboxamide.
30. The composition according to claim 20 wherein said compound is N,3-bis-(4-chlorophenyl)-4-carbomethoxy-4-methyl-N-methoxalyl-4,5-dihydro-1H-pyrazole-1-carboxamide.
31. The composition according to claim 20 wherein said compound is N-(4-bromophenyl)-3-(4-chlorophenyl)-4-carbomethoxy-4-methyl-4,5-dihydro-1H-pyrazole-1-carboxamide.
32. The composition according to claim 20 wherein said compound is N-(4-trifluoromethylphenyl)-3-(4-chlorophenyl)-4-carbomethoxy-4-methyl-4,5-dihydro-1H-pyrazole-1-carboxamide.
33. The composition according to claim 20 wherein said compound is N,3-bis-(4-trifluoromethylphenyl)-4-carbomethoxy-4-methyl-4,5-dihydro-1H-pyrazole-1-carboxamide.
34. The composition according to claim 20 wherein said compound is N-(4-trifluoromethoxyphenyl)-3-(4-chlorophenyl)-4-carbomethoxy-4-methyl-4,5-dihydro-1H-pyrazole-1-carboxamide.

35. A method of controlling insects which comprises applying to the insects or to the loci to be freed or protected from attack by insects an insecticidally effective amount of a compound according to claim 1.

36. The method of claim 35 wherein said compound is applied at from about 0.1 to about 1000 grams per hectare.

37. The method of claim 36 wherein said compound is applied at from about 5 to about 200 grams per hectare.

38. The method of claim 35 wherein the compound is N,3-bis-4-(4-chlorophenyl)-4-carbomethoxy-4-methyl-4,5-dihydro-1H-pyrazole-1-carboxamide.

39. The method of claim 35 wherein the compound is N,3-bis-(4-chlorophenyl)-4-carboethoxy-4-methyl-4,5-dihydro-1H-pyrazole-1-carboxamide.

40. The method of claim 35 wherein the compound is N,3-bis-(4-chlorophenyl)-4-dimethylcarboxamido-4-methyl-4,5-dihydro-1H-pyrazole-1-carboxamide.

41. The method of claim 35 wherein the compound is N,3-bis-(4-chlorophenyl)-4-carbomethoxy-4-methyl-N-carbomethoxy-4,5-dihydro-1H-pyrazole-1-carboxamide.

42. The method of claim 35 wherein the compound is N,3-bis-(4-chlorophenyl)-4-carbomethoxy-4-methyl-N-acetyl-4,5-dihydro-1H-pyrazole-1-carboxamide.

43. The method of claim 35 wherein the compound is N,3-bis-(4-chlorophenyl)-4-carbomethoxy-4-methyl-N-trifluoroacetyl-4,5-dihydro-1H-pyrazole-1-carboxamide.

44. The method of claim 35 wherein the compound is N,3-bis-(4-chlorophenyl)-4-carbomethoxy-4-methyl-N-formyl-4,5-dihydro-1H-pyrazole-1-carboxamide.

45. The method of claim 35 wherein the compound is N,3-bis-(4-chlorophenyl)-4-carbomethoxy-4-methyl-N-methoxalyl-4,5-dihydro-1H-pyrazole-1-carboxamide.

46. The method of claim 35 wherein the compound is N-(4-bromophenyl)-3-(4-chlorophenyl)-4-carbomethoxy-4-methyl-4,5-dihydro-1H-pyrazole-1-carboxamide.

47. The method of claim 35 wherein the compound is N-(4-trifluoromethylphenyl)-3-(4-chlorophenyl)-4-carbomethoxy-4-methyl-4,5-dihydro-1H-pyrazole-1-carboxamide.

48. The method of claim 35 wherein the compound is N,3-bis-(4-trifluoromethylphenyl)-4-carbomethoxy-4-methyl-4,5-dihydro-1H-pyrazole-1-carboxamide.

49. The method of claim 35 wherein the compound is N-(4-trifluoromethoxyphenyl)-3-(4-chlorophenyl)-4-carbomethoxy-4-methyl-4,5-dihydro-1H-pyrazole-1-carboxamide.

* * * * *